US011084002B2

(12) United States Patent
Hoek et al.

(10) Patent No.: US 11,084,002 B2
(45) Date of Patent: *Aug. 10, 2021

(54) UNIVERSAL SCALABLE AND COST-EFFECTIVE SURFACE MODIFICATIONS

(71) Applicant: The Regents of the University of California, Oakland, CA (US)

(72) Inventors: Eric M. Hoek, Los Angeles, CA (US); Richard B. Kaner, Los Angeles, CA (US); Brian T. McVerry, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/404,372

(22) Filed: May 6, 2019

(65) Prior Publication Data

US 2019/0351375 A1    Nov. 21, 2019

Related U.S. Application Data

(63) Continuation of application No. 15/581,783, filed on Apr. 28, 2017, now Pat. No. 10,315,169, which is a
(Continued)

(51) Int. Cl.
  *B01D 71/78*     (2006.01)
  *B01D 65/08*     (2006.01)
  (Continued)

(52) U.S. Cl.
  CPC ............. *B01D 71/78* (2013.01); *B01D 61/08* (2013.01); *B01D 65/08* (2013.01);
  (Continued)

(58) Field of Classification Search
  CPC ............................. B01D 71/78; B01D 71/76
  See application file for complete search history.

(56) References Cited

U.S. PATENT DOCUMENTS 3,796,314 A    3/1974  Kolek
5,753,008 A    5/1998  Friesen et al.
(Continued)

FOREIGN PATENT DOCUMENTS

FR    2989215 A1    10/2013
JP    56067848 A    7/1981
(Continued)

OTHER PUBLICATIONS

EIC search report-2020.*
(Continued)

*Primary Examiner* — Krishnan S Menon
(74) *Attorney, Agent, or Firm* — Foley Hoag LLP; David P. Halstead; David S. Surry

(57) ABSTRACT

Disclosed are fouling resistant filtration membranes comprising a polymeric thin-film membrane comprising a surface. Also disclosed are methods of modifying thin-film filtration membranes, thereby improving, for example, the anti-fouling properties of the membranes. Also disclosed are methods of purifying water using the disclosed membranes. This abstract is intended as a scanning tool for purposes of searching in the particular art and is not intended to be limiting of the present invention.

11 Claims, 22 Drawing Sheets

Related U.S. Application Data continuation of application No. 14/768,887, filed as application No. PCT/US2014/017758 on Feb. 21, 2014, now Pat. No. 9,662,617.

(60) Provisional application No. 61/767,736, filed on Feb. 21, 2013.

(51) Int. Cl.

| | | |
|---|---|---|
| *B01D 67/00* | (2006.01) | |
| *B01D 71/76* | (2006.01) | |
| *B01D 61/08* | (2006.01) | |
| *C02F 1/44* | (2006.01) | |
| *C07C 247/18* | (2006.01) | |
| *B01D 69/08* | (2006.01) | |
| *B01D 61/02* | (2006.01) | |
| *B01D 69/02* | (2006.01) | |
| *B01D 71/56* | (2006.01) | |
| *C02F 103/08* | (2006.01) | |

(52) U.S. Cl.
CPC ..... *B01D 67/0088* (2013.01); *B01D 67/0093* (2013.01); *B01D 71/76* (2013.01); *C02F 1/441* (2013.01); *C07C 247/18* (2013.01); *B01D 61/025* (2013.01); *B01D 69/02* (2013.01); *B01D 69/08* (2013.01); *B01D 71/56* (2013.01); *B01D 2323/345* (2013.01); *B01D 2323/36* (2013.01); *B01D 2325/48* (2013.01); *C02F 2103/08* (2013.01)

(56) References Cited

U.S. PATENT DOCUMENTS

| | | | |
|---|---|---|---|
| 8,029,857 | B2 | 10/2011 | Hoek et al. |
| 8,132,677 | B2 | 3/2012 | Liu et al. |
| 8,530,269 | B2 | 9/2013 | Chua et al. |
| 8,550,256 | B1 | 10/2013 | Diep et al. |
| 9,662,617 | B2 | 5/2017 | Hoek et al. |
| 10,315,169 | B2 | 6/2019 | Hoek et al. |
| 10,629,880 | B2 | 4/2020 | McVerry et al. |
| 10,729,822 | B2 | 8/2020 | Kaner et al. |
| 2002/0122872 | A1 | 9/2002 | Leukel et al. |
| 2007/0254006 | A1 | 11/2007 | Loose et al. |
| 2008/0017512 | A1 | 1/2008 | Bordunov et al. |
| 2009/0155335 | A1 | 6/2009 | O'Shaughnessey et al. |
| 2009/0308804 | A1 | 12/2009 | Cohen et al. |
| 2011/0005997 | A1 | 1/2011 | Kurth et al. |
| 2011/0104573 | A1 | 5/2011 | Gogichev et al. |
| 2012/0201972 | A1 | 8/2012 | Hayashi et al. |
| 2012/0258313 | A1 | 10/2012 | Wen et al. |
| 2014/0206251 | A1 | 7/2014 | Stokes |
| 2015/0025168 | A1 | 1/2015 | Lienkamp et al. |
| 2016/0001236 | A1 | 1/2016 | Hoek et al. |
| 2016/0152008 | A1 | 6/2016 | Ogata et al. |
| 2017/0296986 | A1 | 10/2017 | Hoek et al. |
| 2017/0355799 | A1 | 12/2017 | Veiseh et al. |
| 2018/0159106 | A1 | 6/2018 | McVerry et al. |
| 2019/0185776 | A1 | 6/2019 | Kuramoto et al. |
| 2020/0203692 | A1 | 6/2020 | McVerry et al. |
| 2020/0338240 | A1 | 10/2020 | Kaner et al. |
| 2020/0385506 | A1 | 12/2020 | McVerry et al. |

FOREIGN PATENT DOCUMENTS

| | | |
|---|---|---|
| JP | 2010059346 A | 3/2010 |
| JP | 2017177754 A | 10/2017 |
| WO | WO-00/076641 A1 | 12/2000 |
| WO | WO-2004/100282 A2 | 11/2004 |
| WO | WO-2009/039467 A1 | 3/2009 |
| WO | WO-2009099126 A1 | 8/2009 |
| WO | WO-2010/006196 A2 | 1/2010 |
| WO | WO-2010/036452 A2 | 4/2010 |
| WO | WO-2011/060202 A1 | 5/2011 |
| WO | WO-2012/071461 A2 | 5/2012 |
| WO | WO-2014/001795 A1 | 1/2014 |
| WO | WO-2014/032005 A1 | 2/2014 |
| WO | WO-2016/083314 A1 | 6/2016 |
| WO | WO-2017170210 A1 | 10/2017 |
| WO | WO-2018/102517 A1 | 6/2018 |
| WO | WO-2019/094685 A1 | 5/2019 |
| WO | WO-2019/108871 A1 | 6/2019 |
| WO | WO-2020/247629 A1 | 12/2020 |

OTHER PUBLICATIONS

U.S. Appl. No. 14/768,887, status granted.
U.S. Appl. No. 15/581,783, status granted.
U.S. Appl. No. 15/827,788, status pending.
U.S. Appl. No. 16/206,596, status pending.
Batool et al., "Fabrication of covalently bonded nanostructured thin films of epoxy resin and polydimethylsiloxane for oil adsorption," Polymer Bulletin, 74(12):4827-4840 (2017).
Extended European Search Report issued by the European Patent Office in corresponding Application No. EP 14753770, dated Oct. 24, 2016.
Freger et al., "TFC polyamide membranes modified by grafting of hydrophilic polymers: an FT-IR/AFM/TEM study," J Mem Sci, 209:283-292 (2002).
International Search Report and Written Opinion for International Application No. PCT/US14/17758 dated May 30, 2014.
International Search Report and Written Opinion for International Application No. PCT/US17/63887 dated Jan. 26, 2018.
International Search Report and Written Opinion for International Application No. PCT/US2018/059967 dated Feb. 17, 2019.
International Search Report and Written Opinion for International Application No. PCT/US2018/063196 dated Mar. 10, 2019.
Khulbe et al., "The art of surface modification of synthetic polymeric membranes," J Appl Ploymer Sci, 115(2): 855-895 (2010).
Kuo et al., "Surface modification with poly(sulfobetaine methacrylate-co-acrylic acid) to reduce fibrinogen adsorption, platelet adhesion, and plasma coagulation," Biomacromolecules, 12(12):4348-4356 (2011).
Li et al., "Influence of polybenzimidazole main chain structure on H2/CO2 separation at elevated temperatures," Journal of Membrane Science, 461:59-68 (2014).
Liu et al., "Perfluorophenyl Azides: New Applications in Surface Functionalization and Nanomaterial Synthesis," Acc Chem Res, 43(11):1434-1443 (2010).
Liu et al., "Photoinitiated coupling of unmodified monosaccharides to iron oxide nanoparticles for sensing proteins and bacteria," Bioconjugate Chem, 20(7): 1349-1355 (2009).
Mandwar et al., "Perfluorophenyl azide immobilization chemistry for single molecule force spectroscopy of the concanavalin A/mannose interaction," Langmuir, 26(22): 16677-16680 (2010).
Mizutani et al., "Liquid, phenylazide-end-capped copolymers of epsilon-caprolactone and trimethylene carbonate: preparation, photocuring characteristics, and surface layering," Biomacromolecules, 3(4):668-675 (2002).
Mosnacek et al., "Photochemical grafting of polysulfobetaine onto polyethylene and polystyrene surfaces and investigation of long-term stability of the polysulfobetaine layer in seawater," Polymers for Advanced Technologies, 29(7):1930-1938 (2018).
Puleo et al., "Gas sorption and transport in substituted polystyrenes," Journal of Polymer Science Part B: Polymer Physics, 27(11):2385-2406 (1989).
Qureshi et al., "Nanoprotective layer-by-layer coatings with epoxy components for enhancing abrasion resistance: toward robust multimaterial nanoscale films," Acs Nano, 7(10):9336-9344 (2013).
Sakuragi et al., "A photoimmobilizable sulfobetaine-based polymer for a nonbiofouling surface," Materials Science and Engineering:C, 30(2):316-322 (2010).
Seo et al., "Simultaneous patterning of proteins and cells through bioconjugation with photoreactable phospholipid polymers," RSC Advances, 7(64):40669-40672 (2017).

(56) References Cited

OTHER PUBLICATIONS

Sundhoro et al., "Fabrication of carbohydrate microarrays on a poly (2-hydroxyethyl methacrylate)-based photoactive substrate," Organic & Biomolecular Chemistry, 14(3):1124-1130 (2015).

Yuwen, "Polymer-based photoactive surface for the efficient immobilization of nanoparticles, polymers, graphene and; carbohydrates," PDXScholar, Dissertation, Portland State University (Jan. 1, 2011).

Extended European Search Report for EP Application No. 17876218.3 dated Mar. 24, 2020.

Gerard et al., "Surface modification of poly(butylene terephthalate) nonwoven by photochemistry and biofunctionalization with peptides for blood filtration," Polymer Chemistry, 49(23): 5087-5099 (2011).

Khong et al., "General Photo-Patterning of Polyelectrolyte Thin Films via Efficient Ionic Bis(Fluorinated Phenyl Azide) Photo-Crosslinkers and their Post-Deposition Modification," Advanced Functional Materials, 17(14): 2490-2499 (2007).

Sundhoro et al., "Poly(HEMA-co-HEMA-PFA): Synthesis and preparation of stable micelles encapsulating imaging nanoparticles," Journal of Colloid and Interface Science, 500:1-8 (2017).

Anderson et al., "Conjugated Polymer Films for Gas Separations," Sci 252(5011):1412-1415 (1991).

Sivakumar et al., "Novel Microarrays for Simultaneous of Multiple Antiviral Antibodies," Plos One, 8(12):e81726/1-e81726/9 (2013).

Sundhoro et al., "Poly(HEMA-co-HEMA-PFA): Synthesis and preparation of stable micelles encapsulating imaging nanoparticles," Journal of Colloid and Interace Science, 500:1-8 (2017).

International Search Report and Written Opinion for International Application No. PCT/US2020/036121 dated Aug. 19, 2020.

Tanaka et al., "Synthesis and structures of zwitterionic polymers to induce electrostatic interaction with PDMS surface treated by air-plasma," Organic Chemistry, part ii:330-343 (2018).

\* cited by examiner

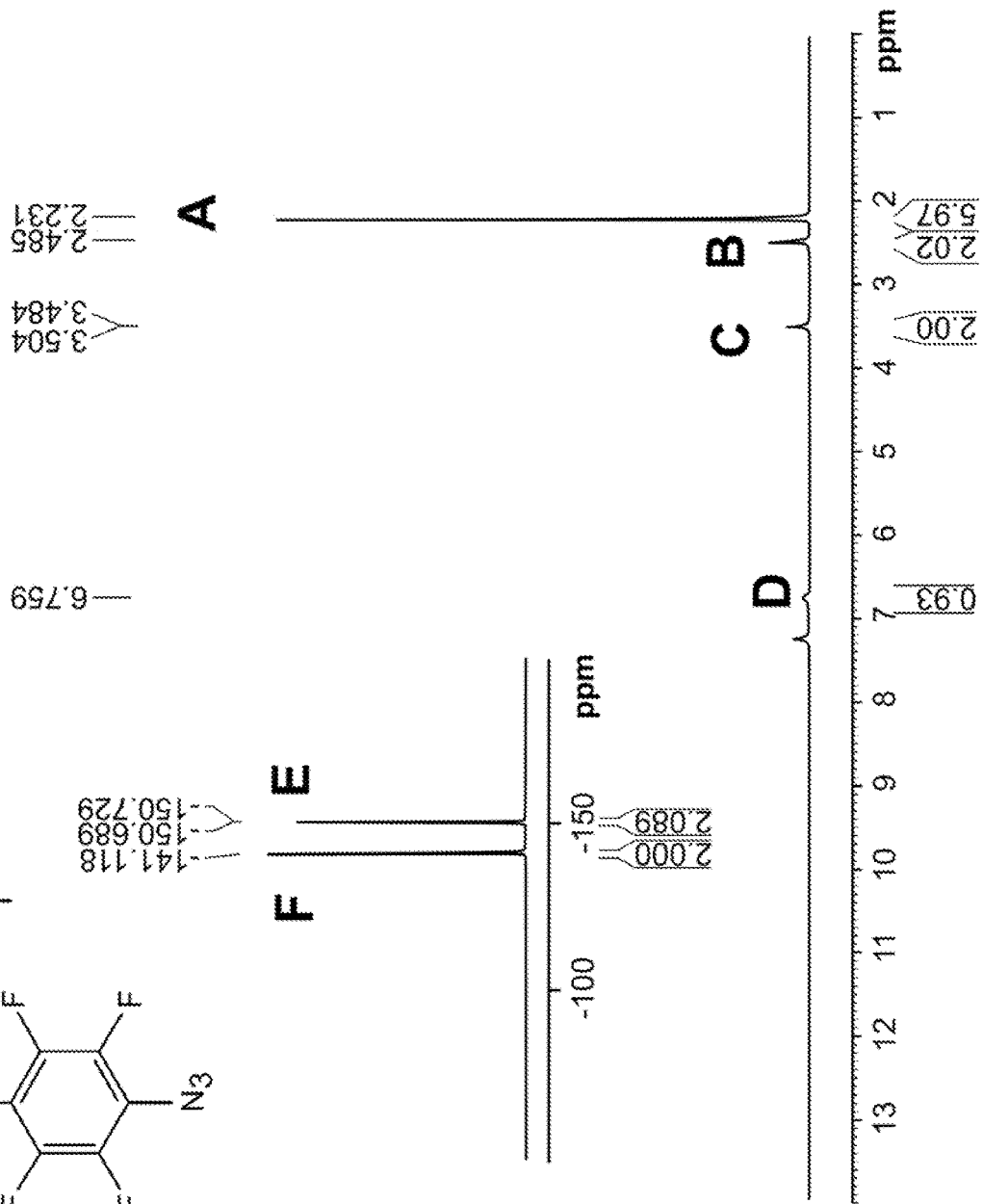
FIG. 9
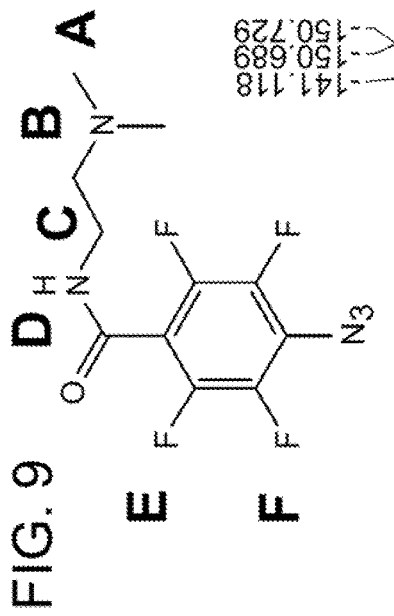

Commercial XLE Membrane

Contact Angle: 64°

PFPA-COONa Modified

Contact Angle: 42°

PFPA-SO$_3$Na Modified

Contact Angle: 35°

PFPA-SDEA Modified

Contact Angle: 60°

UNIVERSAL SCALABLE AND COST-EFFECTIVE SURFACE MODIFICATIONS

CROSS-REFERENCE TO RELATED APPLICATIONS

This application is a continuation of U.S. patent application Ser. No. 15/581,783, filed Apr. 28, 2017, which is a continuation of U.S. patent application Ser. No. 14/768,887, filed Aug. 19, 2015, now U.S. Pat. No. 9,662,617, which is the U.S. National Stage of PCT/US2014/017758, filed Feb. 21, 2014, which claims the benefit of U.S. Provisional Application No. 61/767,736, filed on Feb. 21, 2013, each of which is incorporated herein by reference in its entirety.

STATEMENT REGARDING FEDERALLY SPONSORED RESEARCH

This invention was made with Government support under Grant No. 0903720, awarded by the National Science Foundation (NSF). The Government has certain rights in the invention.

BACKGROUND

With rapid population growth and the emergence of clean energy technologies, worldwide freshwater availability is declining at alarming rates (Service, R. F. (2006) *Science* 313, 1088-1090). Already, 1.2 billion people do not have access to safe drinking water, with millions (mostly young children) dying annually from disease transmitted from contaminated water (Shannon, M., et al. (2008) *Nature* 452, 301-310; Elimelelch and Phillip (2011) *Science* 333, 712-717). Even developed countries such as the United States will be considered "water-stressed" before the end of the century (Service, R. F. (2006) *Science* 313, 1088-1090). Diminishing groundwater resources are being contaminated with increasing amounts of heavy metals, micropollutants, and reproductive toxins. Chemicals added to disinfect water supplies negatively impact the environment and often undergo side reactions that generate high levels of carcinogens in drinking water (Shannon, M., et al. (2008) *Nature* 452, 301-310). New technologies must be developed to treat water effectively from traditional and non-traditional sources to adequately supply global needs.

Reverse osmosis (RO) has emerged as a leading technology in water treatment for its ability to efficiently convert seawater and brackish water into high purity water for potable and high tech applications. The polymeric thin-film membranes used for RO exhibit high flux, high selectivity, low cost, and relatively low-energy expenditure compared to alternative desalination technologies (Elimelelch and Phillip (2011) *Science* 333, 712-717; Lee, K., et al. (2011) *J. Membr. Sci.* 370, 1-22). Acting as a physical barrier, RO membranes allow water molecules to permeate through a dense, microporous film and reject small dissolved solutes. Among numerous polymeric materials used to fabricate RO membranes, aromatic polyamide membranes are the most widely used because of their superior transport and separation properties. Thin-film composite membranes are produced on an industrial scale using roll-to-roll processing and are packaged into spiral wound elements to achieve optimal performance.

Although polyamide membranes have approached theoretical limits on performance, they are highly susceptible to biological surface fouling that significantly reduces intrinsic operational and economic advantages (Shannon, M., et al. (2008) *Nature* 452, 301-310; Elimelelch and Phillip (2011) *Science* 333, 712-717; Herzberg and Elimelech (2007) *J. Membr. Sci.* 295, 11-20). Microorganisms in the feed water adsorb onto the surface via hydrophobic interactions and block the flow of water through the membrane. Harsh chemical disinfectants used to prevent the growth of biofilms on the surface, such as chlorine and base treatments, prevent and remove biofilms from the surface but also attack the chemical bonds within the polyamide layer degrading the high selectivity of the membranes (Glater, J., et al. (1994) *Desalination* 95, 325-345; Kawaguchi and Tamura (1984) *J. Appl. Polymer Sci.* 29, 3359-3367). Thus, biogrowth inhibition and cleaning agents that are commonly used in water treatment cannot be used with RO membranes, increasing the pretreatment, operating and maintenance costs of desalination plants (Isaias, N. P. (2001) *Desalination* 139, 57-64; Redondo, J. A. (2001) *Desalination* 139, 28-31; Kang, G. D., et al. (2007) *J. Membr. Sci.* 300, 165-171).

Recently, researchers have attempted to reduce or prevent RO membrane biofouling by developing anti-fouling membrane surface treatments (Rana and Matsuura (2010) *Chemical Rev.* 110, 2448-2471; Kang and Cao (2012) *Water Research* 46, 584-600). By covalently modifying the surface with hydrophilic "brush" polymers (Belfer, S., et al. (1998) *J. Membr. Sci.* 139, 175-191; Van Wagner, E. M., et al. (2011) *J. Membr. Sci.* 367, 273-287; Kang, G., et al. (2011) *Desalination* 275, 252-259; Zou, L., et al. (2011) *J. Membr. Sci.* 369, 420-428; Lin, N. H., et al. (2010) *J. Materials Chem.* 29, 4642; Yang, R., et al. (2011) *Chem. Materials* 23, 1263-1272), hydrophobic interactions between the foulant and the membrane surface are obstructed (FIG. 1). In addition, initial attachment of biological cells and dissolved organics, a key step in biofilm formation, is impeded. Moreover, a hydrophilic surface forms a layer of hydration that prevents foulants from adsorbing onto the surface of the membrane film, thus allowing water to pass freely through the membrane.

Unfortunately, the designed chemical stability of polyamide membranes makes surface manipulations a difficult task. Previous studies have utilized reactive epoxide terminal groups (Van Wagner, E. M., et al. (2011) *J. Membr. Sci.* 367, 273-287), carbodiimide activation (Kang, G., et al. (2011) *Desalination* 275, 252-259), or radical initiated graft polymerizations that chemically attach the hydrophilic polymers to the polyamide surface (Kang and Cao (2012) *Water Research* 46, 584-600; Kang, G., et al. (2011) *Desalination* 275, 252-259; Zou, L., et al. (2011) *J. Membr. Sci.* 369, 420-428; Lin, N. H., et al. (2010) J. Materials Chem. 29, 4642; Yang, R., et al. (2011) *Chem. Materials* 23, 1263-1272). However, these modifications require long reaction times, exotic reaction conditions, and are performed in situ, preventing them from being easily translated into commercial roll-to-roll manufacturing processes for thin-film composite membranes.

Thus, there remains a need for scalable methods to produce anti-fouling RO membranes. Such membranes and methods related thereto are described herein.

SUMMARY

In accordance with the purpose(s) of the invention, as embodied and broadly described herein, the invention, in one aspect, relates to chlorine-tolerant polyamide membranes and their uses.

Disclosed are fouling resistant filtration membranes comprising a polymeric thin-film membrane comprising a surface, wherein the surface is modified with at least one residue of a compound having a structure represented by a formula:

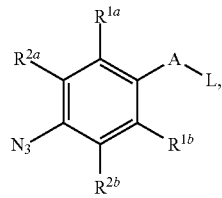

wherein A is selected from —C(=O)— and —(SO$_2$)—; wherein L is selected from —OQ, —O$^-$, —N$^+$R$^3$HQ and —NR$^3$Q; wherein Q is selected from hydrogen, a hydrophilic polymer, and a structure represented by a formula:

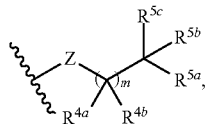

wherein Z is selected from —CR$^{6a}$R$^{6b}$—, —C(=O)—, —C(=NH)—, and —C(=NH)NR$^7$—; wherein m is an integer selected from 0, 1, 2, 3, 4, 5, 6, 7, and 8; wherein each of R$^{1a}$ and R$^{1b}$ is independently selected hydrogen and halogen; wherein each of R$^{2a}$ and R$^{2b}$ is halogen; wherein R$^3$, when present, is selected from hydrogen and C1-C4 alkyl; wherein each of R$^{4a}$ and R$^{4b}$, when present, is independently selected from hydrogen, halogen, —CN, —OH, —NR$^{8a}$R$^{8b}$, —NR$^{8a}$R$^{8b}$ H$^+$, C1-C4 alkyl, C1-C4 monohaloalkyl, C1-C4 polyhaloalkyl, —SO$_3^-$, —SO$_3$R$^9$, —CO$_2^-$, and —CO$_2$R$^9$; wherein each of R$^{5a}$, R$^{5b}$, and R$^{5c}$ is independently selected from hydrogen, halogen, —CN, —OH, —NR$^{10a}$R$^{10b}$, —NR$^{10a}$R$^{10b}$ H$^+$, C1-C4 alkyl, C1-C4 monohaloalkyl, C1-C4 polyhaloalkyl, —SO$_3^-$, —SO$_3$R$^{11}$, —CO$_2^-$, and —CO$_2$R$^{11}$; wherein each of R$^{6a}$ and R$^{6b}$, when present, is independently selected hydrogen, halogen, —CN, —OH, —NR$^{12a}$R$^{12b}$, —NR$^{12a}$R$^{12b}$ H$^+$, C1-C4 alkyl, C1-C4 monohaloalkyl, C1-C4 polyhaloalkyl, —SO$_3^-$, —SO$_3$R$^{13}$, —CO$_2^-$, and —CO$_2$R$^{13}$; wherein R$^7$, when present, is selected from hydrogen and C1-C4 alkyl; wherein each of R$^{8a}$ and R$^{8b}$, when present, is independently selected from hydrogen and C1-C4 alkyl; wherein R$^9$, when present, is selected from hydrogen and C1-C4 alkyl; wherein each of R$^{10a}$ and R$^{10b}$, when present, is independently selected from hydrogen and C1-C4 alkyl; wherein R$^{11}$, when present, is selected from hydrogen and C1-C4 alkyl; wherein each of R$^{12a}$ and R$^{12b}$, when present, is independently selected from hydrogen and C1-C4 alkyl; and wherein R$^{13}$, when present, is selected from hydrogen and C1-C4 alkyl.

Also disclosed are methods of modifying a thin-film membrane comprising a surface, the method comprising the step of bonding the surface with at least one residue of a compound having a structure represented by a formula:

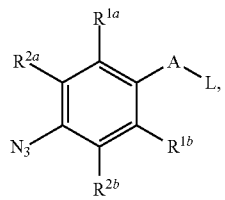

wherein A is selected from —C(=O)— and —(SO$_2$)—; wherein L is selected from —OQ, —O$^-$, —N$^+$R$^3$HQ and —NR$^3$Q; wherein Q is selected from hydrogen, a hydrophilic polymer, and a structure represented by a formula:

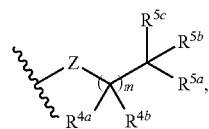

wherein Z is selected from —CR$^{6a}$R$^{6b}$—, —C(=O)—, —C(=NH)—, and —C(=NH)NR$^7$—; wherein m is an integer selected from 0, 1, 2, 3, 4, 5, 6, 7, and 8; wherein each of R$^{1a}$ and R$^{1b}$ is independently selected hydrogen and halogen; wherein each of R$^{2a}$ and R$^{2b}$ is halogen; wherein R$^3$, when present, is selected from hydrogen and C1-C4 alkyl; wherein each of R$^{4a}$ and R$^{4b}$, when present, is independently selected from hydrogen, halogen, —CN, —OH, —NR$^{8a}$R$^{8b}$, —NR$^{8a}$R$^{8b}$ H$^+$, C1-C4 alkyl, C1-C4 monohaloalkyl, C1-C4 polyhaloalkyl, —SO$_3^-$, —SO$_3$R$^9$, —CO$_2^-$, and —CO$_2$R$^9$; wherein each of R$^{5a}$, R$^{5b}$, and R$^{5c}$ is independently selected from hydrogen, halogen, —CN, —OH, —NR$^{10a}$R$^{10b}$, —NR$^{10a}$R$^{10b}$ H$^+$, C1-C4 alkyl, C1-C4 monohaloalkyl, C1-C4 polyhaloalkyl, —SO$_3^-$, —SO$_3$R$^{11}$, —CO$_2^-$, and —CO$_2$R$^{11}$; wherein each of R$^{6a}$ and R$^{6b}$, when present, is independently selected hydrogen, halogen, —CN, —OH, —NR$^{12a}$R$^{12b}$, —NR$^{12a}$R$^{12b}$ H$^+$, C1-C4 alkyl, C1-C4 monohaloalkyl, C1-C4 polyhaloalkyl, —SO$_3^-$, —SO$_3$R$^{13}$, —CO$_2^-$, and —CO$_2$R$^{13}$; wherein R$^7$, when present, is selected from hydrogen and C1-C4 alkyl; wherein each of R$^{8a}$ and R$^{8b}$, when present, is independently selected from hydrogen and C1-C4 alkyl; wherein R$^9$, when present, is selected from hydrogen and C1-C4 alkyl; wherein each of R$^{10a}$ and R$^{10b}$, when present, is independently selected from hydrogen and C1-C4 alkyl; wherein R$^{11}$, when present, is selected from hydrogen and C1-C4 alkyl; wherein each of R$^{12a}$ and R$^{12b}$, when present, is independently selected from hydrogen and C1-C4 alkyl; and wherein R$^{13}$, when present, is selected from hydrogen and C1-C4 alkyl.

Also disclosed are methods of modifying a thin-film membrane comprising a surface, the method comprising the step of bonding the surface with at least one residue of a compound comprising a singlet nitrene, thereby improving at least one property selected from resistance to fouling, surface charge, hydrophilicity, and roughness.

Also disclosed are compounds having a structure represented by a formula:

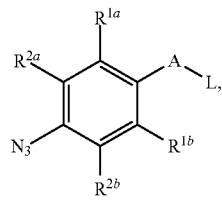

wherein m is an integer selected from 0, 1, 2, 3, 4, 5, 6, 7, and 8; wherein A is selected from —C(=O)— and —(SO$_2$)— and L is —OQ, or wherein A is —(SO$_2$)— and L is selected from —OQ and —NR$^3$Q; wherein Q is selected from hydrogen, a hydrophilic polymer, and a structure represented by a formula:

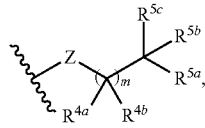

wherein Z is selected from —CR$^{6a}$R$^{6b}$—, —C(=O)—, —C(=NH)—, and —C(=NH)NR$^7$—; wherein each of R$^{1a}$ and R$^{1b}$ is independently selected hydrogen and halogen; wherein each of R$^{2a}$ and R$^{2b}$ is halogen; wherein R$^3$, when present, is selected from hydrogen and C1-C4 alkyl; wherein each of R$^{4a}$ and R$^{4b}$, when present, is independently selected from hydrogen, halogen, —CN, —OH, —NR$^{8a}$R$^{8b}$, —NR$^{8a}$R$^{8b}$ H$^+$, C1-C4 alkyl, C1-C4 monohaloalkyl, C1-C4 polyhaloalkyl, —SO$_3^-$, —SO$_3$R$^9$, —CO$_2^-$, and CO$_2$R$^9$; wherein each of R$^{5a}$, R$^{5b}$, and R$^{5c}$ is independently selected from hydrogen, halogen, —CN, —OH, —NR$^{10a}$R$^{10b}$, —NR$^{10a}$R$^{10b}$ H$^+$, C1-C4 alkyl, C1-C4 monohaloalkyl, C1-C4 polyhaloalkyl, —SO$_3^-$, —SO$_3$R$^{11}$, —CO$_2^-$, and —CO$_2$R$^{11}$; wherein each of R$^{6a}$ and R$^{6b}$, when present, is independently selected hydrogen, halogen, —CN, —OH, —NR$^{12a}$R$^{12b}$, —NR$^{12a}$R$^{12b}$ H$^+$, C1-C4 alkyl, C1-C4 monohaloalkyl, C1-C4 polyhaloalkyl, —SO$_3^-$, —SO$_3$R$^{13}$, —CO$_2^-$, and —CO$_2$R$^{13}$; wherein R$^7$, when present, is selected from hydrogen and C1-C4 alkyl; wherein each of R$^{8a}$ and R$^{8b}$, when present, is independently selected from hydrogen and C1-C4 alkyl; wherein R$^9$, when present, is selected from hydrogen and C1-C4 alkyl; wherein each of R$^{10a}$ and R$^{10b}$, when present, is independently selected from hydrogen and C1-C4 alkyl; wherein R$^{11}$, when present, is selected from hydrogen and C1-C4 alkyl; wherein each of R$^{12a}$ and R$^{12b}$, when present, is independently selected from hydrogen and C1-C4 alkyl; and wherein R$^{13}$, when present, is selected from hydrogen and C1-C4 alkyl.

Also disclosed are methods of purifying water, the method comprising: a) providing a disclosed membrane, or a membrane modified according to a disclosed process, the membrane having a first face and a second face; b) contacting the first face of the membrane with a first solution of a first volume having a first salt concentration at a first pressure; and c) contacting the second face of the membrane with a second solution of a second volume having a second salt concentration at a second pressure; wherein the first solution is in fluid communication with the second solution through the membrane, wherein the first salt concentration is higher than the second salt concentration, thereby creating an osmotic pressure across the membrane, and wherein the first pressure is sufficiently higher than the second pressure to overcome the osmotic pressure, thereby increasing the second volume and decreasing the first.

BRIEF DESCRIPTION OF THE FIGURES

The accompanying figures, which are incorporated in and constitute a part of this specification, illustrate several aspects and together with the description serve to explain the principles of the invention.

FIG. 9 shows representative $^1$H and $^{19}$F (inset) NMR spectral data of PFPA-CDEA.

Figure 1:
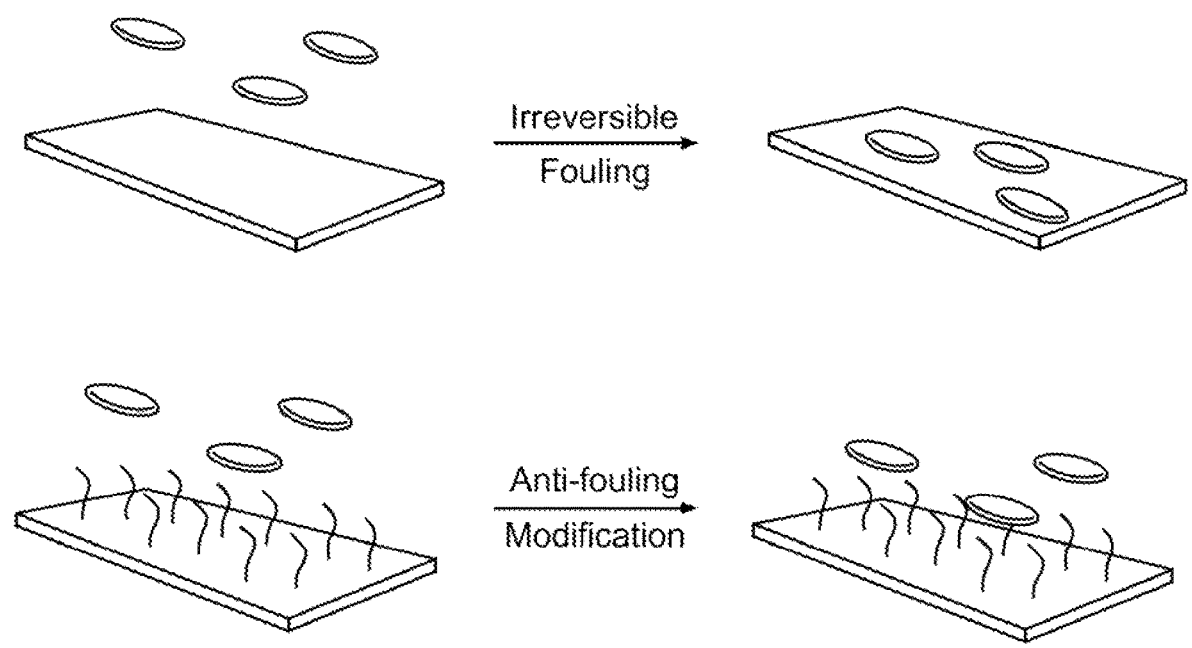
FIG. 1 shows representative data pertaining to the addition of hydrophilic brush polymers to prevent irreversible fouling.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein may be different from the actual publication dates, which can require independent confirmation.

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a component," "a polymer," or "a particle" includes mixtures of two or more such components, polymers, or particles, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that throughout the application, data is provided in a number of different formats and that this data represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance may or may not occur, and that the description includes instances where said event or circumstance occurs and instances where it does not.

As used herein, the terms "effective amount" and "amount effective" refer to an amount that is sufficient to achieve the desired result or to have an effect on an undesired condition.

The term "stable", as used herein, refers to compositions that are not substantially altered when subjected to conditions to allow for their production, detection, and, in certain aspects, their recovery, purification, and use for one or more of the purposes disclosed herein.

As used herein, the term "polymer" refers to a relatively high molecular weight organic compound, natural or synthetic, whose structure can be represented by a repeated small unit, the monomer (e.g., polyethylene, rubber, cellulose). Synthetic polymers are typically formed by addition or condensation polymerization of monomers.

As used herein, the term "homopolymer" refers to a polymer formed from a single type of repeating unit (monomer residue).

As used herein, the term "copolymer" refers to a polymer formed from two or more different repeating units (monomer residues). By way of example and without limitation, a copolymer can be an alternating copolymer, a random copolymer, a block copolymer, or a graft copolymer. It is also contemplated that, in certain aspects, various block segments of a block copolymer can themselves comprise copolymers.

As used herein, the term "oligomer" refers to a relatively low molecular weight polymer in which the number of repeating units is between two and ten, for example, from two to eight, from two to six, or form two to four. In one aspect, a collection of oligomers can have an average number of repeating units of from about two to about ten, for example, from about two to about eight, from about two to about six, or form about two to about four.

As used herein, the term "cross-linked polymer" refers to a polymer having bonds linking one polymer chain to another.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. Non-limiting examples of alkyls include C1-18 alkyl, C1-C12 alkyl, C1-C8 alkyl, C1-C6 alkyl, C1-C3 alkyl, and C1 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

The term "alkenyl" as used herein is a hydrocarbon group of 2 to 24 carbon atoms with a structural formula containing at least one carbon-carbon double bond. The alkenyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein. Non-limiting examples of alkenyls include C2-18 alkenyl, C2-12 alkenyl, C2-8 alkenyl, C2-6 alkenyl, and C2-3 alkenyl.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein. Non-limiting examples of alkynyls include C2-18 alkynyl, C2-12 alkynyl, C2-8 alkynyl, C2-6 alkynyl, and C2-3 alkynyl.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "ester" as used herein is represented by the formula —$OC(O)A^1$ or —$C(O)OA^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula —$(A^1O(O)C—A^2—C(O)O)_a$—, or $(A^1O(O)C—A^2—OC(O))_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula —$(A^1O—A^2O)_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "azide" as used herein is represented by the formula —$N_3$.

The term "thiol" as used herein is represented by the formula —SH.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific aspect or combination of aspects of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Fouling Resistant Filtration Membranes

In one aspect, the invention relates to fouling resistant filtration membranes comprising a polymeric thin-film membrane comprising a surface, wherein the surface is modified with at least one residue of a compound having a structure represented by a formula:

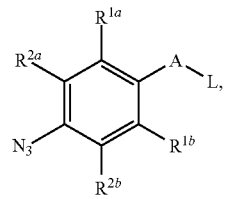

wherein A is selected from —C(=O)— and —(SO$_2$)—; wherein L is selected from —OQ, —O$^-$, —N$^+$R$^3$HQ and —NR$^3$Q; wherein Q is selected from hydrogen, a hydrophilic polymer, and a structure represented by a formula:

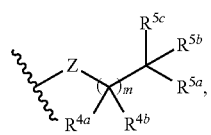

wherein Z is selected from —CR$^{6a}$R$^{6b}$—, —C(=O)—, —C(=NH)—, and —C(=NH)NR$^7$—; wherein m is an integer selected from 0, 1, 2, 3, 4, 5, 6, 7, and 8; wherein each of R$^{1a}$ and R$^{1b}$ is independently selected hydrogen and halogen; wherein each of R$^{2a}$ and R$^{2b}$ is halogen; wherein R$^3$, when present, is selected from hydrogen and C1-C4 alkyl; wherein each of R$^{4a}$ and R$^{4b}$, when present, is independently selected from hydrogen, halogen, —CN, —OH, —NR$^{8a}$R$^{8b}$, —NR$^{8a}$R$^{8b}$ H$^+$, C1-C4 alkyl, C1-C4 monohaloalkyl, C1-C4 polyhaloalkyl, —SO$_3$$^-$, —SO$_3$R$^9$, —CO$_2$$^-$, and —CO$_2$R$^9$; wherein each of R$^{5a}$, R$^{5b}$, and R$^{5c}$ is independently selected from hydrogen, halogen, —CN, —OH, —NR$^{10a}$R$^{10b}$, —NR$^{10a}$R$^{10b}$ H$^+$, C1-C4 alkyl, C1-C4 monohaloalkyl, C1-C4 polyhaloalkyl, —SO$_3$$^-$, —SO$_3$R$^{11}$, —CO$_2$$^-$, and —CO$_2$R$^{11}$; wherein each of R$^{6a}$ and R$^{6b}$, when present, is independently selected hydrogen, halogen, —CN, —OH, —NR$^{12a}$R$^{12b}$, —NR$^{12a}$R$^{12b}$ H$^+$, C1-C4 alkyl, C1-C4 monohaloalkyl, C1-C4 polyhaloalkyl, —SO$_3$$^-$, —SO$_3$R$^{13}$, —CO$_2$$^-$, and —CO$_2$R$^{13}$; wherein R$^7$, when present, is selected from hydrogen and C1-C4 alkyl; wherein each of R$^{8a}$ and R$^{8b}$, when present, is independently selected from hydrogen and C1-C4 alkyl; wherein R$^9$, when present, is selected from hydrogen and C1-C4 alkyl; wherein each of R$^{10a}$ and R$^{10b}$, when present, is independently selected from hydrogen and C1-C4 alkyl; wherein R$^{11}$, when present, is selected from hydrogen and C1-C4 alkyl; wherein each of R$^{12a}$ and R$^{12b}$, when present, is independently selected from hydrogen and C1-C4 alkyl; and wherein R$^{13}$, when present, is selected from hydrogen and C1-C4 alkyl. In a further aspect, the membrane is a reverse osmosis membrane. In a still further aspect, the membrane comprises at least one polyamide. In yet a further aspect, the polyamide is aromatic.

It is understood that the disclosed compositions, mixtures, and membranes can be employed in connection with the disclosed methods and uses.

1. Polymeric Thin-Film

In one aspect, the fouling resistant filtration membranes of the invention comprise a polymeric thin-film membrane comprising a surface. In various aspects, the polymeric thin-film can be adhered to the surface, the polymeric thin film can be bonded to the surface, and/or the polymeric thin-film can be adjacent to, in contact with or laminated to the surface. The polymeric support can be disposed upon a woven or non-woven textile laminated to the surface.

In various aspects, the polymeric thin-film comprises a polymer matrix, e.g., a three-dimensional polymer network, substantially permeable to water and substantially impermeable to impurities. For example, the polymer network can be a cross-linked polymer formed from reaction of at least one polyfunctional monomer with a difunctional or polyfunctional monomer.

The polymeric thin-film can be a three-dimensional polymer network such as an aliphatic or aromatic polyamide, aromatic polyhydrazide, poly-bensimidazolone, polyepiamine/amide, polyepiamine/urea, poly-ethyleneimine/urea, sulfonated polyfurane, polybenzimidazole, polypiperazine isophthalamide, a polyether, a polyether-urea, a polyester, or a polyimide or a copolymer thereof or a mixture thereof. Preferably, the polymeric thin film can be formed by an interfacial polymerization reaction or can be cross-linked subsequent to polymerization.

The polymeric thin-film can be an aromatic or non-aromatic polyamide such as residues of a phthaloyl (i.e., isophthaloyl or terephthaloyl) halide, a trimesyl halide, or a mixture thereof. In another example, the polyamide can be residues of diaminobenzene, triaminobenzene, polyetherimine, piperazine or poly-piperazine or residues of a trimesoyl halide and residues of a diaminobenzene. The film can also be residues of trimesoyl chloride and m-phenylenediamine. Further, the film can be the reaction product of trimesoyl chloride and m-phenylenediamine.

The polymeric thin-film can have a thickness of from about 1 nm to about 1000 nm. For example, the film can have a thickness of from about 10 nm to about 1000 nm, from about 100 nm to about 1000 nm, from about 1 nm to about 500 nm, from about 10 nm to about 500 nm, from about 50 nm to about 500 nm, from about 50 nm to about 200 nm, from about 50 nm to about 250 nm, from about 50 nm to about 300 nm, or from about 200 nm to about 300 nm.

2. Reverse Osmosis Membranes

In one aspect, the filtration membranes of the invention can be reverse osmosis (RO) membranes, including thin-film composite (TFC) membranes. Among particularly useful membranes for osmosis applications are those in which the semi-permeable or discriminating layer is a polyamide. A thin film composite membrane typically comprises a porous support and a semi-permeable polymer film polymerized on the porous support.

Composite polyamide membranes are typically prepared by coating a porous support with a polyfunctional amine monomer, most commonly coated from an aqueous solution. Although water is a preferred solvent, non-aqueous solvents can be utilized, such as acetonitrile and dimethylformamide (DMF). A polyfunctional acyl halide monomer (also referred to as acid halide) is subsequently coated on the support, typically coated first on the porous support followed by the acyl halide solution. Although one or both of the polyfunctional amine and acyl halide can be applied to the porous support from a solution, they can alternatively be applied by other means such as by vapor deposition, or heat.

In various aspects, the reverse osmosis membranes are prepared via a dip-coating process, whereby the membrane is dipped into a liquid coating solution and then withdrawn at a controlled speed. Coating thickness generally increases with faster withdrawal speed. A faster withdrawal speed adheres more fluid up onto the surface of the membrane before it has time to flow back down into the solution. Thickness is primarily affected by factors such as fluid viscosity, fluid density, and surface tension. Evaporation of the solvent can be accelerated by heated drying. In a further aspect, the coating may be cured using means such as conventional thermal, UV, or IR techniques depending on the coating solution formulation. In a further aspect, the reverse osmosis membranes are exposed to a light source, i.e., ultraviolet (UV) light in the range of from between 200 nm and 370 nm.

The resultant semi-permeable membrane can then be employed in a method of purifying or separating various liquids, such as water. Such a method typically comprises applying pressure to a water solution (e.g., a salt water solution) on the polymer matrix film side of the membrane; and collecting purified water on the other side of the membrane.

3. Properties of Membranes

In various aspects, the disclosed membranes can have various properties that provide the superior function of the membranes, including excellent flux, improved hydrophilicity, improved resistance to fouling, higher porosity, tunable surface charge properties, improved salt rejection, and higher thermal stability. It is also understood that the membranes have other properties.

In various aspects, the membrane can have a contact angle of less than about 70°. In a further aspect, the membrane can have a contact angle of less than about 60°. In a still further aspect, the membrane can have a contact angle of less than about 50°. In yet a further aspect, the membrane can have a contact angle of less than about 40°. Such membrane will have a high resistance of fouling.

In various aspects, the membrane exhibits a salt rejection of at least about 60%. In a further aspect, the membrane exhibits a salt rejection of at least about 70%. In a still further aspect, the membrane exhibits a salt rejection of at least about 80%. In yet a further aspect, the membrane exhibits a salt rejection of at least about 90%.

In various aspects, the membrane exhibits a salt rejection of at least about 90% for at least about 1 hour. In a further aspect, the membrane exhibits a salt rejection of at least about 90% for at least about 2 hours. In a still further aspect, the membrane exhibits a salt rejection of at least about 90% for at least about 3 hours. In yet a further aspect, the membrane exhibits a salt rejection of at least about 90% for at least about 4 hours.

In a further aspect, the membrane exhibits an improvement in at least one property selected from resistance to fouling, hydropholicity, surface charge, salt rejection, and roughness. In a still further aspect, the membrane demonstrates an improvement in at least one property selected from resistance to fouling, salt rejection, and hydrophilicity. In yet a further aspect, the membrane demonstrates an improvement in resistance to fouling. In an even further aspect, the membrane demonstrates an improvement in hydrophilicity. In a still further aspect, the membrane demonstrates an improvement in surface charge. In yet a further aspect, the membrane demonstrates an improvement in roughness. In an even further aspect, the membrane demonstrates an improvement in salt rejection.

C. Compounds

In one aspect, the invention relates to residues of compounds useful for modifying thin-film membranes comprising a surface. In a further aspect, the residue of a compound comprises an anti-microbial agent. Examples of anti-microbial agents include, but are not limited to, quaternary ammonium salts and tertiary amines.

In one aspect, the invention relates to compounds useful for modifying thin-film membranes comprising a surface.

In various aspects, the compound comprises an azide functionality. In a further aspect, the compound comprises a perfluorophenyl azide functionality. Without wishing to be bound by theory, perfluorophenyl azides can react with a variety of substrates upon exposure to irradiation (Scheme I).

SCHEME I.

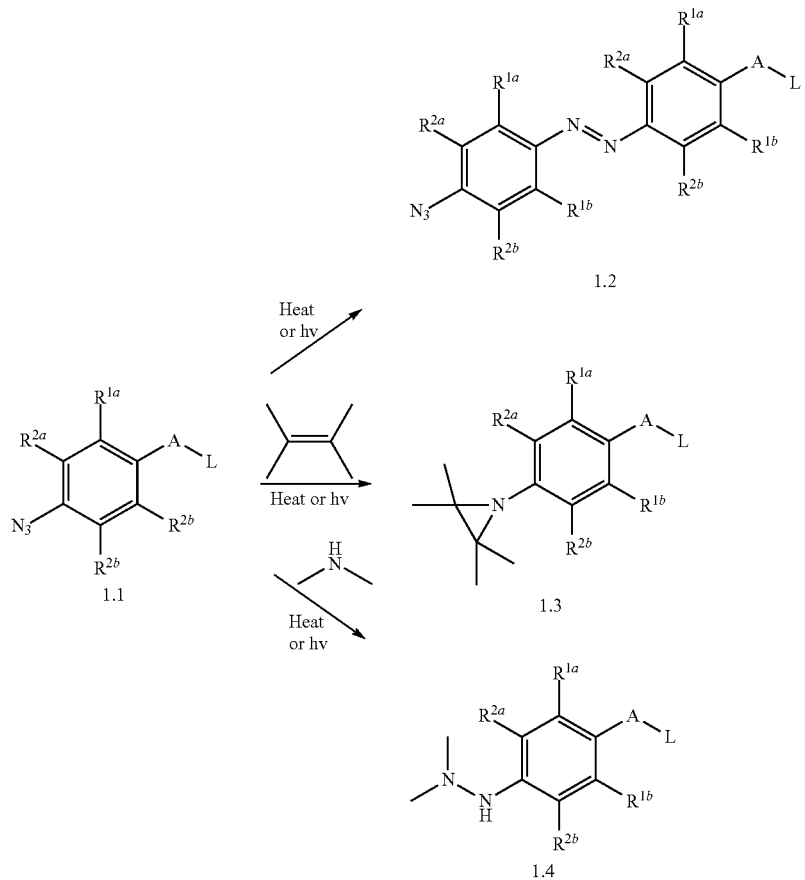

Thus, in various aspects, the residue of a compound can be bonded with the surface of the thin-film membrane. Bonding can include, for example, coating the surface with the residue of a compound. In a further aspect, coating comprises spray coating. In a still further aspect, coating comprises dip-coating (Scheme II).

SCHEME II.

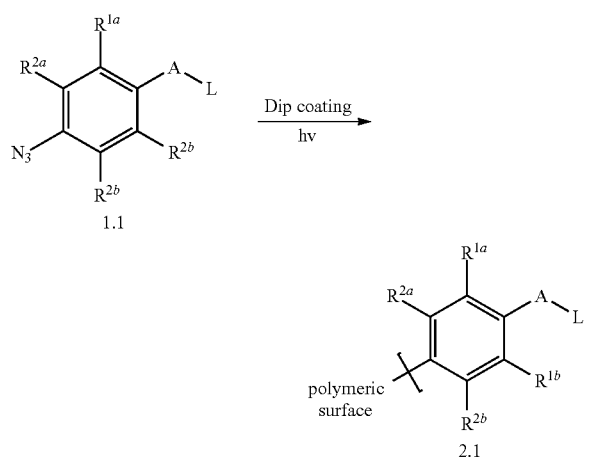

In a further aspect, bonding comprises exposing the membrane to a heat source. In a still further aspect, the heat source comprises a stream of hot air, an oven, or an IR lamp. In yet a further aspect, the temperature of the heat source is at least about 100° C.

In a further aspect, bonding comprises exposing the membrane to a light source. In a still further aspect, the light source comprises UV light. In yet a further aspect, the light source comprises UV light in the range of from between 200 nm and 370 nm. In an even further aspect, bonding comprises coating the polymeric surface with the at least one residue of a compound and exposing the surface to a light source.

In a further aspect, bonding comprises a covalent modification. In a still further aspect, bonding comprises a photochemical modification.

In various aspects, the residue of a compound comprises a radical species. In a further aspect, the radical species is a singlet nitrene. In a still further aspect, the residue of a compound can be bonded with the surface, wherein bonding comprises singlet nitrene insertion.

1. Structure

In one aspect, the invention relates to at least one residue of a compound having a structure represented by a formula:

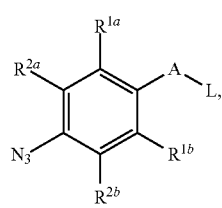

wherein A is selected from —C(=O)— and —(SO$_2$)—; wherein L is selected from —OQ, —O$^-$, —N$^+$R$^3$HQ and —NR$^3$Q; wherein Q is selected from hydrogen, a hydrophilic polymer, and a structure represented by a formula:

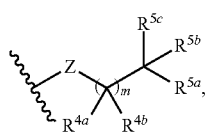

wherein Z is selected from —CR$^{6a}$R$^{6b}$—, —C(=O)—, —C(=NH)—, and —C(=NH)NR$^7$—; wherein m is an integer selected from 0, 1, 2, 3, 4, 5, 6, 7, and 8; wherein each of R$^{1a}$ and R$^{1b}$ is independently selected hydrogen and halogen; wherein each of R$^{2a}$ and R$^{2b}$ is halogen; wherein R$^3$, when present, is selected from hydrogen and C1-C4 alkyl; wherein each of R$^{4a}$ and R$^{4b}$, when present, is independently selected from hydrogen, halogen, —CN, —OH, —NR$^{8a}$R$^{8b}$, —NR$^{8a}$R$^{8b}$ H$^+$, C1-C4 alkyl, C1-C4 monohaloalkyl, C1-C4 polyhaloalkyl, —SO$_3^-$, —SO$_3$R$^9$, —CO$_2^-$, and —CO$_2$R$^9$; wherein each of R$^{5a}$, R$^{5b}$, and R$^{5c}$ is independently selected from hydrogen, halogen, —CN, —OH, —NR$^{10a}$R$^{10b}$, —NR$^{10a}$R$^{10b}$, H$^+$, C1-C4 alkyl, C1-C4 monohaloalkyl, C1-C4 polyhaloalkyl, —SO$_3^-$, —SO$_3$R$^{11}$, —CO$_2^-$, and —CO$_2$R$^{11}$; wherein each of R$^{6a}$ and R$^{6b}$, when present, is independently selected hydrogen, halogen, —CN, —OH, —NR$^{12a}$R$^{12b}$, —NR$^{12a}$R$^{12b}$ H$^+$, C1-C4 alkyl, C1-C4 monohaloalkyl, C1-C4 polyhaloalkyl, —SO$_3^-$, —SO$_3$R$^{13}$, —CO$_2^-$, and —CO$_2$R$^{13}$; wherein R$^7$, when present, is selected from hydrogen and C1-C4 alkyl; wherein each of R$^{8a}$ and R$^{8b}$, when present, is independently selected from hydrogen and C1-C4 alkyl; wherein R$^9$, when present, is selected from hydrogen and C1-C4 alkyl; wherein each of R$^{10a}$ and R$^{10b}$, when present, is independently selected from hydrogen and C1-C4 alkyl; wherein R$^{11}$, when present, is selected from hydrogen and C1-C4 alkyl; wherein each of R$^{12a}$ and R$^{12b}$, when present, is independently selected from hydrogen and C1-C4 alkyl; and wherein R$^{13}$, when present, is selected from hydrogen and C1-C4 alkyl.

In a further aspect, the residue of a compound has a structure selected from:

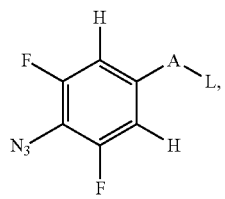 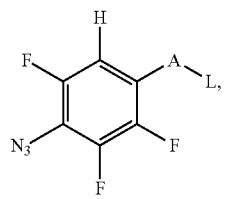

-continued

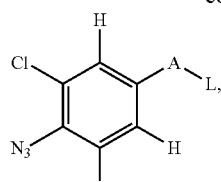 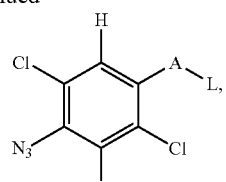

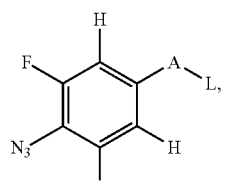 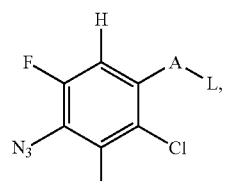

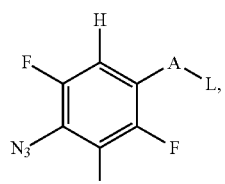 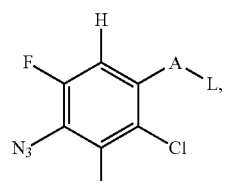

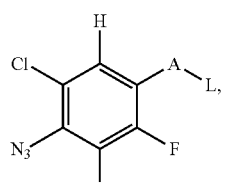 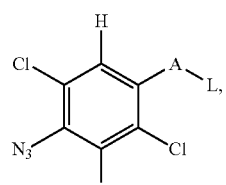

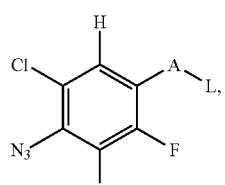 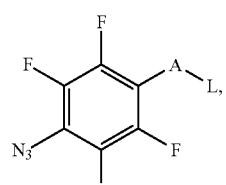

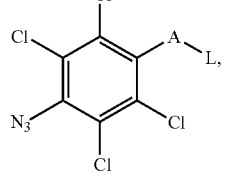 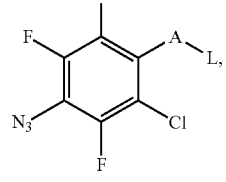

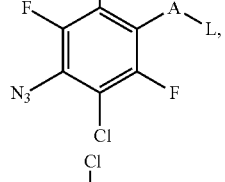 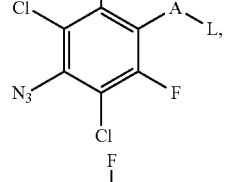

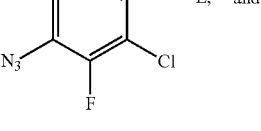 and 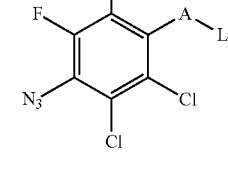

In a still further aspect, the residue of a compound has a structure represented by a formula:

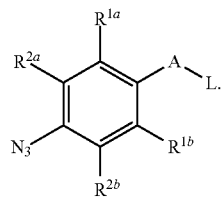

In a further aspect, the residue of a compound has a structure selected from:

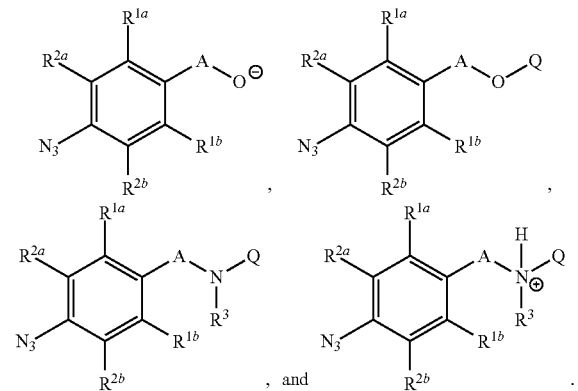

In a still further aspect, the residue of a compound has a structure represented by a formula:

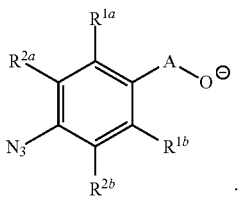

In yet a further aspect, the residue of a compound has a structure selected from:

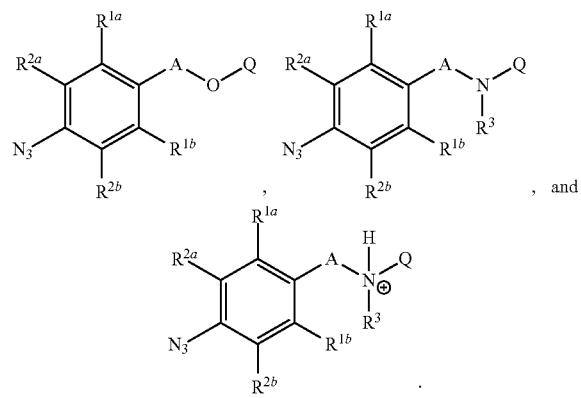

In an even further aspect, the residue of a compound has a structure selected from:

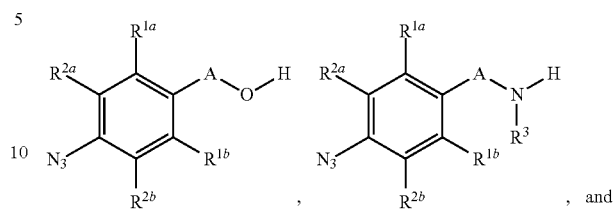

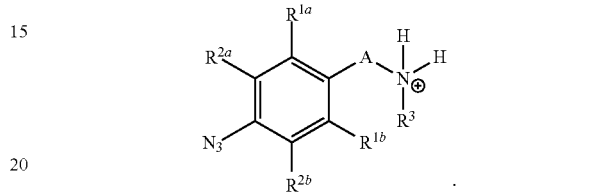

In a further aspect, the residue of a compound has a structure selected from:

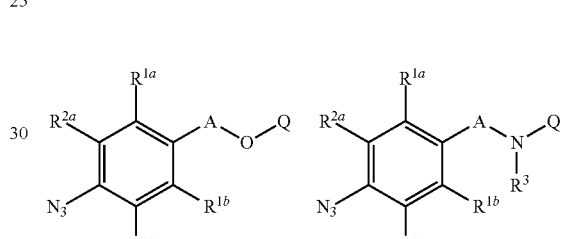

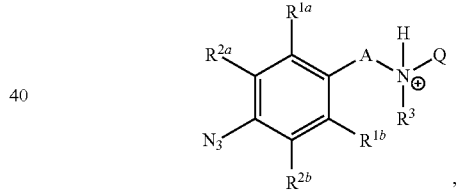

wherein Q is a hydrophilic polymer.

In a further aspect, the residue of a compound has a structure selected from:

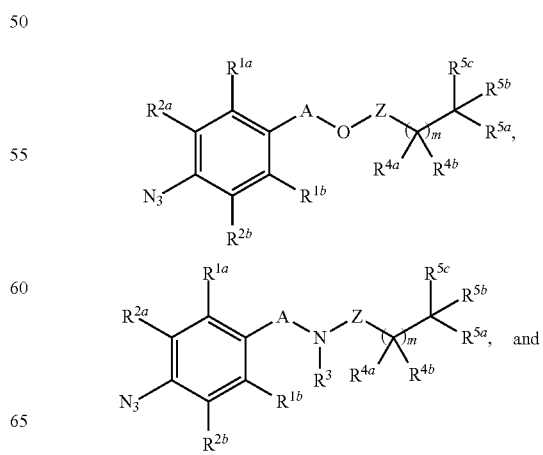

-continued

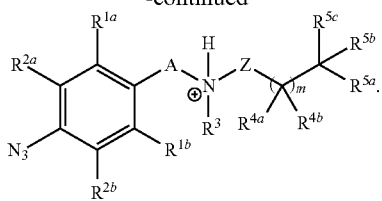

In one aspect, the invention relates to a compound having a structure represented by a formula:

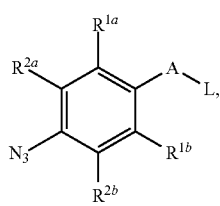

wherein m is an integer selected from 0, 1, 2, 3, 4, 5, 6, 7, and 8; wherein A is selected from —C(=O)— and —(SO$_2$)— and L is —OQ, or wherein A is —(SO$_2$)— and L is selected from —OQ and —NR$^3$Q; wherein Q is selected from hydrogen, a hydrophilic polymer, and a structure represented by a formula:

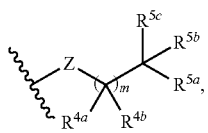

wherein Z is selected from —CR$^{6a}$R$^{6b}$—, —C(=O)—, —C(=NH)—, and —C(=NH)NR$^7$—; wherein each of R$^{1a}$ and R$^{1b}$ is independently selected hydrogen and halogen; wherein each of R$^{2a}$ and R$^{2b}$ is halogen; wherein R$^3$, when present, is selected from hydrogen and C1-C4 alkyl; wherein each of R$^{4a}$ and R$^{4b}$, when present, is independently selected from hydrogen, halogen, —CN, —OH, —NR$^{8a}$R$^{8b}$, —NR$^{8a}$R$^{8b}$ H$^+$, C1-C4 alkyl, C1-C4 monohaloalkyl, C1-C4 polyhaloalkyl, —SO$_3^-$, —SO$_3$R$^9$, —CO$_2^-$, and —CO$_2$R$^9$; wherein each of R$^{5a}$, R$^{5b}$, and R$^{5c}$ is independently selected from hydrogen, halogen, —CN, —OH, —NR$^{10a}$R$^{10b}$, —NR$^{10a}$R$^{10b}$ H$^+$, C1-C4 alkyl, C1-C4 monohaloalkyl, C1-C4 polyhaloalkyl, —SO$_3^-$, —SO$_3$R$^{11}$, —CO$_2^-$, and —CO$_2$R$^{11}$; wherein each of R$^{6a}$ and R$^{6b}$, when present, is independently selected hydrogen, halogen, —CN, —OH, —NR$^{12a}$R$^{12b}$, —NR$^{12a}$R$^{12b}$ H$^+$, C1-C4 alkyl, C1-C4 monohaloalkyl, C1-C4 polyhaloalkyl, —SO$_3^-$, —SO$_3$R$^{13}$, —CO$_2^-$, and —CO$_2$R$^{13}$; wherein R$^7$, when present, is selected from hydrogen and C1-C4 alkyl; wherein each of R$^{8a}$ and R$^{8b}$, when present, is independently selected from hydrogen and C1-C4 alkyl; wherein R$^9$, when present, is selected from hydrogen and C1-C4 alkyl; wherein each of R$^{10a}$ and R$^{10b}$, when present, is independently selected from hydrogen and C1-C4 alkyl; wherein R$^{11}$, when present, is selected from hydrogen and C1-C4 alkyl; wherein each of R$^{12a}$ and R$^{12b}$, when present, is independently selected from hydrogen and C1-C4 alkyl; and wherein R$^{13}$, when present, is selected from hydrogen and C1-C4 alkyl.

In yet a further aspect, the residue of a compound has a structure selected from:

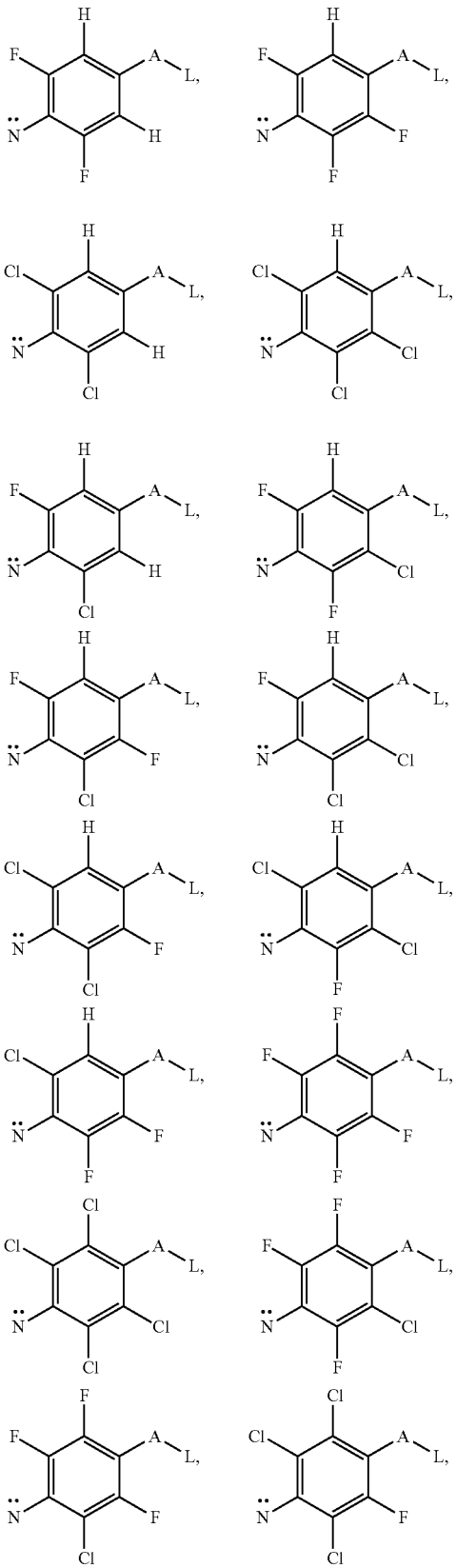

-continued

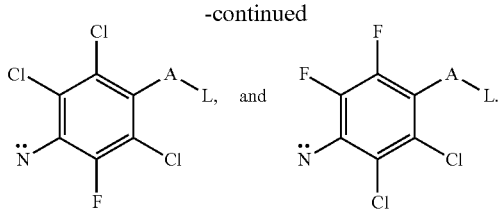

In an even further aspect, the residue of a compound has a structure represented by a formula:

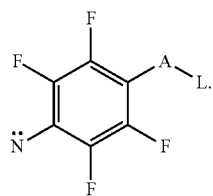

In one aspect, the invention relates to a compound having a structure represented by a formula:

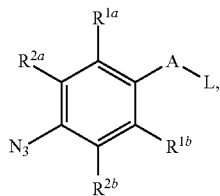

wherein m is an integer selected from 0, 1, 2, 3, 4, 5, 6, 7, and 8; wherein A is selected from —C(=O)— and —(SO$_2$)— and L is —OQ, or wherein A is —(SO$_2$)— and L is selected from —OQ and —NR$^3$Q; wherein Q is selected from hydrogen, a hydrophilic polymer, and a structure represented by a formula:

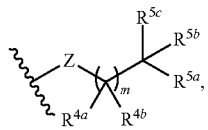

wherein Z is selected from —CR$^{6a}$R$^{6b}$—, —C(=O)—, —C(=NH)—, and —C(=NH)NR$^7$—; wherein each of R$^{1a}$ and R$^{1b}$ is independently selected hydrogen and halogen; wherein each of R$^{2a}$ and R$^{2b}$ is halogen; wherein R$^3$, when present, is selected from hydrogen and C1-C4 alkyl; wherein each of R$^{4a}$ and R$^{4b}$, when present, is independently selected from hydrogen, halogen, —CN, —OH, —NR$^{8a}$R$^{8b}$, —NR$^{8a}$R$^{8b}$ H$^+$, C1-C4 alkyl, C1-C4 monohaloalkyl, C1-C4 polyhaloalkyl, —SO$_3^-$, —SO$_3$R$^9$, —CO$_2^-$, and —CO$_2$R$^9$; wherein each of R$^{5a}$, R$^{5b}$, and R$^{5c}$ is independently selected from hydrogen, halogen, —CN, —OH, —NR$^{10a}$R$^{10b}$, —NR$^{10a}$R$^{10b}$ H$^+$, C1-C4 alkyl, C1-C4 monohaloalkyl, C1-C4 polyhaloalkyl, —SO$_3^-$, —SO$_3$R$^{11}$, —CO$_2^-$, and —CO$_2$R$^{11}$; wherein each of R$^{6a}$ and R$^{6b}$, when present, is independently selected hydrogen, halogen, —CN, —OH, —NR$^{12a}$R$^{12b}$, —NR$^{12a}$R$^{12b}$ H$^+$, C1-C4 alkyl, C1-C4 monohaloalkyl, C1-C4 polyhaloalkyl, —SO$_3^-$, —SO$_3$R$^{13}$, —CO$_2^-$, and —CO$_2$R$^{13}$; wherein R$^7$, when present, is selected from hydrogen and C1-C4 alkyl; wherein each of R$^{8a}$ and R$^{8b}$, when present, is independently selected from hydrogen and C1-C4 alkyl; wherein R$^9$, when present, is selected from hydrogen and C1-C4 alkyl; wherein each of R$^{10a}$ and R$^{10b}$, when present, is independently selected from hydrogen and C1-C4 alkyl; wherein R$^{11}$, when present, is selected from hydrogen and C1-C4 alkyl; wherein each of R$^{12a}$ and R$^{12b}$, when present, is independently selected from hydrogen and C1-C4 alkyl; and wherein R$^{13}$, when present, is selected from hydrogen and C1-C4 alkyl.

In a further aspect, a compound has a structure selected from:

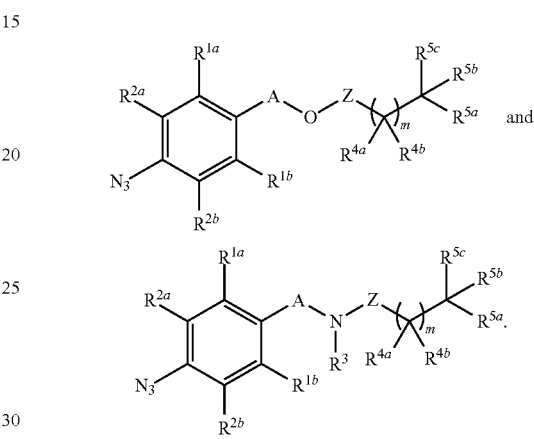

In a still further aspect, a compound has a structure represented by a formula:

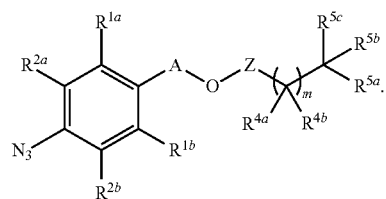

In yet a further aspect, a compound has a structure selected from:

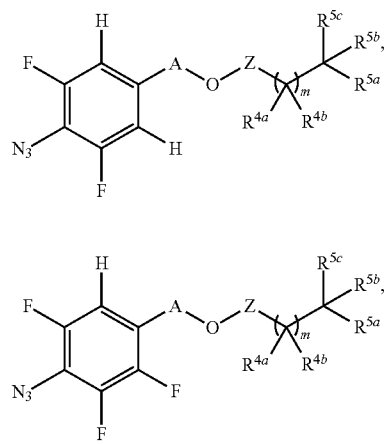

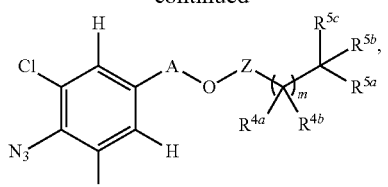
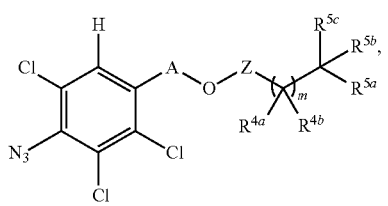
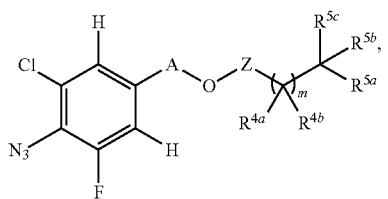
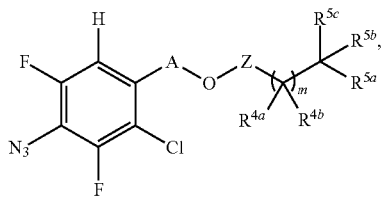
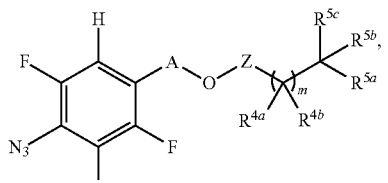
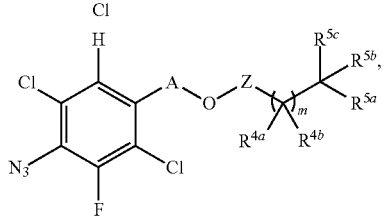
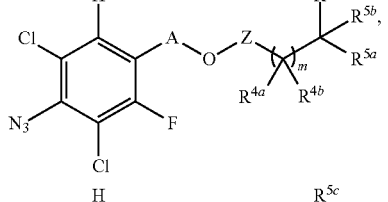
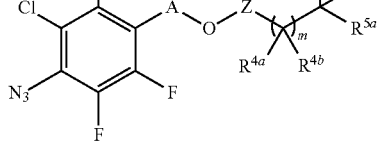
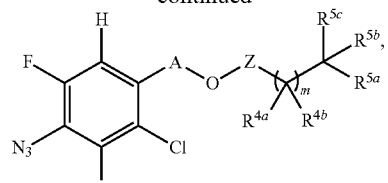
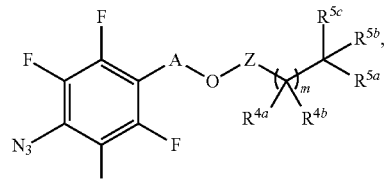
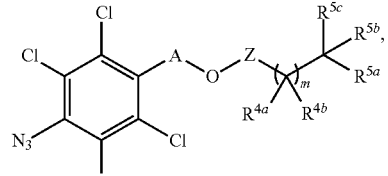
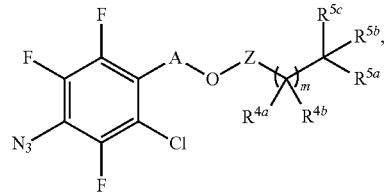
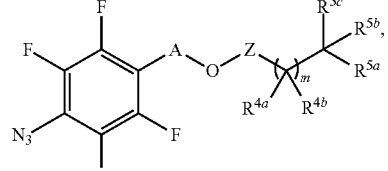
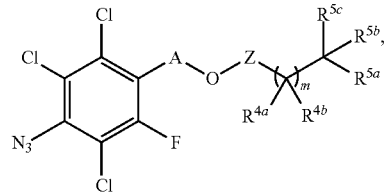
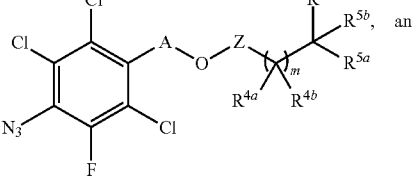
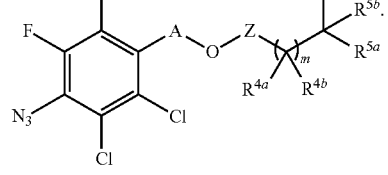

In an even further aspect, a compound has a structure represented by a formula:
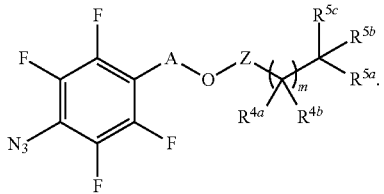
In a further aspect, a compound has a structure represented by a formula:
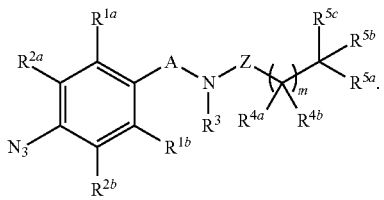
In a still further aspect, a compound has a structure selected from:
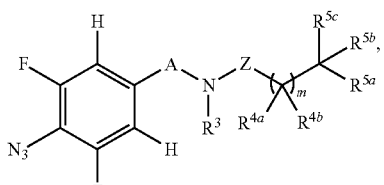
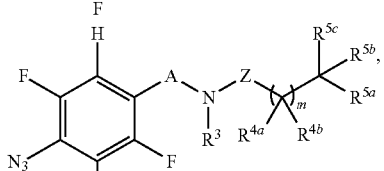
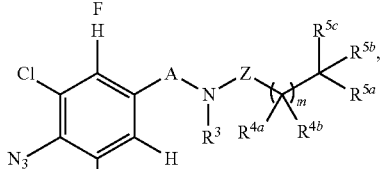
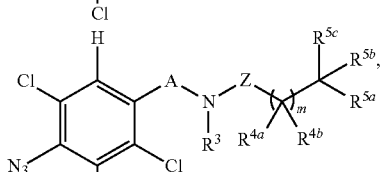
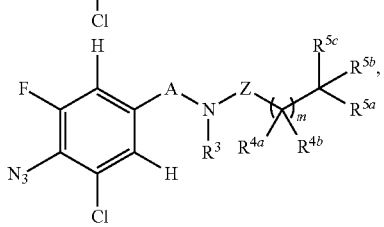
-continued
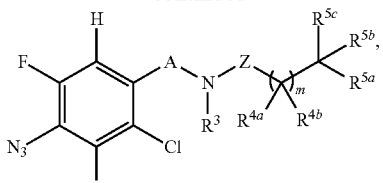
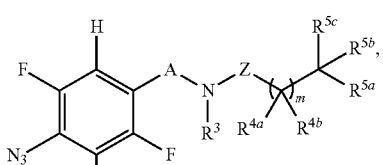
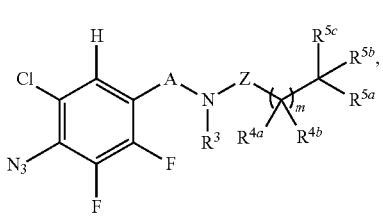
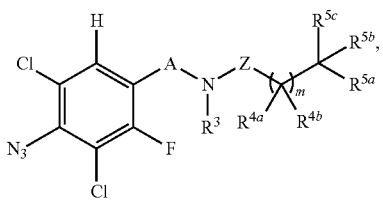
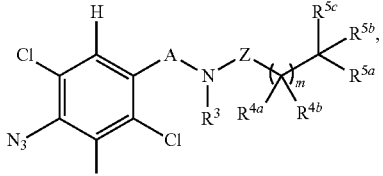
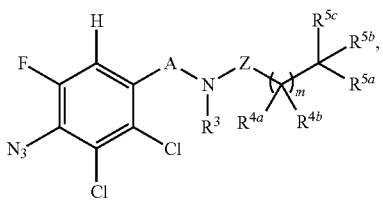
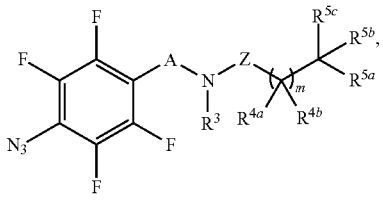
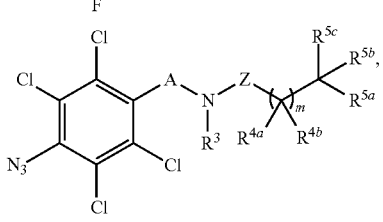

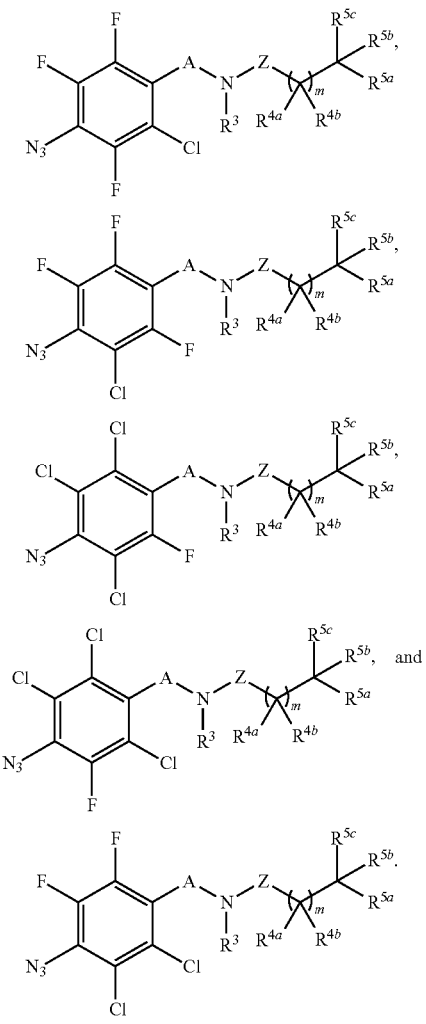
In yet a further aspect, a compound has a structure represented by a formula:
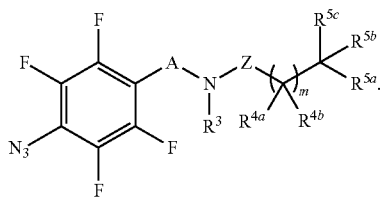
In a further aspect, a compound has a structure selected from:
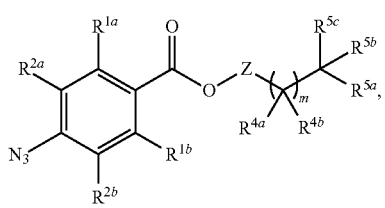
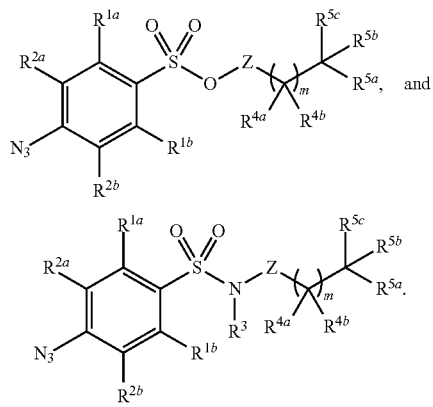
In a still further aspect, a compound has a structure selected from:
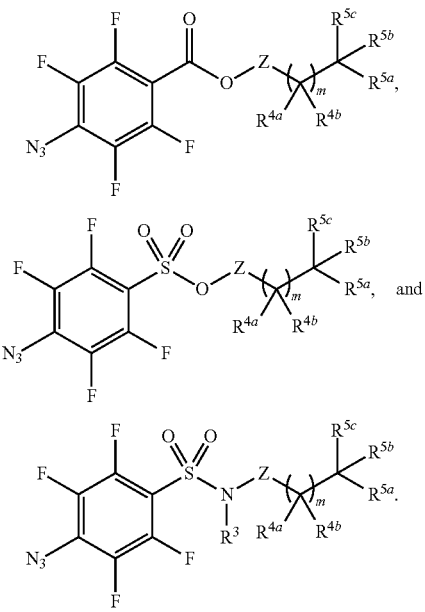
In a further aspect, a compound has a structure selected from:
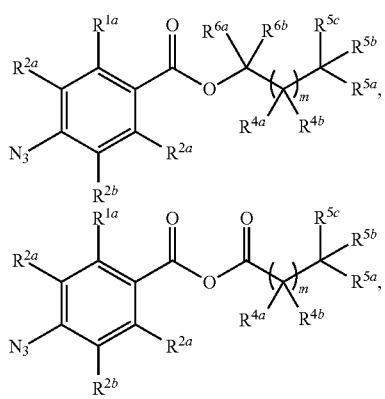

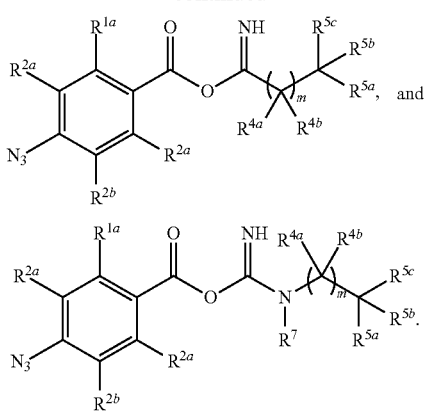
In a still further aspect, a compound has a structure selected from:
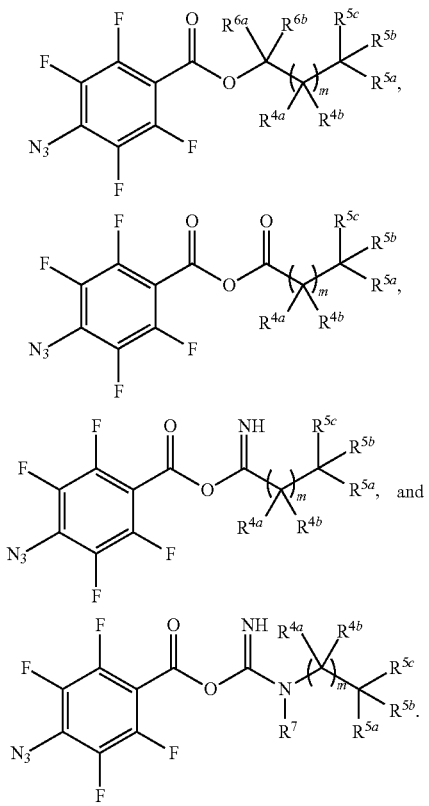
In a further aspect, a compound has a structure selected from:
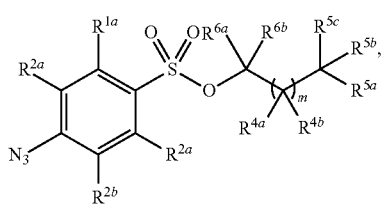
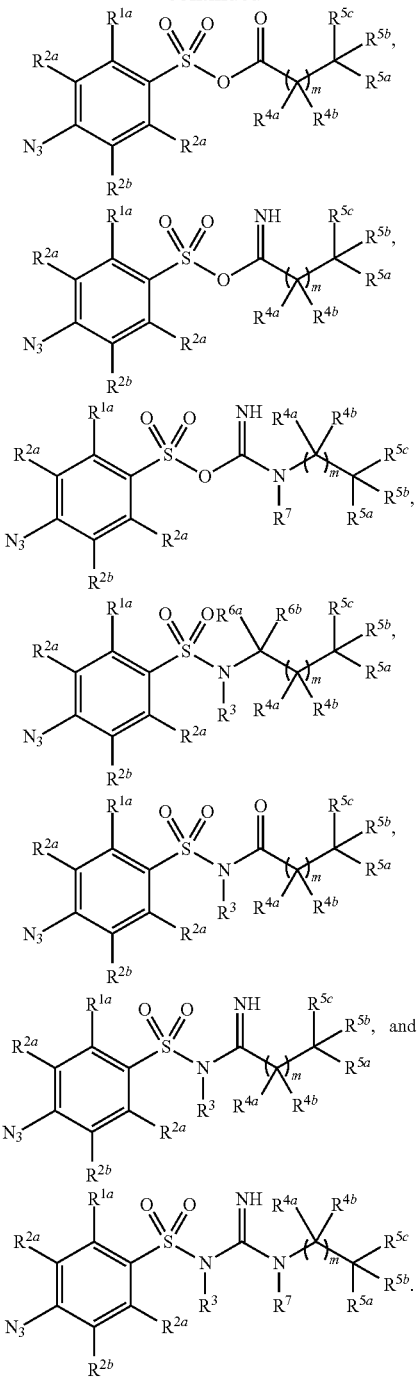
In a still further aspect, a compound has a structure selected from:
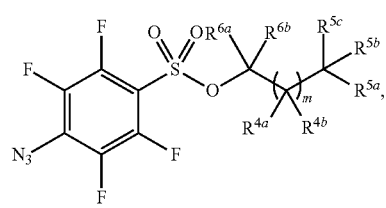

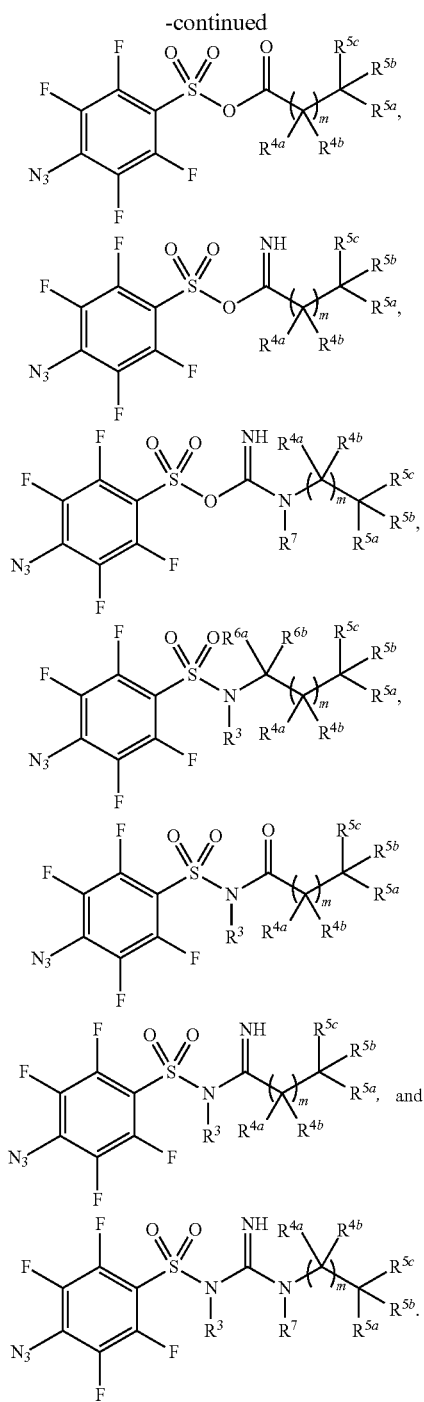
In a further aspect, the compound has a structure selected from:
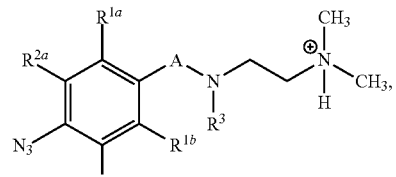
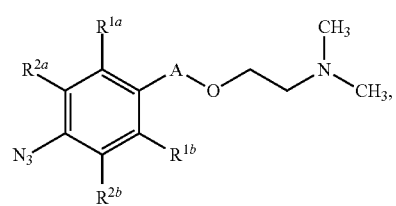
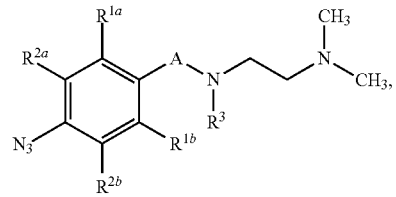
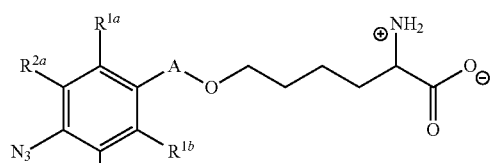
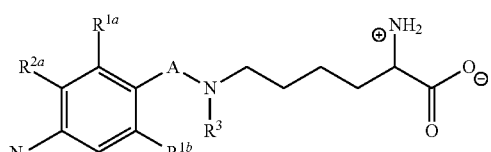
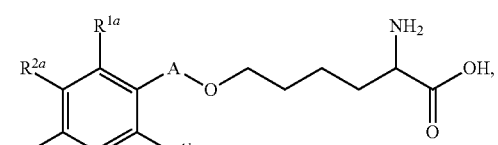
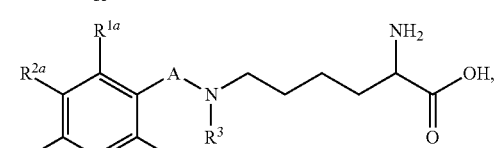
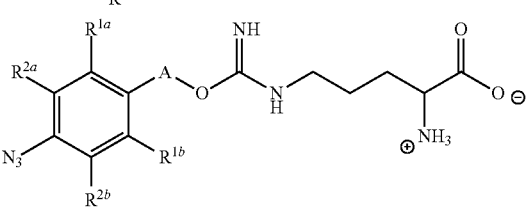

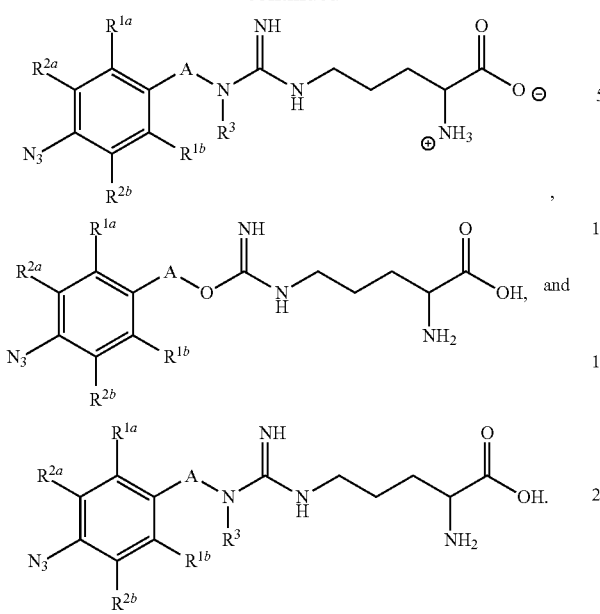
In a still further aspect, the compound has a structure selected from:
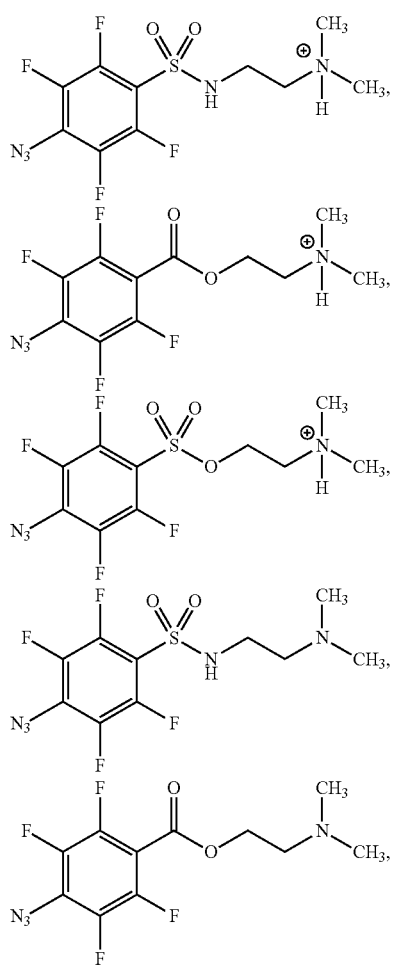
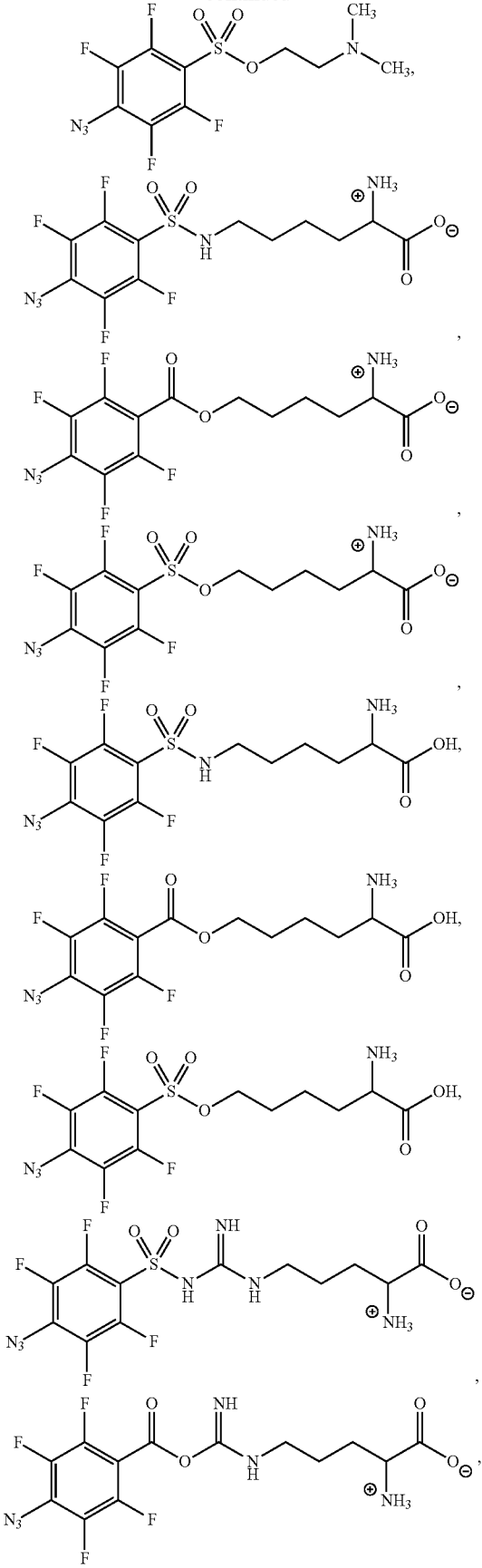

-continued

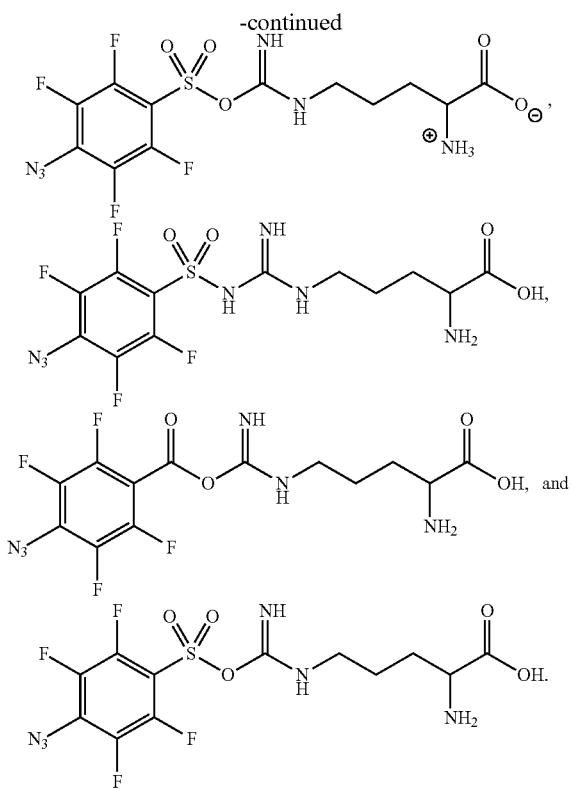

In yet a further aspect, the compound has a structure selected from:

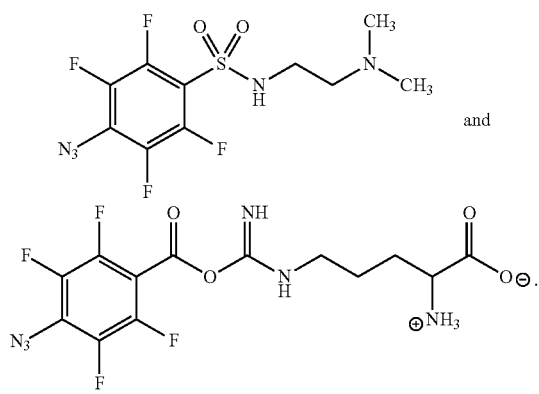

a. M

In one aspect, m is an integer selected from 0, 1, 2, 3, 4, 5, 6, 7, and 8. In a further aspect, m is an integer selected from 0, 1, 2, 3, 4, 5, 6, and 7. In a still further aspect, m is an integer selected from 0, 1, 2, 3, 4, 5, and 6. In yet a further aspect, m is an integer selected from 0, 1, 2, 3, 4, and 5. In an even further aspect, m is an integer selected from 0, 1, 2, 3, and 4. In a still further aspect, m is an integer selected from 0, 1, 2, and 3. In yet a further aspect, m is an integer selected from 0, 1, and 2. In an even further aspect, m is an integer selected from 0 and 1. In a still further aspect, m is 0. In yet a further aspect, m is 1. In an even further aspect, m is 2. In a still further aspect, m is 3. In yet a further aspect, m is 4. In an even further aspect, m is 5. In a still further aspect, m is 6. In yet a further aspect, m is 6. In an even further aspect, m is 7. In a still further aspect, m is 8.

b. A and L Groups

In one aspect, A is selected from —C(=O)— and —(SO$_2$)—. In a further aspect, A is —C(=O)—. In a still further aspect, A is —(SO$_2$)—.

In one aspect, L is selected from —OQ, —O$^-$, —N$^+$R$^3$HQ and —NR$^3$Q. In a further aspect, L is selected from —OQ, —O—, and —N$^+$R$^2$HQ. In a still further aspect, L is selected from —OQ, and —O$^-$. In yet a further aspect, L is —OQ. In an even further aspect, L is —O$^-$. In a still further aspect, L is —N$^+$R$^3$HQ. In yet a further aspect, L is —NR$^3$Q.

In one aspect, A is selected from —C(=O)— and —(SO$_2$)— and L is —OQ. In a further aspect, A is —C(=O)— and L is —OQ. In a still further aspect, A is —(SO$_2$)— and L is —OQ.

In one aspect, A is —(SO$_2$)— and L is selected from —OQ and —NR$^3$Q. In a further aspect, A is —(SO$_2$)— and L is —OQ. In a still further aspect, A is —(SO$_2$)— and L is —NR$^3$Q.

c. Q Groups

In one aspect, Q is selected from hydrogen, a hydrophilic polymer, and a structure represented by a formula:

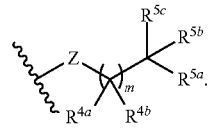

In a further aspect, Q is hydrogen.

In a further aspect, Q is a hydrophilic polymer. In a still further aspect, the hydrophilic polymer comprises at least one moiety selected from poly(ethylene glycol), poly(ethyleneimine) and polyaniline, or a mixture thereof. In yet a further aspect, the hydrophilic polymer comprises at least one moiety selected from poly(ethylene glycol) and polyaniline, or a mixture thereof. In an even further aspect, the hydrophilic polymer is poly(ethylene glycol). In a still further aspect, the hydrophilic polymer is poly(ethyleneimine). In yet a further aspect, the hydrophilic polymer is polyaniline.

In a further aspect, Q has a structure represented by a formula:

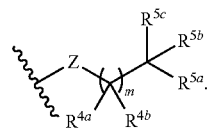

In a still further aspect, Q has a structure selected from:

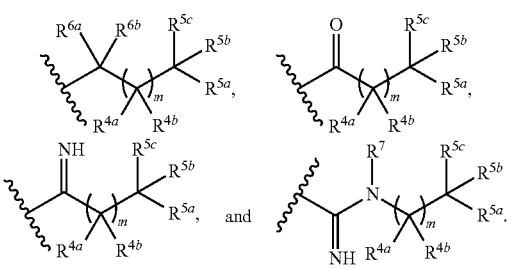

In yet a further aspect, Q has a structure selected from:

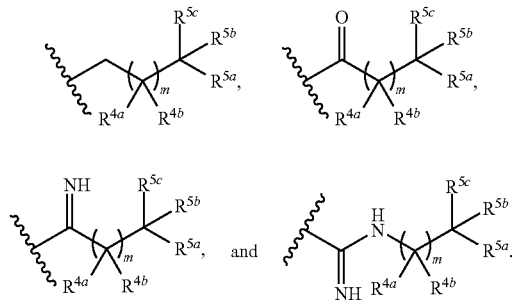

In an even further aspect, Q has a structure represented by a formula:

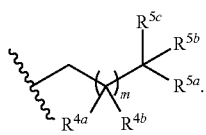

In a still further aspect, Q has a structure selected from:

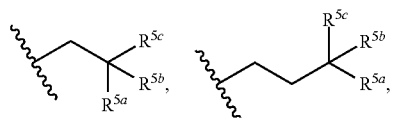

In yet a further aspect, Q has a structure selected from:

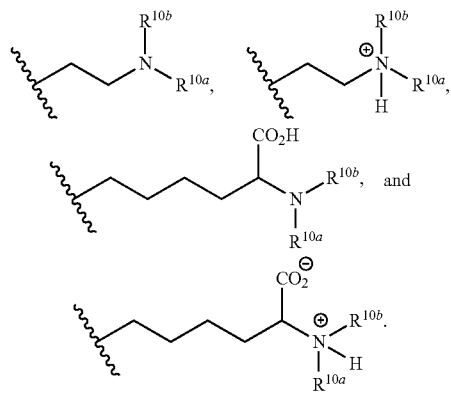

In an even further aspect, Q has a structure selected from:

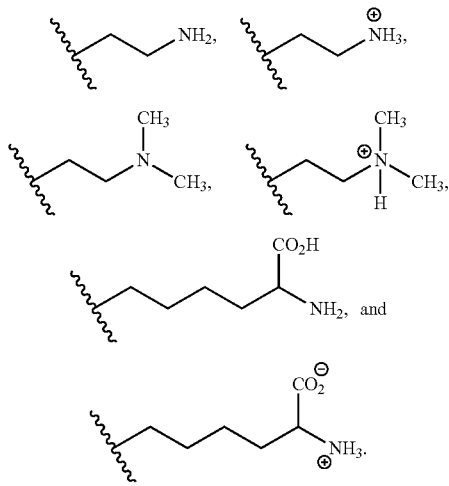

In a further aspect, Q has a structure represented by a formula:

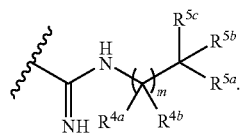

In a still further aspect, Q has a structure selected from:

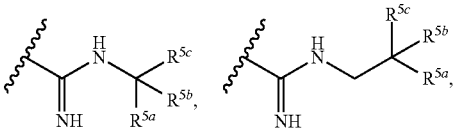

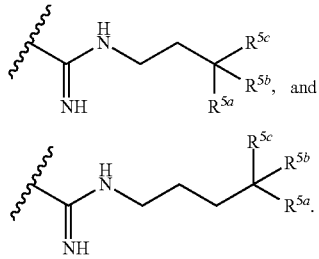

In yet a further aspect, Q has a structure selected from:

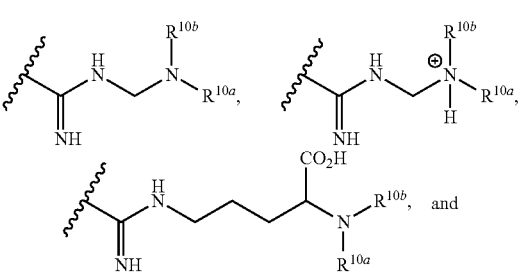

-continued

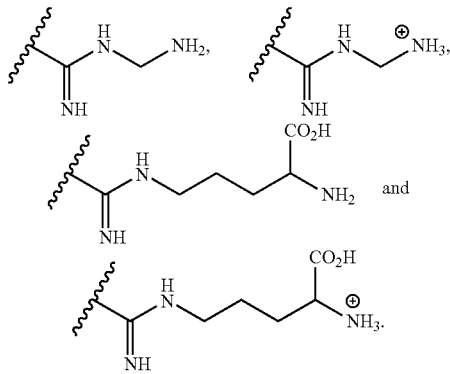

In an even further aspect, Q has a structure selected from:

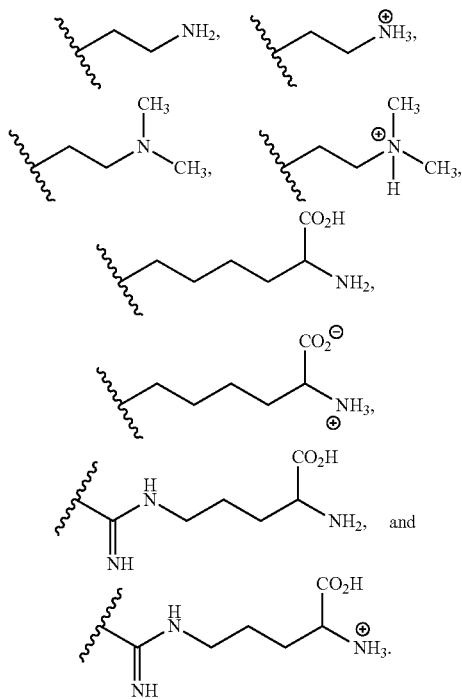

In a further aspect, Q has a structure selected from:

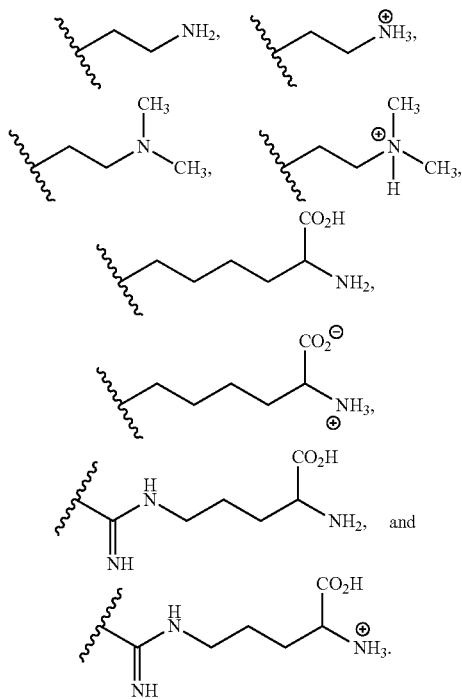

d. Z Groups

In a further aspect, Z is selected from —$CR^{6a}R^{6b}$—, —C(=O)—, —C(=NH)—, and —C(=NH)$NR^7$—. In a further aspect, Z is selected from —$CR^{6a}R^{6b}$—, —C(=O)—, and —C(=NH)—. In a still further aspect, Z is selected from —$CR^{6a}R^{6b}$— and —C(=O)—. In yet a further aspect, Z is —$CR^{6a}R^{6b}$—. In an even further aspect, Z is —C(=O)—. In a still further aspect, Z is —C(=NH)—. In yet a further aspect, Z is —C(=NH)$NR^7$—.

e. $R^{1A}$ and $R^{1B}$ Groups

In one aspect, each of $R^{1a}$ and $R^{1b}$ is independently selected from hydrogen and halogen. In a further aspect, each of $R^{1a}$ and $R^{1b}$ is hydrogen.

In a further aspect, each of $R^{1a}$ and $R^{1b}$ is halogen. In a still further aspect, each of $R^{1a}$ and $R^{1b}$ is independently selected from —Cl and —F. In yet a further aspect, each of $R^{1a}$ and $R^{1b}$ is —Cl. In an even further aspect, each of $R^{1a}$ and $R^{1b}$ is —F. In a still further aspect, $R^{1a}$ is —Cl and Rib is —F.

In a further aspect, $R^{1b}$ is hydrogen and $R^{1a}$ is halogen. In a still further aspect, $R^{1b}$ is hydrogen and $R^{1a}$ is selected from —Cl and —F. In yet a further aspect, $R^{1b}$ is hydrogen and $R^{1a}$ is —Cl. In an even further aspect, $R^{1b}$ is hydrogen and $R^{1a}$ is —F.

f. $R^{2A}$ and $R^{2B}$ Groups

In one aspect, each of $R^{2a}$ and $R^{2b}$ is halogen. In a further aspect, each of $R^{2a}$ and $R^{2b}$ is independently selected from —Cl and —F. In a still further aspect, each of $R^{2a}$ and $R^{2b}$ is —Cl. In yet a further aspect, each of $R^{2a}$ and $R^{2b}$ is —F. In an even further aspect, $R^{2a}$ is —Cl and $R^{2b}$ is —F.

g. $R^3$ Groups

In one aspect, $R^3$, when present, is selected from hydrogen and C1-C4 alkyl. In a further aspect, $R^3$, when present, is selected from hydrogen, methyl, ethyl, and propyl. In a still further aspect, $R^3$, when present, is selected from hydrogen, methyl, and ethyl. In yet a further aspect, $R^3$, when present, is selected from hydrogen and methyl. In an even further aspect, $R^3$, when present, is hydrogen.

h. $R^{4A}$ and $R^{4B}$ Groups

In one aspect, each of $R^{4a}$ and $R^{4b}$, when present, is independently selected from hydrogen, halogen, —CN, —OH, —$NR^{8a}R^{8b}$, —$NR^{8a}R^{8b}$ H$^+$, C1-C4 alkyl, C1-C4 monohaloalkyl, C1-C4 polyhaloalkyl, —$SO_3^-$, —$SO_3R^9$, —$CO_2^-$, and —$CO_2R^9$. In a further aspect, each of $R^{4a}$ and $R^{4b}$, when present, is independently selected from hydrogen, —F, —Cl, —CN, —OH, —$NR^{8a}R^{8b}$, —$NR^{8a}R^{8b}$H$^+$, methyl, ethyl, propyl, —$CH_2F$, —$CH_2Cl$, —$CH_2CH_2F$, —$CH_2CH_2Cl$, —$CH_2CH_2CH_2F$, —$CH_2CH_2CH_2Cl$, —$CHF_2$, —$CF_3$, —$CHCl_2$, —$CCl_3$, —$SO_3^-$, —$SO_3R^9$, —$CO_2^-$, and —$CO_2R^9$. In a still further aspect, each of $R^{4a}$ and $R^{4b}$, when present, is independently selected from hydrogen, —F, —Cl, —CN, —OH, —$NR^{8a}R^{8b}$, —$NR^{8a}R^{8b}$H$^+$, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$SO_3^-$, —$SO_3R^9$, —$CO_2^-$, and —$CO_2R^9$. In yet a further aspect, each of $R^{4a}$ and $R^{4b}$, when present, is independently selected from hydrogen, —F, —Cl, —CN, —OH, —$NR^{8a}R^{8b}$, —$NR^{8a}R^{8b}$H$^+$, methyl, —$CH_2F$, —$CH_2Cl$, —$CHF_2$, —$CF_3$, —$CHCl_2$, —$CCl_3$, —$SO_3^-$, —$SO_3R^9$, —$CO_2^-$, and —$CO_2R^9$. In an even further aspect, each of $R^{4a}$ and $R^{4b}$, when present, is independently selected from hydrogen, —F, —Cl, —CN, —OH, —$NH_2$, —$NH_3^+$, —$CF_3$, —$CCl_3$, —$SO_3^-$, —$SO_3R^9$, —$CO_2^-$, and —$CO_2R^9$.

In a further aspect, each of $R^{4a}$ and $R^{4b}$, when present, is independently selected from halogen, —CN, —OH, —$NR^{8a}R^{8b}$, —$NR^{8a}R^{8b}$H$^+$, C1-C4 alkyl, C1-C4 monohaloalkyl, C1-C4 polyhaloalkyl, —$SO_3^-$, —$SO_3R^9$, —$CO_2^-$, and —$CO_2R^9$. In a still further aspect, each of $R^{4a}$ and $R^{4b}$, when present, is independently selected from —F, —Cl, —CN, —OH, —$NR^{8a}R^{8b}$, —$NR^{8a}R^{8b}$H$^+$, methyl, ethyl, propyl, —$CH_2F$, —$CH_2Cl$, —$CH_2CH_2F$, —$CH_2CH_2Cl$, —$CH_2CH_2CH_2F$, —$CH_2CH_2CH_2Cl$, —$CHF_2$, —$CF_3$, —$CHCl_2$, —$CCl_3$, —$SO_3^-$, —$SO_3R^9$, —$CO_2^-$, and —$CO_2R^9$. In yet a further aspect, each of $R^{4a}$ and $R^{4b}$, when present, is independently selected from —F, —Cl, —CN, —OH, —$NR^{8a}R^{8b}$, —$NR^{8a}R^{8b}$H$^+$, methyl, ethyl, —$CH_2F$, —$CH_2Cl$, —$CH_2CH_2F$, —$CH_2CH_2Cl$, —$CHF_2$, —$CF_3$, —CHCl$_2$, —CCl$_3$, —SO$_3^-$, —SO$_3$R$^9$, —CO$_2^-$, and —CO$_2$R$^9$. In an even further aspect, each of R$^{4a}$ and R$^{4b}$, when present, is independently selected from —F, —Cl, —CN, —OH, —NR$^{8a}$R$^{8b}$, —NR$^{8a}$R$^{8b}$H$^+$, methyl, —CH$_2$F, —CH$_2$Cl, —CHF$_2$, —CF$_3$, —CHCl$_2$, —CCl$_3$, —SO$_3^-$, —SO$_3$R$^9$, —CO$_2^-$, and —CO$_2$R$^9$. In a still further aspect, each of R$^{4a}$ and R$^{4b}$, when present, is independently selected from —F, —Cl, —CN, —OH, —NR$^{8a}$R$^{8b}$, —NR$^{8a}$R$^{8b}$H$^+$, —CF$_3$, —CCl$_3$, —SO$_3^-$, —SO$_3$R$^9$, —CO$_2^-$, and —CO$_2$R$^9$.

In a further aspect, each of R$^{4a}$ and R$^{4b}$, when present, is independently selected from hydrogen, halogen, —NR$^{8a}$R$^{8b}$, —NR$^{8a}$R$^{8b}$H$^+$, C1-C4 alkyl, C1-C4 monohaloalkyl, C1-C4 polyhaloalkyl, —SO$_3^-$, —SO$_3$R$^9$, —CO$_2^-$, and —CO$_2$R$^9$. In a still further aspect, each of R$^{4a}$ and R$^{4b}$, when present, is independently selected from hydrogen, —F, —Cl, —NR$^{8a}$R$^{8b}$, —NR$^{8a}$R$^{8b}$H$^+$, methyl, ethyl, propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CHF$_2$, —CF$_3$, —CHCl$_2$, —CCl$_3$, —SO$_3^-$, —SO$_3$R$^9$, —CO$_2^-$, and —CO$_2$R$^9$. In yet a further aspect, each of R$^{4a}$ and R$^{4b}$, when present, is independently selected from hydrogen, —F, —Cl, —NR$^{8a}$R$^{8b}$, —NR$^{8a}$R$^{8b}$H$^+$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —SO$_3^-$, —SO$_3$R$^9$, —CO$_2^-$, and —CO$_2$R$^9$. In an even further aspect, each of R$^{4a}$ and R$^{4b}$, when present, is independently selected from hydrogen, —F, —Cl, —NR$^{8a}$R$^{8b}$, —NR$^{8a}$R$^{8b}$H$^+$, methyl, —CH$_2$F, —CH$_2$Cl, —CHF$_2$, —CF$_3$, —CHCl$_2$, —CCl$_3$, —SO$_3^-$, —SO$_3$R$^9$, —CO$_2^-$, and —CO$_2$R$^9$. In a still further aspect, each of R$^{4a}$ and R$^{4b}$, when present, is independently selected from hydrogen, —F, —Cl, —NR$^{8a}$R$^{8b}$, —NR$^{8a}$R$^{8b}$H$^+$, —CF$_3$, —CCl$_3$, —SO$_3^-$, —SO$_3$R$^9$, —CO$_2^-$, and —CO$_2$R$^9$.

In a further aspect, each of R$^{4a}$ and R$^{4b}$, when present, is independently selected from hydrogen, —NR$^{8a}$R$^{8b}$, —NR$^{8a}$R$^{8b}$H$^+$, C1-C4 alkyl, C1-C4 monohaloalkyl, C1-C4 polyhaloalkyl, —SO$_3^-$, —SO$_3$R$^9$, —CO$_2$, and —CO$_2$R$^9$. In a still further aspect, each of R$^{4a}$ and R$^{4b}$, when present, is independently selected from hydrogen, —NR$^{8a}$R$^{8b}$, —NR$^{8a}$R$^{8b}$H$^+$, methyl, ethyl, propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CHF$_2$, —CF$_3$, —CHCl$_2$, —CCl$_3$, —SO$_3^-$, —SO$_3$R$^9$, —CO$_2^-$, and —CO$_2$R$^9$. In yet a further aspect, each of R$^{4a}$ and R$^{4b}$, when present, is independently selected from hydrogen, —NR$^{8a}$R$^{8b}$, —NR$^{8a}$R$^{8b}$H$^+$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —SO$_3^-$, —SO$_3$R$^9$, —CO$_2^-$, and —CO$_2$R$^9$. In an even further aspect, each of R$^{4a}$ and R$^{4b}$, when present, is independently selected from hydrogen, —NR$^{8a}$R$^{8b}$, —NR$^{8a}$R$^{8b}$H$^+$, methyl, —CH$_2$F, —CH$_2$Cl, —CHF$_2$, —CF$_3$, —CHCl$_2$, —CCl$_3$, —SO$_3^-$, —SO$_3$98, —CO$_2^-$, and —CO$_2$R$^9$. In a still further aspect, each of R$^{4a}$ and R$^{4b}$, when present, is independently selected from hydrogen, —NR$^{8a}$R$^{8b}$, —NR$^{8a}$R$^{8b}$H$^+$, —CF$_3$, —CCl$_3$, —SO$_3^-$, —SO$_3$R$^9$, —CO$_2^-$, and —CO$_2$R$^9$.

In a further aspect, each of R$^{4a}$ and R$^{4b}$, when present, is independently selected from hydrogen, —NR$^{8a}$R$^{8b}$, and —NR$^{8a}$R$^{8b}$H$^+$. In a still further aspect, each of R$^{4a}$ and R$^{4b}$, when present, is independently selected from hydrogen and —NR$^{8a}$R$^{8b}$H$^+$. In yet a further aspect, each of R$^{4a}$ and R$^{4b}$, when present, is hydrogen. In an even further aspect, each of R$^{4a}$ and R$^{4b}$, when present, is —NR$^{8a}$R$^{8b}$H$^+$. In a still further aspect, each of R$^{4a}$ and R$^{4b}$, when present, is —NR$^{8a}$R$^{8b}$.

In a further aspect, each of R$^{4a}$ and R$^{4b}$, when present, is independently selected from hydrogen, —SO$_3^-$, and —SO$_3$R$^9$. In a still further aspect, each of R$^{4a}$ and R$^{4b}$, when present, is independently selected from hydrogen and —SO$_3^-$. In yet a further aspect, each of R$^{4a}$ and R$^{4b}$, when present, is —SO$_3^-$. In an even further aspect, each of R$^{4a}$ and R$^{4b}$, is —SO$_3$R$^9$.

In a further aspect, each of R$^{4a}$ and R$^{4b}$, when present, is independently selected from hydrogen, —CO$_2^-$, and —CO$_2$R$^9$.

In a still further aspect, each of R$^{4a}$ and R$^{4b}$, when present, is independently selected from hydrogen and —CO$_2^-$. In yet a further aspect, each of R$^{4a}$ and R$^{4b}$, when present, is —CO$_2^-$. In an even further aspect, each of R$^{4a}$ and R$^{4b}$, is —CO$_2$R$^9$.

i. R$^{5A}$, R$^{5B}$, and R$^{5C}$ Groups

In one aspect, each of R$^{5a}$, R$^{5b}$, and R$^{5c}$, when present, is independently selected from hydrogen, halogen, —CN, —OH, —NR$^{10a}$R$^{10b}$, —NR$^{10a}$R$^{10b}$H$^+$, C1-C4 alkyl, C1-C4 monohaloalkyl, C1-C4 polyhaloalkyl, —SO$_3^-$, —SO$_3$R$^{11}$, —CO$_2^-$, and —CO$_2$R$^{11}$. In a further aspect, each of R$^{5a}$, R$^{5b}$, and R$^{5c}$, when present, is independently selected from hydrogen, —F, —Cl, —CN, —OH, —NR$^{10a}$R$^{10b}$, —NR$^{10a}$R$^{10b}$H$^+$, methyl, ethyl, propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CHF$_2$, —CF$_3$, —CHCl$_2$, —CCl$_3$, —SO$_3^-$, —SO$_3$R$^{11}$, —CO$_2^-$, and —CO$_2$R$^{11}$. In a still further aspect, each of each of R$^{5a}$, R$^{5b}$, and R$^{5c}$, when present, is independently selected from hydrogen, —F, —Cl, —CN, —OH, —NR$^{10a}$R$^{10b}$, —NR$^{10a}$R$^{10b}$H$^+$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —SO$_3^-$, —SO$_3$R$^{11}$, —CO$_2^-$, and —CO$_2$R$^{11}$. In yet a further aspect, each of R$^{5a}$, R$^{5b}$, and R$^{5c}$, when present, is independently selected from hydrogen, —F, —Cl, —CN, —OH, —NR$^{10a}$R$^{10b}$, —NR$^{10a}$R$^{10b}$H$^+$, methyl, —CH$_2$F, —CH$_2$Cl, —CHF$_2$, —CF$_3$, —CHCl$_2$, —CCl$_3$, —SO$_3^-$, —SO$_3$R$^9$, —CO$_2^-$, and —CO$_2$R$^9$. In an even further aspect, each of R$^{5a}$, R$^{5b}$, and R$^{5c}$, when present, is independently selected from hydrogen, —F, —Cl, —CN, —OH, —NR$^{10a}$R$^{10b}$, —NR$^{10a}$R$^{10b}$H$^+$, —CF$_3$, —CCl$_3$, —SO$_3^-$, —SO$_3$R$^9$, —CO$_2^-$, and —CO$_2$R$^9$.

In a further aspect, each of R$^{5a}$, R$^{5b}$, and R$^{5c}$, when present, is independently selected from halogen, —CN, —OH, —NR$^{10a}$R$^{10b}$, —NR$^{10a}$R$^{10b}$H$^+$, C1-C4 alkyl, C1-C4 monohaloalkyl, C1-C4 polyhaloalkyl, —SO$_3^-$, —SO$_3$R$^{11}$, —CO$_2^-$, and —CO$_2$R$^{11}$. In a still further aspect, each of R$^{5a}$, R$^{5b}$, and R$^{5c}$, when present, is independently selected from —F, —Cl, —CN, —OH, —NR$^{10a}$R$^{10b}$, —NR$^{10a}$R$^{10b}$H$^+$, methyl, ethyl, propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CHF$_2$, —CF$_3$, —CHCl$_2$, —CCl$_3$, —SO$_3^-$, —SO$_3$R$^{11}$, —CO$_2^-$, and —CO$_2$R$^{11}$. In yet a further aspect, each of R$^{5a}$, R$^{5b}$, and R$^{5c}$, when present, is independently selected from —F, —Cl, —CN, —OH, —NR$^{10a}$R$^{10b}$, —NR$^{10a}$R$^{10b}$H$^+$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —SO$_3^-$, —SO$_3$R$^{11}$, —CO$_2^-$, and —CO$_2$R$^{11}$. In an even further aspect, each of R$^{5a}$, R$^{5b}$, and R$^{5c}$, when present, is independently selected from —F, —Cl, —CN, —OH, —NR$^{10a}$R$^{10b}$, —NR$^{10a}$R$^{10b}$H$^+$, methyl, —CH$_2$F, —CH$_2$Cl, —CHF$_2$, —CF$_3$, —CHCl$_2$, —CCl$_3$, —SO$_3^-$, —SO$_3$R$^{11}$, —CO$_2^-$, and —CO$_2$R$^{11}$. In a still further aspect, each of R$^{5a}$, R$^{5b}$, and R$^{5c}$, when present, is independently selected from —F, —Cl, —CN, —OH, —NR$^{10a}$R$^{10b}$, —NR$^{10a}$R$^{10b}$H$^+$, —CF$_3$, —CCl$_3$, —SO$_3^-$, —SO$_3$R$^{11}$, —CO$_2^-$, and —CO$_2$R$^{11}$.

In a further aspect, each of R$^{5a}$, R$^{5b}$, and R$^{5c}$, when present, is independently selected from hydrogen, —NR$^{10a}$R$^{10b}$, —NR$^{10a}$R$^{10b}$H$^+$, C1-C4 alkyl, C1-C4 monohaloalkyl, C1-C4 polyhaloalkyl, —SO$_3^-$, —SO$_3$R$^{11}$, —CO$_2^-$, and —CO$_2$R$^{11}$. In a still further aspect, each of R$^{5a}$, R$^{5b}$, and R$^{5c}$, when present, is independently selected from hydrogen, —F, —Cl, —NR$^{10a}$R$^{10b}$, —NR$^{10a}$R$^{10b}$H$^+$, methyl, ethyl, propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CHF$_2$, —CF$_3$, —CHCl$_2$, —CCl$_3$, —SO$_3^-$, —SO$_3$R$^{11}$, —CO$_2^-$, and —CO$_2$R$^{11}$. In yet a further aspect, each of R$^{5a}$, R$^{5b}$, and R$^{5c}$, when present, is independently selected from hydrogen, —F, —Cl, —NR$^{10a}$R$^{10b}$, —NR$^{10a}$R$^{10b}$H$^+$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —SO$_3^-$, —SO$_3$R$^{11}$, —CO$_2^-$, and —CO$_2$R$^{11}$. In an even further aspect, each of R$^{5a}$, R$^{5b}$, and R$^{5c}$, when present, is independently selected from hydrogen, —F, —Cl, —NR$^{10a}$R$^{10b}$, —NR$^{10a}$R$^{10b}$H$^+$, methyl, —CH$_2$F, —CH$_2$Cl, —CHF$_2$, —CF$_3$, —CHCl$_2$, —CCl$_3$, —SO$_3^-$, —SO$_3$R$^{11}$, —CO$_2^-$, and —CO$_2$R$^{11}$. In a still further aspect, each of R$^{5a}$, R$^{5b}$, and R$^{5c}$, when present, is independently selected from hydrogen, —F, —Cl, —NR$^{10a}$R$^{10b}$, —NR$^{10a}$R$^{10b}$H$^+$, —CF$_3$, —CCl$_3$, —SO$_3^-$, —SO$_3$R$^{11}$, —CO$_2^-$, and —CO$_2$R$^{11}$.

In a further aspect, each of R$^{5a}$, R$^{5b}$, and R$^{5c}$, when present, is independently selected from hydrogen, —NR$^{10a}$R$^{10b}$, —NR$^{10a}$R$^{10b}$H$^+$, C1-C4 alkyl, C1-C4 monohaloalkyl, C1-C4 polyhaloalkyl, —SO$_3^-$, —SO$_3$R$^{11}$, —CO$_2^-$, and —CO$_2$R$^{11}$. In a still further aspect, each of R$^{5a}$, R$^{5b}$, and R$^{5c}$, when present, is independently selected from hydrogen, —NR$^{10a}$R$^{10b}$, —NR$^{10a}$R$^{10b}$H$^+$, methyl, ethyl, propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CHF$_2$, —CF$_3$, —CHCl$_2$, —CCl$_3$, —SO$_3^-$, —SO$_3$R$^{11}$, —CO$_2^-$, and —CO$_2$R$^{11}$. In yet a further aspect, each of R$^{5a}$, R$^{5b}$, and R$^{5c}$, when present, is independently selected from hydrogen, —NR$^{10a}$R$^{10b}$, —NR$^{10a}$R$^{10b}$H$^+$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —SO$_3^-$, —SO$_3$R$^{11}$, —CO$_2^-$, and —CO$_2$R$^{11}$. In an even further aspect, each of R$^{5s}$, R$^{5b}$, and R$^{5c}$, when present, is independently selected from hydrogen, —NR$^{10a}$R$^{10b}$, —NR$^{10a}$R$^{10b}$H$^+$, methyl, —CH$_2$F, —CH$_2$Cl, —CHF$_2$, —CF$_3$, —CHCl$_2$, —CCl$_3$, —SO$_3^-$, —SO$_3$R$^{11}$, —CO$_2^-$, and —CO$_2$R$^{11}$. In a still further aspect, each of R$^{5a}$, R$^{5b}$, and R$^{5c}$, when present, is independently selected from hydrogen, —NR$^{10a}$R$^{10b}$, —NR$^{10a}$R$^{10b}$H$^+$, —CF$_3$, —CCl$_3$, —SO$_3^-$, —SO$_3$R$^{11}$, —CO$_2^-$, and —CO$_2$R$^{11}$.

In a further aspect, each of R$^{5a}$, R$^{5b}$, and R$^{5c}$, when present, is independently selected from hydrogen, —NR$^{10a}$R$^{10b}$, and —NR$^{10a}$R$^{10b}$H$^+$. In a still further aspect, each of R$^{5a}$, R$^{5b}$, and R$^{5c}$, when present, is independently selected from hydrogen and —NR$^{10a}$R$^{10b}$H$^+$. In yet a further aspect, each of R$^{5a}$, R$^{5b}$, and R$^{5c}$, when present, is hydrogen. In an even further aspect, each of R$^{5a}$, R$^{5b}$, and R$^{5c}$, when present, is —NR$^{10a}$R$^{10b}$H$^+$. In a still further aspect, each of R$^{5a}$, R$^{5b}$, and R$^{5c}$, when present, is —NR$^{10a}$R$^{10b}$.

In a further aspect, each of R$^{5a}$, R$^{5b}$, and R$^{5c}$, when present, is independently selected from hydrogen, —SO$_3^-$, and —SO$_3$R$^8$. In a still further aspect, each of R$^{5a}$, R$^{5b}$, and R$^{5c}$, when present, is independently selected from hydrogen and —SO$_3^-$. In yet a further aspect, each of R$^{5a}$, R$^{5b}$, and R$^{5c}$, when present, is —SO$_3^-$. In an even further aspect, each of R$^{5a}$, R$^{5b}$, and R$^{5c}$, when present, is —SO$_3$R$^8$.

In a further aspect, each of R$^{5a}$, R$^{5b}$, and R$^{5c}$, when present, is independently selected from hydrogen, —CO$_2^-$, and —CO$_2$R$^8$. In a still further aspect, each of R$^{5a}$, R$^{5b}$, and R$^{5c}$, when present, is independently selected from hydrogen and —CO$_2^-$. In yet a further aspect, each of R$^{5a}$, R$^{5b}$, and R$^{5c}$, when present, is —CO$_2^-$. In an even further aspect, each of R$^{5a}$, R$^{5b}$, and R$^{5c}$, when present, is —CO$_2$R$^8$.

j. R$^{6A}$ and R$^{6B}$ Groups

In one aspect, each of R$^{6a}$ and R$^{6b}$, when present, is independently selected hydrogen, halogen, —CN, —OH, —NR$^{12a}$R$^{12b}$, —NR$^{12a}$R$^{12b}$H$^+$, C1-C4 alkyl, C1-C4 monohaloalkyl, C1-C4 polyhaloalkyl, —SO$_3^-$, —SO$_3$R$^{13}$, —CO$_2^-$, and —CO$_2$R$^{13}$. In a further aspect, each of R$^{6a}$ and R$^{6b}$, when present, is independently selected from hydrogen, —F, —Cl, —CN, —OH, —NR$^{12a}$R$^{12b}$, —NR$^{12a}$R$^{12b}$H$^+$, methyl, ethyl, propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CHF$_2$, —CF$_3$, —CHCl$_2$, —CCl$_3$, —SO$_3^-$, —SO$_3$R$^{13}$, —CO$_2^-$, and —CO$_2$R$^{13}$. In a still further aspect, each of each of R$^{6a}$ and R$^{6b}$, when present, is independently selected from hydrogen, —F, —Cl, —CN, —OH, —NR$^{12a}$R$^{12b}$, —NR$^{12a}$R$^{12b}$H$^+$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —SO$_3^-$, —SO$_3$R$^{13}$, —CO$_2^-$, and —CO$_2$R$^{13}$. In yet a further aspect, each of R$^{6a}$ and R$^{6b}$, when present, is independently selected from hydrogen, —F, —Cl, —CN, —OH, —NR$^{12a}$R$^{12b}$, —NR$^{12a}$R$^{12b}$H$^+$, methyl, —CH$_2$F, —CH$_2$Cl, —CHF$_2$, —CF$_3$, —CHCl$_2$, —CCl$_3$, —SO$_3^-$, —SO$_3$R$^{13}$, —CO$_2^-$, and —CO$_2$R$^{13}$. In an even further aspect, each of R$^{6a}$ and R$^{6b}$, when present, is independently selected from hydrogen, —F, —Cl, —CN, —OH, —NR$^{12a}$R$^{12b}$, —NR$^{12a}$R$^{12b}$H$^+$, —CF$_3$, —CCl$_3$, —SO$_3^-$, —SO$_3$R$^{13}$, —CO$_2^-$, and —CO$_2$R$^{13}$.

In a further aspect, each of R$^{6a}$ and R$^{6b}$, when present, is independently selected from halogen, —CN, —OH, —NR$^{12a}$R$^{12b}$, —NR$^{12a}$R$^{12b}$H$^+$, C1-C4 alkyl, C1-C4 monohaloalkyl, C1-C4 polyhaloalkyl, —SO$_3^-$, —SO$_3$R$^{13}$, —CO$_2^-$, and —CO$_2$R$^{13}$. In a still further aspect, each of R$^{6a}$ and R$^{6b}$, when present, is independently selected from —F, —Cl, —CN, —OH, —NR$^{12a}$R$^{12b}$, —NR$^{12a}$R$^{12b}$H$^+$, methyl, ethyl, propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CHF$_2$, —CF$_3$, —CHCl$_2$, —CCl$_3$, —SO$_3^-$, —SO$_3$R$^{13}$, —CO$_2^-$, and —CO$_2$R$^{13}$. In yet a further aspect, each of R$^{6a}$ and R$^{6b}$, when present, is independently selected from —F, —Cl, —CN, —OH, —NR$^{12a}$R$^{12b}$, —NR$^{12a}$R$^{12b}$H$^+$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —SO$_3^-$, —SO$_3$R$^{13}$, —CO$_2$, and —CO$_2$R$^{13}$. In an even further aspect, each of R$^{6a}$ and R$^{6b}$, when present, is independently selected from —F, —Cl, —CN, —OH, —NR$^{12a}$R$^{12b}$, —NR$^{12a}$R$^{12b}$H$^+$, methyl, —CH$_2$F, —CH$_2$Cl, —CHF$_2$, —CF$_3$, —CHCl$_2$, —CCl$_3$, —SO$_3^-$, —SO$_3$R$^{13}$, —CO$_2^-$, and —CO$_2$R$^{13}$. In a still further aspect, each of R$^{6a}$ and R$^{6b}$, when present, is independently selected from —F, —Cl, —CN, —OH, —NR$^{12a}$R$^{12b}$, —NR$^{12a}$R$^{12b}$H$^+$, —CF$_3$, —CCl$_3$, —SO$_3^-$, —SO$_3$R$^{13}$, —CO$_2^-$, and —CO$_2$R$^{13}$.

In a further aspect, each of R$^{6a}$ and R$^{6b}$, when present, is independently selected from hydrogen, halogen, —NR$^{12a}$R$^{12b}$, —NR$^{12a}$R$^{12b}$H$^+$, C1-C4 alkyl, C1-C4 monohaloalkyl, C1-C4 polyhaloalkyl, —SO$_3^-$, —SO$_3$R$^{13}$, —CO$_2^-$, and —CO$_2$R$^{13}$. In a still further aspect, each of R$^{6a}$ and R$^{6b}$, when present, is independently selected from hydrogen, —F, —Cl, —NR$^{12a}$R$^{12b}$, —NR$^{12a}$R$^{12b}$H$^+$, methyl, ethyl, propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CHF$_2$, —CF$_3$, —CHCl$_2$, —CCl$_3$, —SO$_3^-$, —SO$_3$R$^{13}$, —CO$_2^-$, and —CO$_2$R$^{13}$. In yet a further aspect, each of R$^{6a}$ and R$^{6b}$, when present, is independently selected from hydrogen, —F, —Cl, —NR$^{12a}$R$^{12b}$, —NR$^{12a}$R$^{12b}$H$^+$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —SO$_3^-$, —SO$_3$R$^{13}$, —CO$_2$, and —CO$_2$R$^{13}$. In an even further aspect, each of R$^{6a}$ and R$^{6b}$, when present, is independently selected from hydrogen, —F, —Cl, —NR$^{12a}$R$^{12b}$, —NR$^{12a}$R$^{12b}$H$^+$, methyl, —CH$_2$F, —CH$_2$Cl, —CHF$_2$, —CF$_3$, —CHCl$_2$, —CCl$_3$, —SO$_3^-$, —SO$_3$R$^{13}$, —CO$_2^-$, and —$CO_2R^{13}$. In a still further aspect, each of $R^{6a}$ and $R^{6b}$, when present, is independently selected from hydrogen, —F, —Cl, —$NR^{12a}R^{12b}$, —$NR^{12a}R^{12b}H^+$, —$CF_3$, —$CCl_3$, —$SO_3^-$, —$SO_3R^{13}$, —$CO_2^-$, and —$CO_2R^{13}$.

In a further aspect, each of $R^{6a}$ and $R^{6b}$, when present, is independently selected from hydrogen, —$NR^{12a}R^{12b}$, —$NR^{12a}R^{12b}H^+$, C1-C4 alkyl, C1-C4 monohaloalkyl, C1-C4 polyhaloalkyl, —$SO_3^-$, —$SO_3R^{13}$, —$CO_2^-$, and —$CO_2R^{13}$. In a still further aspect, each of $R^{6a}$ and $R^{6b}$, when present, is independently selected from hydrogen, —$NR^{12a}R^{12b}$, —$NR^{12a}R^{12b}H^+$, methyl, ethyl, propyl, —$CH_2F$, —$CH_2Cl$, —$CH_2CH_2F$, —$CH_2CH_2Cl$, —$CH_2CH_2CH_2F$, —$CH_2CH_2CH_2Cl$, —$CHF_2$, —$CF_3$, —$CHCl_2$, —$CCl_3$, —$SO_3^-$, —$SO_3R^{13}$, —$CO_2^-$, and —$CO_2R^{13}$. In yet a further aspect, each of $R^{6a}$ and $R^{6b}$, when present, is independently selected from hydrogen, —$NR^{12a}R^{12b}$, —$NR^{12a}R^{12b}H^+$, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$SO_3^-$, —$SO_3R^{13}$, —$CO_2^-$, and —$CO_2R^{13}$. In an even further aspect, each of $R^{6a}$ and $R^{6b}$, when present, is independently selected from hydrogen, —$NR^{12a}R^{12b}$, —$NR^{12a}R^{12b}H^+$, methyl, —$CH_2F$, —$CH_2Cl$, —$CHF_2$, —$CF_3$, —$CHCl_2$, —$CCl_3$, —$SO_3^-$, —$SO_3R^{13}$, —$CO_2^-$, and —$CO_2R^{13}$. In a still further aspect, each of $R^{6a}$ and $R^{6b}$, when present, is independently selected from hydrogen, —$NR^{12a}R^{12b}$, —$NR^{12a}R^{12b}H^+$, —$CF_3$, —$CCl_3$, —$SO_3^-$, —$SO_3R^{13}$, —$CO_2^-$, and —$CO_2R^{13}$.

In a further aspect, each of $R^{6a}$ and $R^{6b}$, when present, is independently selected from hydrogen, —$NR^{12a}R^{12b}$, and —$NR^{12a}R^{12b}H^+$. In a still further aspect, each of $R^{6a}$ and $R^{6b}$, when present, is selected from hydrogen and —$NR^{12a}R^{12b}H^+$. In yet a further aspect, each of $R^{6a}$ and $R^{6b}$, when present, is hydrogen. In an even further aspect, each of $R^{6a}$ and $R^{6b}$, when present, is —$NR^{12a}R^{12b}H+$. In a still further aspect, each of $R^{6a}$ and $R^{6b}$, when present, is —$NR^{12a}R^{12b}$.

In a further aspect, each of $R^{6a}$ and $R^{6b}$, when present, is independently selected from hydrogen, —$SO_3^-$, and —$SO_3R^{13}$. In a still further aspect, each of $R^{6a}$ and $R^{6b}$, when present, is independently selected from hydrogen and —$SO_3^-$. In yet a further aspect, each of $R^{6a}$ and $R^{6b}$, when present, is —$SO_3^-$. In an even further aspect, each of $R^{6a}$ and $R^{6b}$, when present, is —$SO_3R^{13}$.

In a further aspect, each of $R^{6a}$ and $R^{6b}$, when present, is independently selected from hydrogen, —$CO_2^-$, and —$CO_2R^{13}$. In a still further aspect, each of $R^{6a}$ and $R^{6b}$, when present, is independently selected from hydrogen and —$CO_2^-$. In yet a further aspect, each of $R^{6a}$ and $R^{6b}$, when present, is —$CO_2^-$. In an even further aspect, each of $R^{6a}$ and $R^{6b}$, when present, is —$CO_2R^{13}$.

k. $R^7$ Groups

In one aspect, $R^7$, when present, is selected from hydrogen and C1-C4 alkyl. In a further aspect, $R^7$, when present, is selected from hydrogen, methyl, ethyl, and propyl. In a still further aspect, $R^7$, when present, is selected from hydrogen, methyl, and ethyl. In yet a further aspect, $R^7$, when present, is selected from hydrogen and methyl. In an even further aspect, $R^7$, when present, is hydrogen.

l. $R^8$, $R^{8A}$, and $R^{8B}$ Groups

In one aspect, $R^8$, $R^{8a}$, or $R^{8b}$, when present, is selected from hydrogen and C1-C4 alkyl. In a further aspect, $R^8$, $R^{8a}$, or $R^{8b}$, when present, is selected from hydrogen, methyl, ethyl, and propyl. In a still further aspect, $R^8$, $R^{8a}$, or $R^{8b}$, when present, is selected from hydrogen, methyl, and ethyl. In yet a further aspect, $R^8$, $R^{8a}$, or $R^{8b}$, when present, is selected from hydrogen and methyl. In an even further aspect, $R^8$, $R^{8a}$, or $R^{8b}$, when present, is hydrogen.

m. $R^9$ Groups

In one aspect, $R^9$, when present, is selected from hydrogen and C1-C4 alkyl. In a further aspect, $R^9$, when present, is selected from hydrogen, methyl, ethyl, and propyl. In a still further aspect, $R^9$, when present, is selected from hydrogen, methyl, and ethyl. In yet a further aspect, $R^9$, when present, is selected from hydrogen and methyl. In an even further aspect, $R^9$, when present, is hydrogen.

n. $R^{10}$, $R^{10A}$, and $R^{10B}$ Groups

In one aspect, $R^{10}$, $R^{10a}$, or $R^{10b}$, when present, is selected from hydrogen and C1-C4 alkyl. In a further aspect, $R^{10}$, $R^{10a}$, or $R^{10b}$, when present, is selected from hydrogen, methyl, ethyl, and propyl. In a still further aspect, $R^{10}$, $R^{10a}$, or $R^{10b}$, when present, is selected from hydrogen, methyl, and ethyl. In yet a further aspect, $R^{10}$, $R^{10a}$, or $R^{10b}$, when present, is selected from hydrogen and methyl. In an even further aspect, $R^{10}$, $R^{10a}$, or $R^{10b}$, when present, is hydrogen.

o. $R^{11}$ Groups

In one aspect, $R^{11}$, when present, is selected from hydrogen and C1-C4 alkyl. In a further aspect, $R^{11}$, when present, is selected from hydrogen, methyl, ethyl, and propyl. In a still further aspect, $R^{11}$, when present, is selected from hydrogen, methyl, and ethyl. In yet a further aspect, $R^{11}$, when present, is selected from hydrogen and methyl. In an even further aspect, $R^{11}$, when present, is hydrogen.

p. $R^{12}$, $R^{12A}$, and $R^{12B}$ Groups

In one aspect, $R^{12}$, $R^{12a}$, or $R^{12b}$, when present, is selected from hydrogen and C1-C4 alkyl. In a further aspect, $R^{12}$, $R^{12a}$, or $R^{12b}$, when present, is selected from hydrogen, methyl, ethyl, and propyl. In a still further aspect, $R^{12}$, $R^{12a}$, or $R^{12b}$, when present, is selected from hydrogen, methyl, and ethyl. In yet a further aspect, $R^{12}$, $R^{12a}$, or $R^{12b}$, when present, is selected from hydrogen and methyl. In an even further aspect, $R^{12}$, $R^{12a}$, or $R^{12b}$, when present, is hydrogen.

$R^{13}$ Groups q. $R^{13}$ Groups

In one aspect, $R^{13}$, when present, is selected from hydrogen and C1-C4 alkyl. In a further aspect, $R^{13}$, when present, is selected from hydrogen, methyl, ethyl, and propyl. In a still further aspect, $R^{13}$, when present, is selected from hydrogen, methyl, and ethyl. In yet a further aspect, $R^{13}$, when present, is selected from hydrogen and methyl. In an even further aspect, $R^{13}$, when present, is hydrogen.

2. Example Structures

In one aspect, a residue of a compound can be present as:

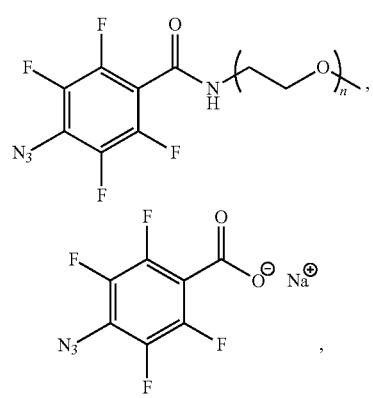

-continued

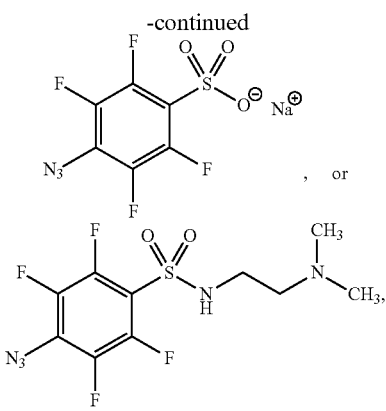

, or

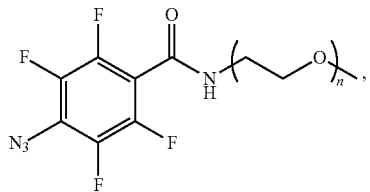

or a subgroup thereof.

In a further aspect, a residue of a compound can be present as:

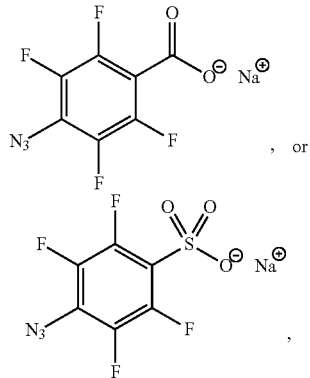

or a subgroup thereof.

In a still further aspect, a residue of a compound can be present as:

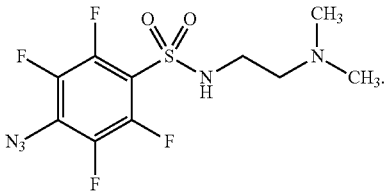 [SMILES: CN(C)CCNS(=O)(=O)c1c(F)c(F)c(N=[N+]=[N-])c(F)c1F]

or a subgroup thereof.

In yet a further aspect, a residue of a compound can be present as:

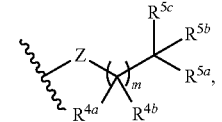

In one aspect, a compound can be present as:

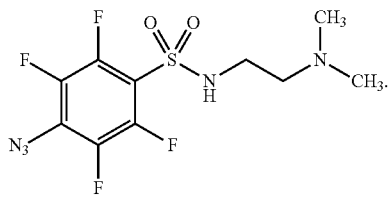 [SMILES: CN(C)CCNS(=O)(=O)c1c(F)c(F)c(N=[N+]=[N-])c(F)c1F]

D. Methods of Modifying Thin-Film Membranes

In one aspect, the invention relates to methods of modifying a thin-film membrane comprising a surface, the method comprising the step of bonding the surface with at least one residue of a compound having a structure represented by a formula:

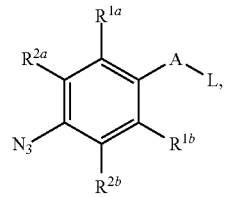

wherein A is selected from —C(═O)— and —(SO$_2$)—; wherein L is selected from —OQ, —O—, —N$^+$R$^3$HQ and —NR$^3$Q; wherein Q is selected from hydrogen, a hydrophilic polymer, and a structure represented by a formula:

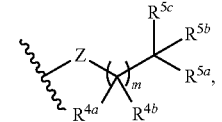

wherein Z is selected from —CR$^{6a}$R$^{6b}$—, —C(═O)—, —C(═NH)—, and —C(═NH)NR$^7$—; wherein m is an integer selected from 0, 1, 2, 3, 4, 5, 6, 7, and 8; wherein each of R$^{1a}$ and R$^{1b}$ is independently selected hydrogen and halogen; wherein each of R$^{2a}$ and R$^{2b}$ is halogen; wherein R$^3$, when present, is selected from hydrogen and C1-C4 alkyl; wherein each of R$^{4a}$ and R$^{4b}$, when present, is independently selected from hydrogen, halogen, —CN, —OH, —NR$^{8a}$R$^{8b}$, —NR$^{8a}$R$^{8b}$ H$^+$, C1-C4 alkyl, C1-C4 monohaloalkyl, C1-C4 polyhaloalkyl, —SO$_3^-$, —SO$_3$R$^9$, —CO$_2^-$, and —CO$_2$R$^9$; wherein each of R$^{5a}$, R$^{5b}$, and R$^{5c}$ is independently selected from hydrogen, halogen, —CN, —OH, —NR$^{10a}$R$^{10b}$, —NR$^{10a}$R$^{10b}$ H$^+$, C1-C4 alkyl, C1-C4 monohaloalkyl, C1-C4 polyhaloalkyl, —SO$_3^-$, —SO$_3$R$^{11}$, —CO$_2^-$, and —CO$_2$R$^{11}$; wherein each of R$^{6a}$ and R$^{6b}$, when present, is independently selected hydrogen, halogen, —CN, —OH, —NR$^{12a}$R$^{12b}$, —NR$^{12a}$R$^{12b}$ H$^+$, C1-C4 alkyl, C1-C4 monohaloalkyl, C1-C4 polyhaloalkyl, —SO$_3^-$, —SO$_3$R$^{13}$, —CO$_2^-$, and —CO$_2$R$^{13}$; wherein R$^7$, when present, is selected from hydrogen and C1-C4 alkyl; wherein each of R$^{8a}$ and R$^{8b}$, when present, is independently selected from hydrogen and C1-C4 alkyl; wherein R$^9$, when present, is selected from hydrogen and C1-C4 alkyl; wherein each of R$^{10a}$ and R$^{10b}$, when present, is independently selected from hydrogen and C1-C4 alkyl; wherein R$^{11}$, when present, is selected from hydrogen and C1-C4 alkyl; wherein each of $R^{12a}$ and $R^{12b}$, when present, is independently selected from hydrogen and C1-C4 alkyl; and wherein $R^{13}$, when present, is selected from hydrogen and C1-C4 alkyl. In a further aspect, the membrane is a reverse osmosis membrane. In a still further aspect, the membrane comprises at least one polyamide. In yet a further aspect, the polyamide is aromatic.

In a further aspect, the membrane exhibits an improvement in at least one property selected from resistance to fouling, hydropholicity, surface charge, and roughness. In a still further aspect, the membrane demonstrates an improvement in at least one property selected from resistance to fouling and hydrophilicity. In yet a further aspect, the membrane demonstrates an improvement in resistance to fouling. In an even further aspect, the membrane demonstrates an improvement in hydrophilicity. In a still further aspect, the membrane demonstrates an improvement in surface charge. In yet a further aspect, the membrane demonstrates an improvement in roughness.

In one aspect, the invention relates to methods of modifying a thin-film membrane comprising a surface, the method comprising the step of bonding the surface with at least one residue of a compound comprising a singlet nitrene, thereby improving at least one property selected from resistance to fouling, surface charge, hydrophilicity, and roughness. In a further aspect, the at least one property is selected from resistance to fouling and hydrophilicity. In a still further aspect, the membrane demonstrates an improvement in resistance to fouling. In yet a further aspect, the membrane demonstrates an improvement in hydrophilicity. In an even further aspect, the membrane demonstrates an improvement in surface charge. In a still further aspect, the membrane demonstrates an improvement in roughness.

In a further aspect, the surface comprises at least one —NH— and/or —C=C— residue.

In a further aspect, bonding comprises singlet nitrene insertion.

In a further aspect, bonding comprises coating the membrane with the at least one residue of a compound. In a still further aspect, coating comprises dip-coating. In yet a further aspect, coating comprises spray coating.

In a further aspect, bonding comprises exposing the membrane to a heat source. Examples of a heat source that may be used include, but are not limited to, a stream of hot air, an oven, and an IR lamp. In yet a further aspect, the temperature of the heat source is at least about 100° C.

In a further aspect, bonding comprises exposing the membrane to a light source. In a still further aspect, the light source comprises UV light. In yet a further aspect, the light source comprises UV light in the range of from between 200 nm and 370 nm. In an even further aspect, bonding comprises coating the membrane with the at least one residue of a compound and exposing the membrane to a light source.

In a further aspect, bonding comprises a covalent modification. In a still further aspect, bonding comprises a photochemical modification.

In a further aspect, the at least one residue of a compound is water soluble.

In a further aspect, the at least one residue of a compound has a structure represented by a formula:

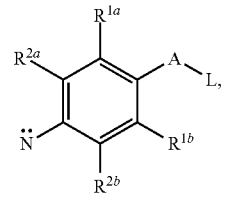

wherein A is selected from —C(=O)— and —(SO$_2$)—; wherein L is selected from —OQ, —O—, —N$^+$R$^3$HQ and —NR$^3$Q; wherein Q is selected from hydrogen, a hydrophilic polymer, and a structure represented by a formula:

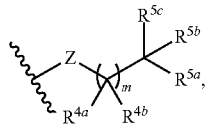

wherein Z is selected from —CR$^{6a}$R$^{6b}$—, —C(=O)—, —C(=NH)—, and —C(=NH)NR$^7$—; wherein m is an integer selected from 0, 1, 2, 3, 4, 5, 6, 7, and 8; wherein each of $R^{1a}$ and $R^{1b}$ is independently selected hydrogen and halogen; wherein each of $R^{2a}$ and $R^{2b}$ is halogen; wherein $R^3$, when present, is selected from hydrogen and C1-C4 alkyl; wherein each of $R^{4a}$ and $R^{4b}$, when present, is independently selected from hydrogen, halogen, —CN, —OH, —NR$^{8a}$R$^{8b}$, —NR$^{8a}$R$^{8b}$ H$^+$, C1-C4 alkyl, C1-C4 monohaloalkyl, C1-C4 polyhaloalkyl, —SO$_3^-$, —SO$_3$R$^9$, —CO$_2^-$, and —CO$_2$R$^9$; wherein each of $R^{5a}$, $R^{5b}$, and $R^{5c}$ is independently selected from hydrogen, halogen, —CN, —OH, —NR$^{10a}$R$^{10b}$, —NR$^{10a}$R$^{10b}$ H$^+$, C1-C4 alkyl, C1-C4 monohaloalkyl, C1-C4 polyhaloalkyl, —SO$_3^-$, —SO$_3$R$^{11}$, —CO$_2^-$, and —CO$_2$R$^{11}$; wherein each of $R^{6a}$ and $R^{6b}$, when present, is independently selected hydrogen, halogen, —CN, —OH, —NR$^{12a}$R$^{12b}$, —NR$^{12a}$R$^{12b}$ H$^+$, C1-C4 alkyl, C1-C4 monohaloalkyl, C1-C4 polyhaloalkyl, —SO$_3^-$, —SO$_3$R$^{13}$, —CO$_2^-$, and —CO$_2$R$^{13}$; wherein R$^7$, when present, is selected from hydrogen and C1-C4 alkyl; wherein each of $R^{8a}$ and $R^{8b}$, when present, is independently selected from hydrogen and C1-C4 alkyl; wherein R$^9$, when present, is selected from hydrogen and C1-C4 alkyl; wherein each of $R^{10a}$ and $R^{10b}$, when present, is independently selected from hydrogen and C1-C4 alkyl; wherein R$^{11}$, when present, is selected from hydrogen and C1-C4 alkyl; wherein each of $R^{12a}$ and $R^{12b}$, when present, is independently selected from hydrogen and C1-C4 alkyl; and wherein R$^{13}$, when present, is selected from hydrogen and C1-C4 alkyl.

In a further aspect, the singlet nitrene is formed via activation of an azide. In a still further aspect, activation is photoactivation. In yet a further aspect, photoactivation comprises exposing the at least one residue of a compound to a light source. In an even further aspect, the light source comprises UV light. In a still further aspect, the light source comprises UV light in the range of from between 200 nm and 370 nm.

In a further aspect, the membrane exhibits an improvement in at least one property selected from resistance to fouling, hydropholicity, surface charge, salt rejection, and roughness. In a still further aspect, the membrane demonstrates an improvement in at least one property selected from resistance to fouling, salt rejection, and hydrophilicity. In yet a further aspect, the membrane demonstrates an improvement in resistance to fouling. In an even further aspect, the membrane demonstrates an improvement in hydrophilicity. In a still further aspect, the membrane demonstrates an improvement in surface charge. In yet a further aspect, the membrane demonstrates an improvement in roughness. In an even further aspect, the membrane demonstrates an improvement in salt rejection.

E. Methods of Purifying Water

In one aspect, the invention relates to methods of purifying water, the method comprising: a) providing a disclosed membrane, or a membrane modified according to a disclosed process, the membrane having a first face and a second face; b) contacting the first face of the membrane with a first solution of a first volume having a first salt concentration at a first pressure; and c) contacting the second face of the membrane with a second solution of a second volume having a second salt concentration at a second pressure; wherein the first solution is in fluid communication with the second solution through the membrane, wherein the first salt concentration is higher than the second salt concentration, thereby creating an osmotic pressure across the membrane, and wherein the first pressure is sufficiently higher than the second pressure to overcome the osmotic pressure, thereby increasing the second volume and decreasing the first.

The feasibility of a membrane separation process is typically determined by stability in water flux and solute retention with time. Fouling, and in particular biological fouling, can alter the selectivity of a membrane and cause membrane degradation either directly by microbial action or indirectly through increased cleaning requirements. These characteristics can have a direct effect on the size of the membrane filtration plant, the overall investment costs, and operating and maintenance expenses. By applying the membranes and methods disclosed herein to commercial membrane and desalination processes, the overall costs can be significantly reduced due to the improved fouling resistance of the membranes of the invention. Due to the hydrophilic polymers covalently bonded to the membrane surface, frequent cleaning and membrane replacement is no longer required, thereby offering additional savings to owners and operators of these processes.

F. Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. General Methods

Methoxypolyethylene glycol amine MW=5000 g/mol was purchased from Sigma Aldrich (Milwaukee, Wis.), Methoxypolyethylene glycol amines MW=550, 1000 g/mol were purchased from Laysan Bio (Arab, Ala.), N—hydroxysuccinimidyl 2,3,5,6-tetrafluorobenzoate was prepared according to Keana and Cai.[1] Diethyl ether and methanol were purchased from Fisher Scientific (Pittsburgh, Pa.). Dow FILMTEC XLE brackish water flat sheet membranes were donated by Dow Water & Processes Solutions (Edina, Minn.). The membranes were soaked in DI water overnight to remove the shipping preservative and dried. Unless otherwise stated, all materials were used as received. $^1$H and $^{19}$F-NMR spectroscopy was conducted on a Bruker AV 300 NMR Spectrometer. Spectra were recorded in a solution of $CDCl_3$ at room temperature, referenced to a residual solvent peak for $CDCl_3$. Powder ATR-IR was conducted on the products using a JASCO FT/IR-6300 spectrometer with an ATR accessory.

2. Synthesis of PFPA-PEG

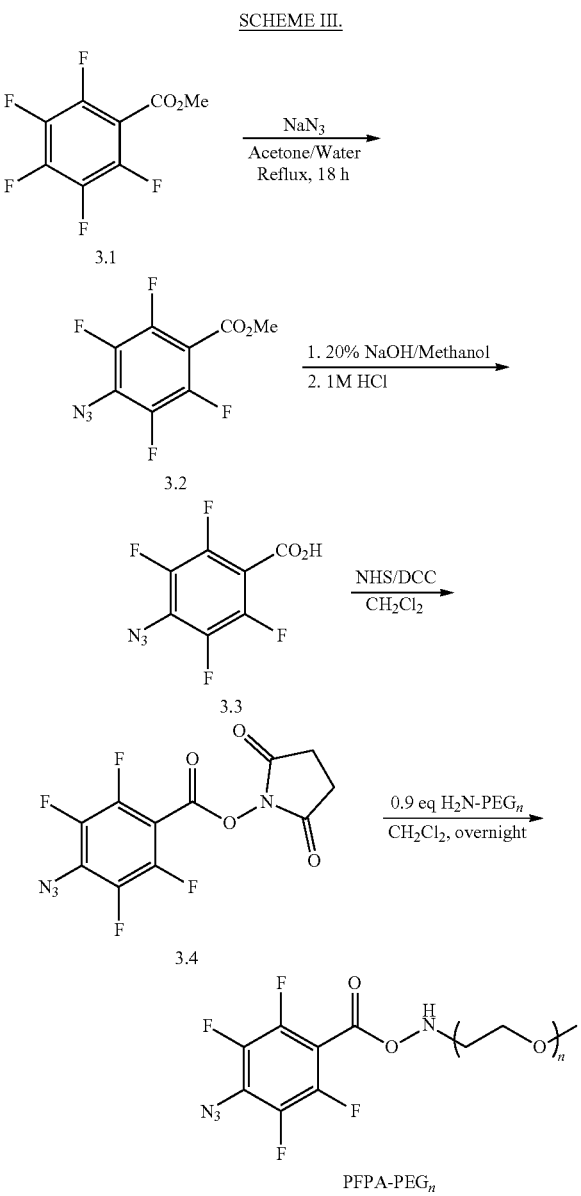

PFPA-PEG derivatives were synthesized by a modified procedure originally described by Yan (Yan, M. (2000) *Reactive and Functional Polymers* 45, 137-144). Briefly, 1 equivalent of N—hydroxysuccinimidyl 2,3,5,6-tetrafluorobenzoate and 0.9 equivalents of the H₂N—PEG were dissolved in CHCl₃. The solution was stirred overnight in the dark at room temperature. The reaction mixture was then poured into diethyl ether and extracted three times with water. After evaporation under reduced pressure, the product was collected and used without further purification.

a. Synthesis of methyl 4-azido-2,3,5,6-tetrafluorobenzoate 3.2

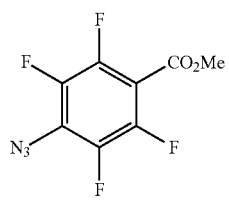 [SMILES: COC(=O)c1c(F)c(F)c(N=[N+]=[N-])c(F)c1F]

Figure 2:
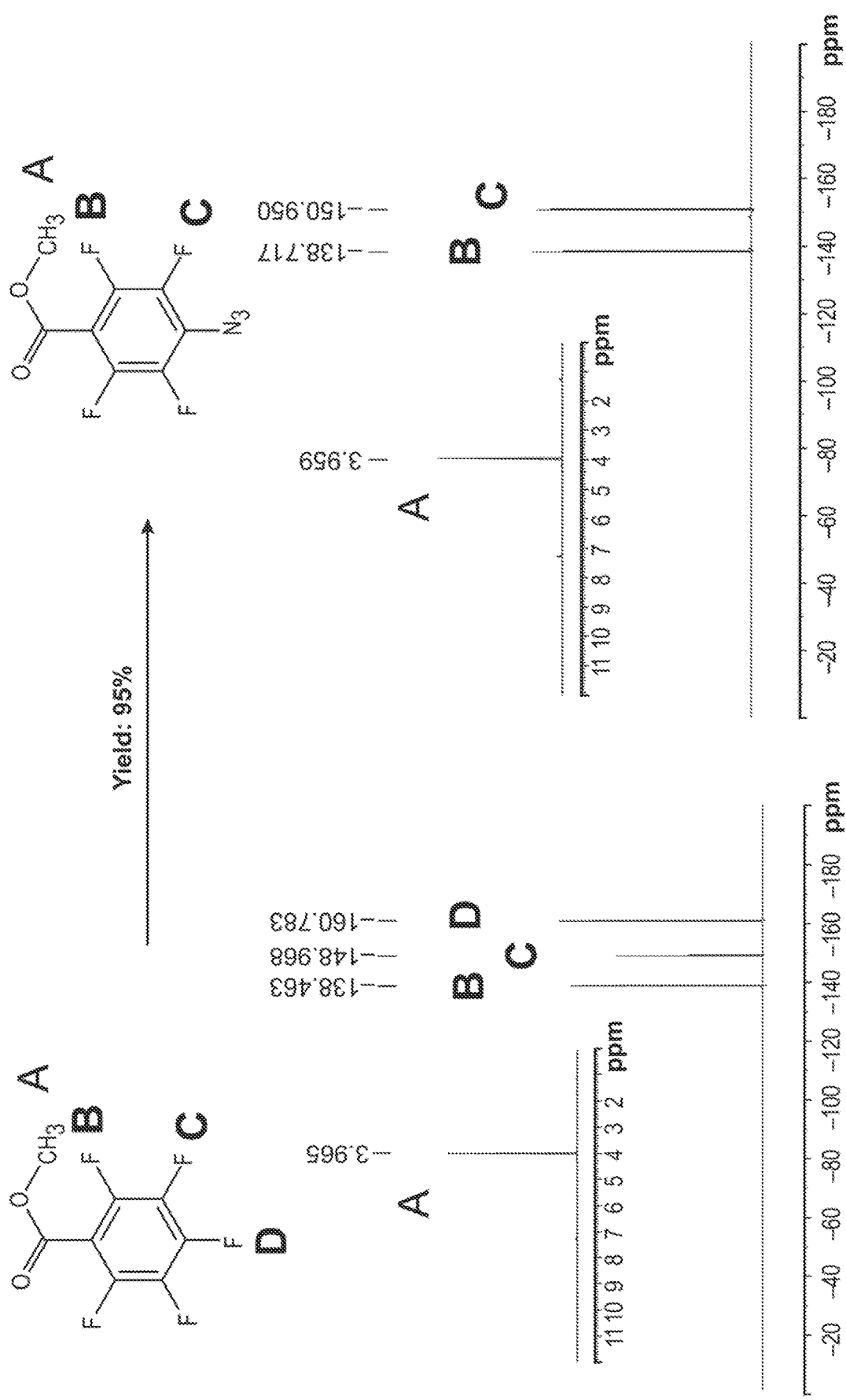
FIG. 2 shows representative spectral data confirming the synthesis of methyl 4-azido-2,3,5,6-tetrafluorobenzoate (Scheme III, 3.2).

A mixture of 0.30 (4.6 mmol) of NaN₃ and 0.88 g (4.3 mmol) of pentafluorobenzaldehyde (3.1) in acetone (8 mL) and water (3 mL) was refluxed for 8 h. The mixture was cooled, diluted with water (10 mL), and then extracted by ether (3×10 mL). The extract was dried (MgSO₄) and evaporated to leave 87% of 3.2 as a colorless solid (FIG. 2).

b. Synthesis of 4-azido-2,3,5,6-tetrafluorobenzoic Acid 3.3

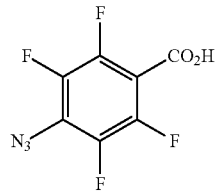 [SMILES: [N-]=[N+]=Nc1c(F)c(F)c(C(=O)O)c(F)c1F]

Figure 3:
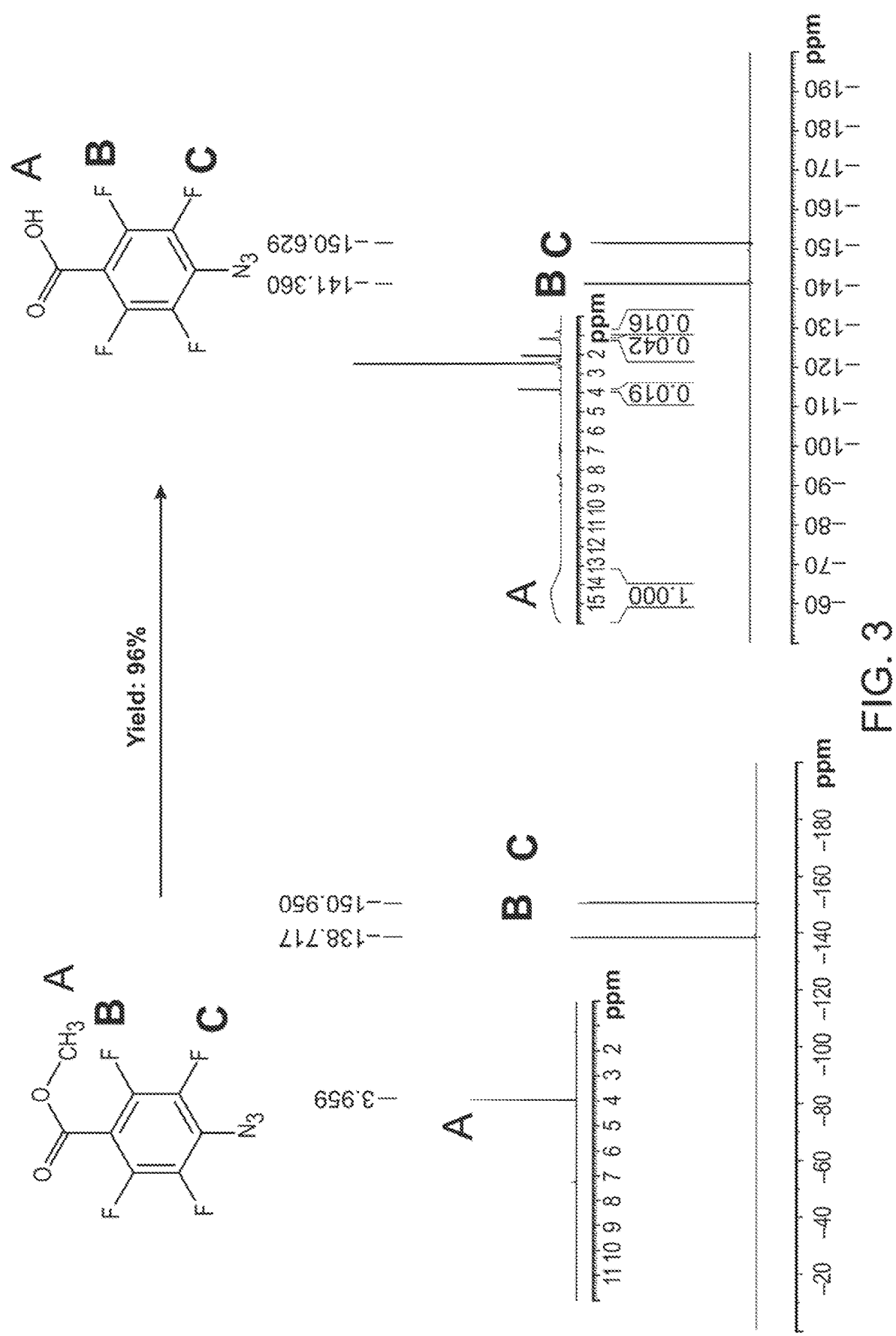
FIG. 3 shows representative spectral data confirming the synthesis of 4-azido-2,3,5,6-tetrafluorobenzoic acid (Scheme III, 3.3).

A solution of 0.586 g of 3.2 with 20% aqueous NaOH (0.8 mL) in MeOH (10 mL) and water (1 mL) was stirred overnight at 25° C. The solution was acidified by 1 M HCl in an ice bath to pH<1 and extracted by CHCl₃ (3×10 mL). The extract was dried (MgSO₄) and evaporated to leave 0.54 g (98%) of 3.3 as a colorless solid (FIG. 3).

c. Synthesis of 2,5-dioxopyrrolidin-1-yl 4-azido-2,3,5,6-tetrafluorobenzoate 3.4

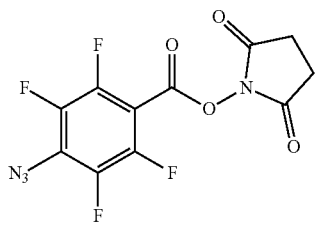 [SMILES: [N-]=[N+]=Nc1c(F)c(F)c(C(=O)ON2C(=O)CCC2=O)c(F)c1F]

Figure 4:
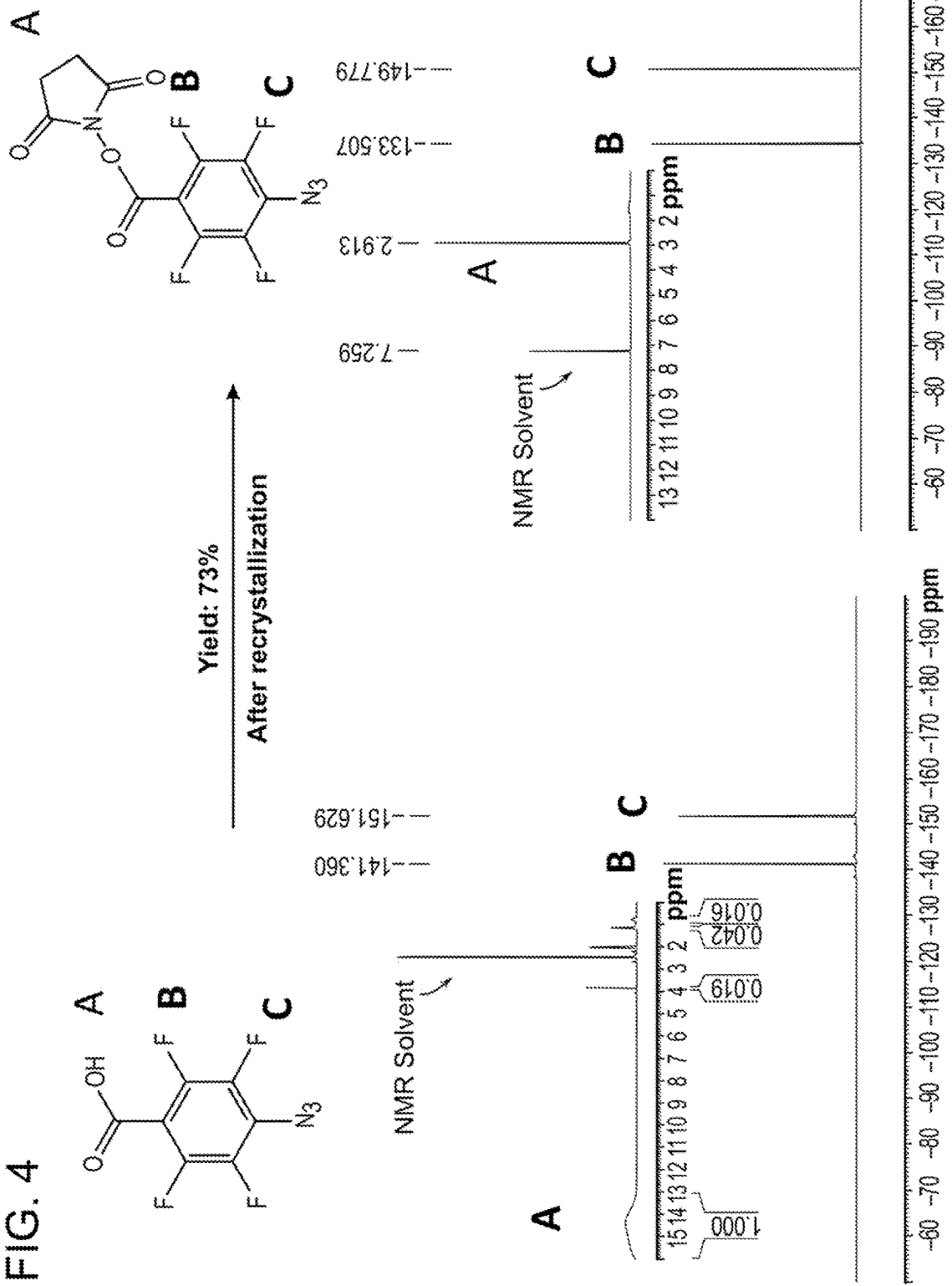
FIG. 4 shows representative spectral data confirming the synthesis of 2,5-dioxopyrrolidin-1-yl 4-azido-2,3,5,6-tetrafluorobenzoate (Scheme III, 3.4).

A solution of 234 mg (1.0 mmol) of 3.3 (115 mg, 1.0 mmol) of N—hydroxysuccinimide (NHS) and 211 mg (1.02 mmol) of dicyclohexylcarbodiimide (DCC) in CH₂Cl₂ (6.5 mL, redist.) was stirred at 25° C. overnight. The mixture was filtered. The filtrate was evaporated to leave 331 mg (99%) of 3.4 as a colorless solid (FIG. 4).

d. Synthesis of PFPA-PEG₅₀₀₀

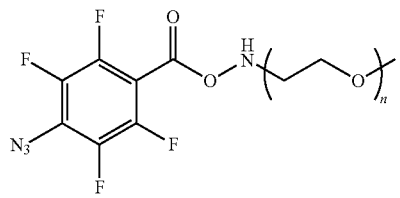

Figure 5:
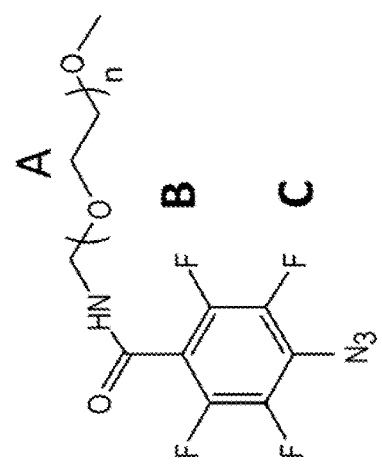
FIG. 5 shows representative spectral data confirming the synthesis of PFPA-PEG$_n$.
Figure 5:
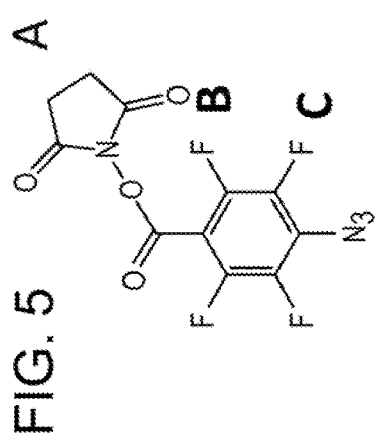
Figure 5:
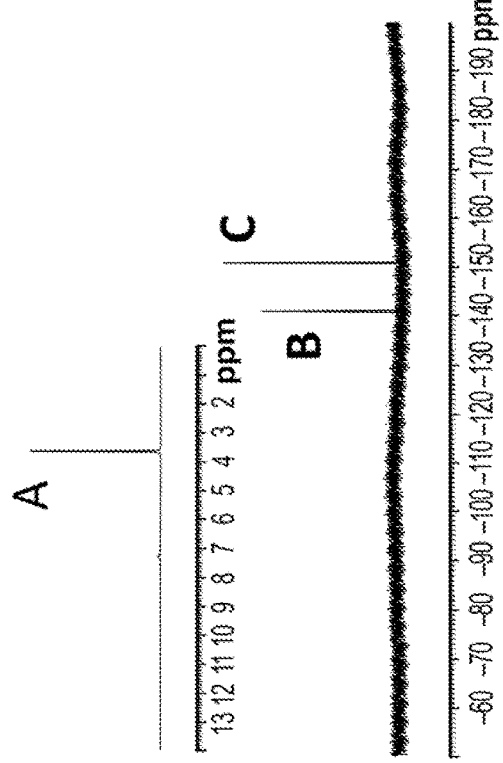
Figure 5:
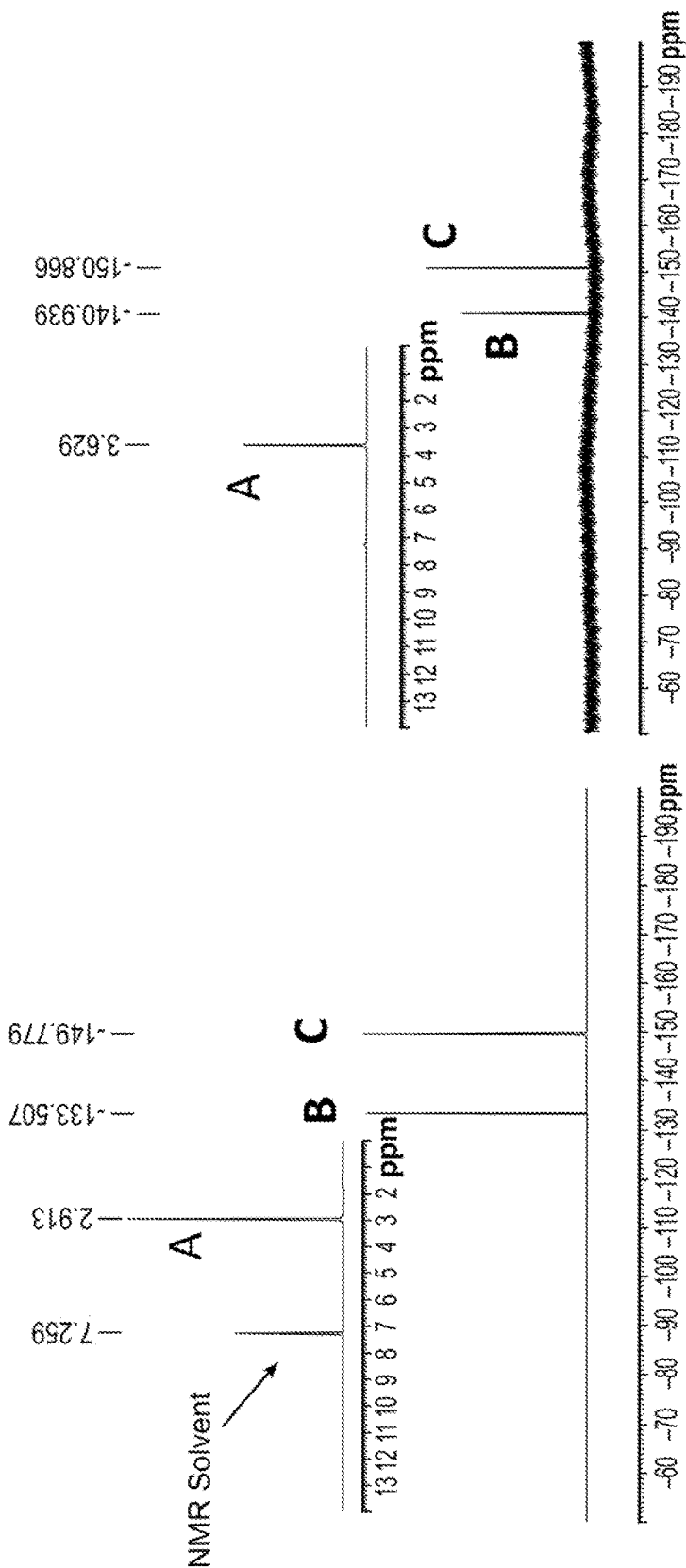
Figure 6:
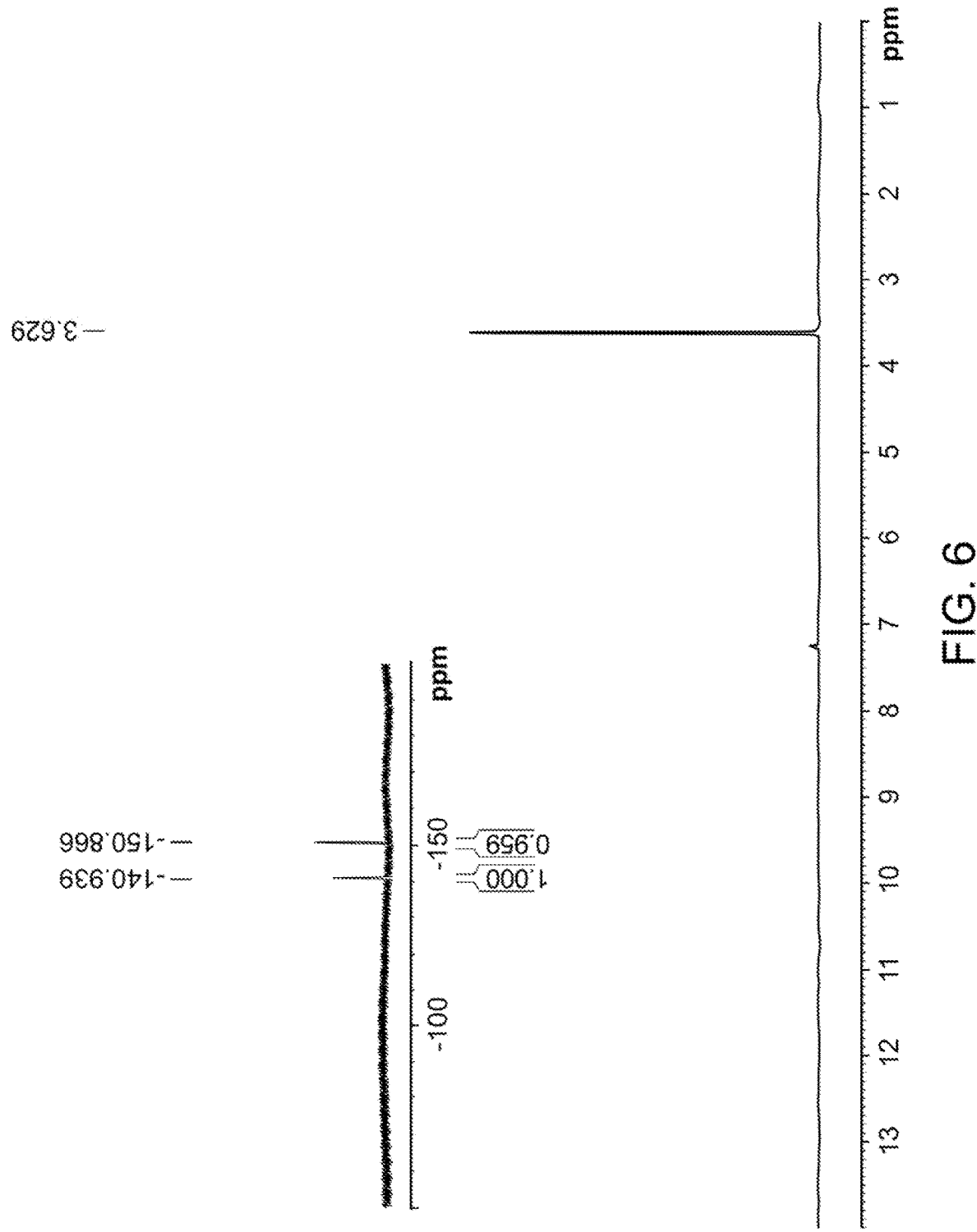
FIG. 6 shows representative 41 and $^{19}$F (inset) NMR spectral data of PFPA-PEG$_{5000}$.

H₂N—PEG₅₀₀₀ (750 mg, 0.15 mmol) was dissolved in 10 mL of CHCl₃. 3.4 (60 mg, 0.18 mmol) was added to solution and the reaction was allowed to stir in the dark overnight at room temperature. The resulting solution was poured into 20 mL of diethyl ether and the product was extracted 3 times with 20 mL DI water. A grey solid product (745 mg, 0.14 mmol, yield: 93%) was obtained via evaporation under reduced pressure and stored in a dessicator in the dark before use (FIGS. 5 and 6). ¹H NMR 300 MHz, CDCl₃, 25° C., solvent reference peak): δ=3.63 (m); ¹⁹F NMR 300 MHz, CDCl₃, 25° C., solvent reference peak): δ=−140.94 (2F; aryl—F), −150.87 (2F; aryl—F); IR: $\tilde{v}$=2876, 2102, 1933, 1460, 1337, 1275, 1233, 1101, 950, 836 cm¹.

e. Synthesis of PFPA-PEG₁₀₀₀

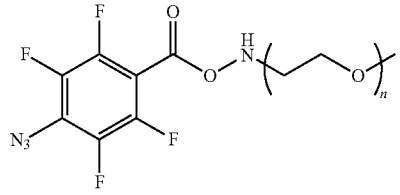

Figure 7:
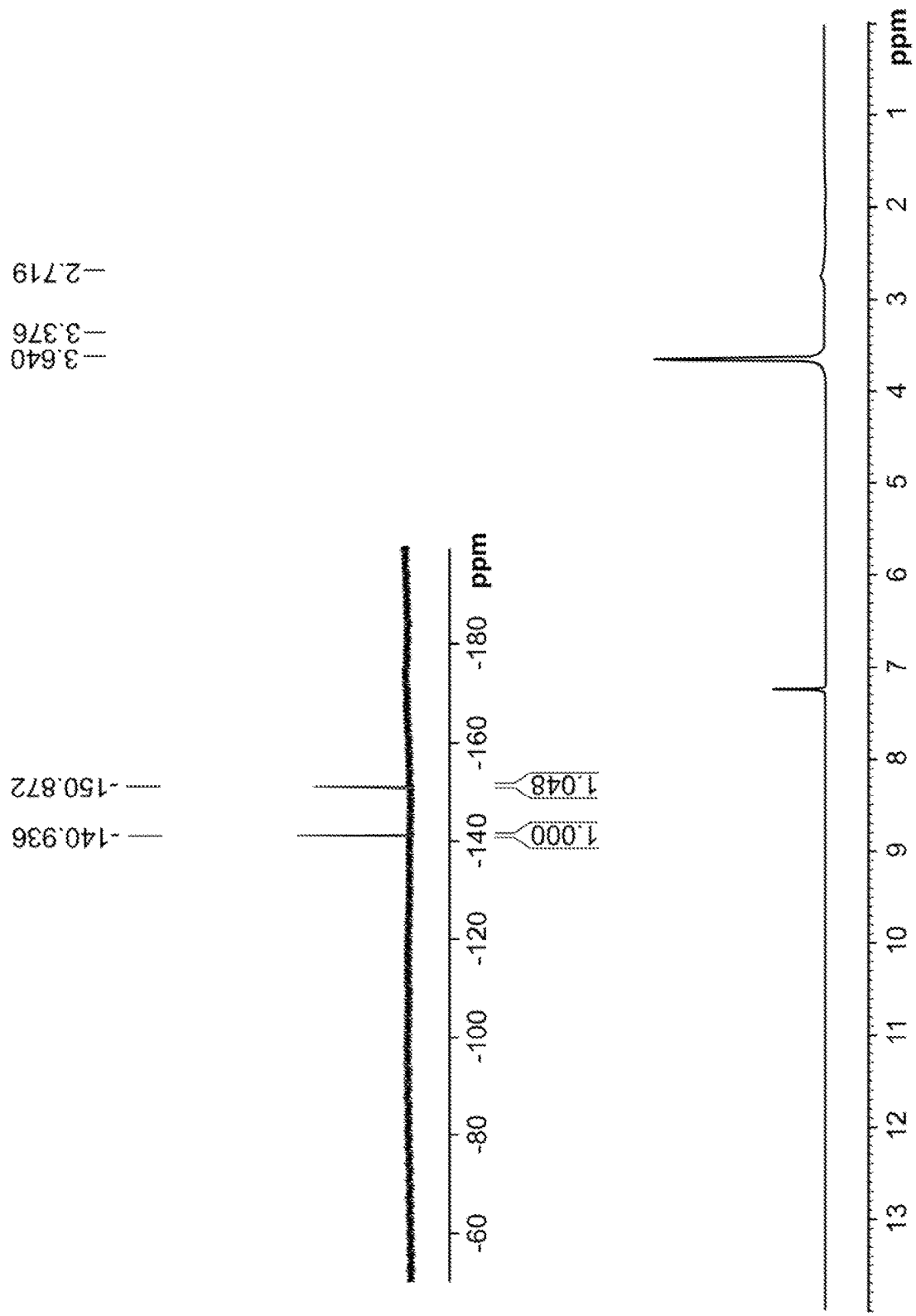
FIG. 7 shows representative 41 and $^{19}$F (inset) NMR spectral data of PFPA-PEG$_{1000}$.

H₂N—PEG₁₀₀₀ (820 mg, 0.82 mmol) was dissolved in 10 mL of CHCl₃. 3.4 (302 mg, 0.91 mmol) was added to solution and the reaction was allowed to stir in the dark overnight at room temperature. The resulting solution was poured into 20 mL of diethyl ether and the product was extracted 3 times with 20 mL DI water. A white wax (981 mg, 0.8 mmol, yield: 97%) was obtained via evaporation under reduced pressure and stored in a dessicator in the dark before use (FIG. 7). ¹H NMR 300 MHz, CDCl₃, 25° C., solvent reference peak): δ=3.64 (m), 3.38 (s), 2.72 (s); ¹⁹F NMR 300 MHz, CDCl₃, 25° C., solvent reference peak): δ=−140.94 (2F; aryl—F), −150.87 (2F; aryl—F); IR: $\tilde{v}$=2860, 2120, 1714, 1484, 1342, 1276, 1210, 1090, 990, 940, 839 cm⁻¹.

f. Synthesis of PFPA-PEG₅₅₀

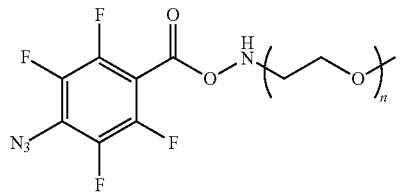

Figure 8:
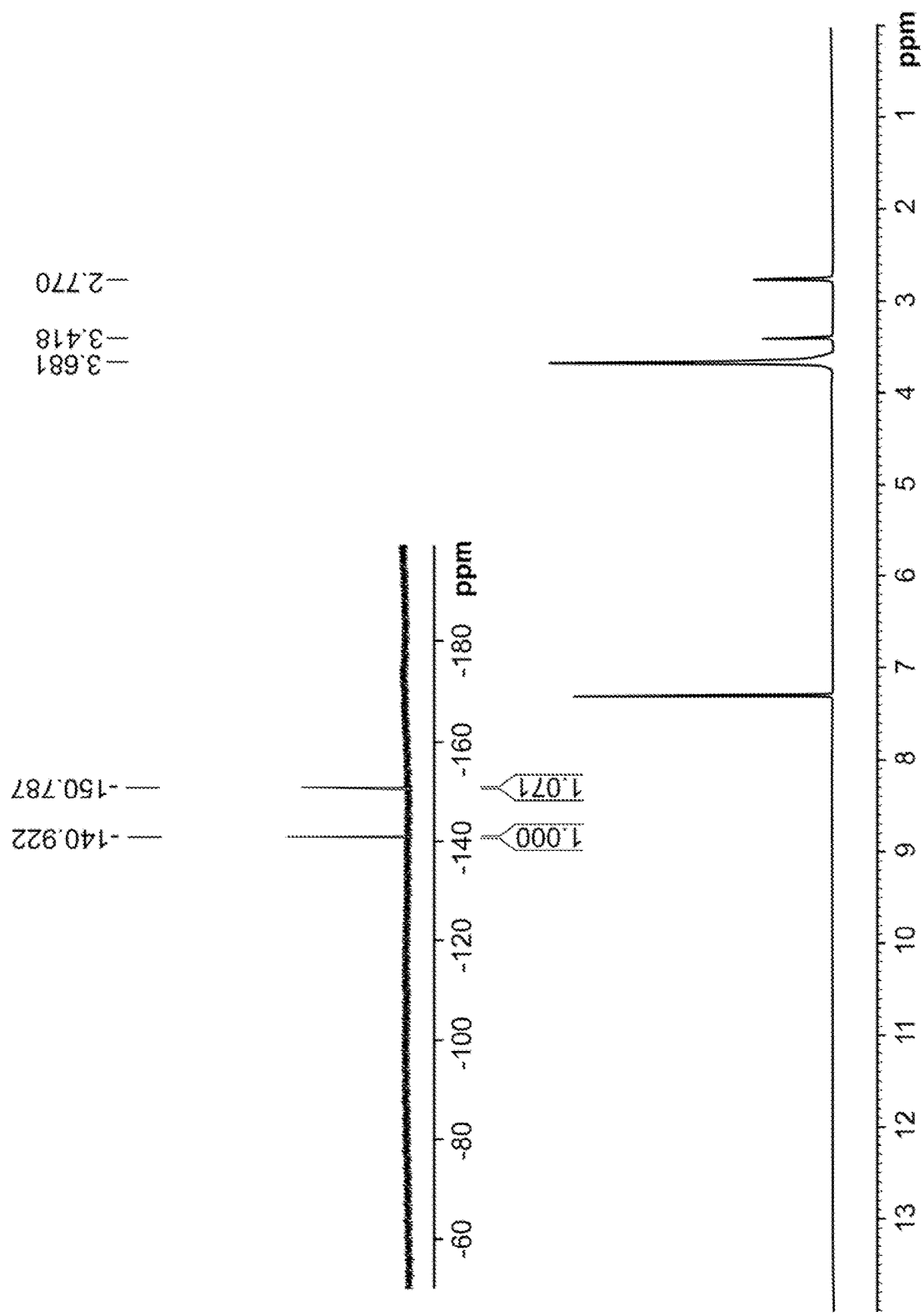
FIG. 8 shows representative 41 and $^{19}$F (inset) NMR spectral data of PFPA-PEG$_{550}$.

H₂N—PEG₅₅₀ (270 mg, 0.5 mmol) was dissolved in 5 mL of CHCl₃. 3.4 (180 mg, 0.54 mmol) was added to solution and the reaction was allowed to stir in the dark overnight at room temperature. The resulting solution was poured into 20 mL of diethyl ether and the product was extracted 3 times with 20 mL DI water. A light yellow oil (373 mg, 0.47 mmol, yield: 94%) was obtained via evaporation under reduced pressure and stored in a dessicator in the dark before use (FIG. 8). $^1$H NMR 300 MHz, CDCl$_3$, 25° C., solvent reference peak): δ=3.68 (m), 3.42 (s), 2.77 (s); $^{19}$F NMR 300 MHz, CDCl$_3$, 25° C., solvent reference peak): δ=−140.92, −150.79. IR: ν⁻=2861, 2122, 1771, 1482, 1316, 1254, 1205, 1085, 988, 821 cm$^{-1}$.

3. Synthesis of Hydrophilic Small Molecules

Three small molecules bearing hydrophilic acidic and basic functionalities were synthesized. All compounds were prepared from the commercially available precursors and converted using common reagents.

g. Synthesis of Sodium 4-azido-2,3,5,6-tetrafluorobenzoate PFPA—COON$_A$

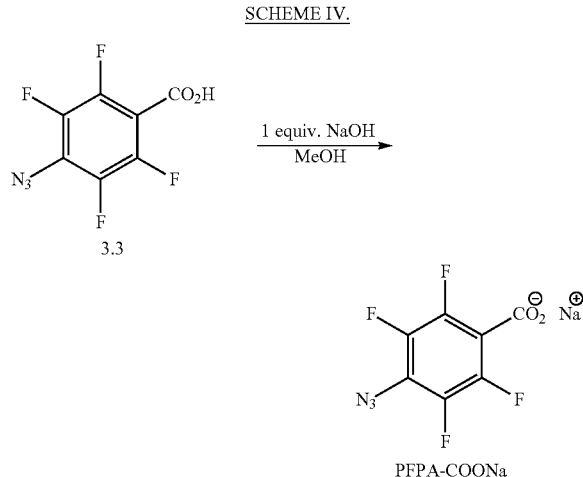

PFPA-COONa

PFPA—COONa was prepared from the corresponding carboxylic acid (PFPA—COOH, Keana, J. F. W., and Cai, S. X. (1990) *J. Org. Chem.* 55, 3640-3647) using 1 molar equivalent of sodium hydroxide in methanol. The sodium salt form enables the dissolution in water.

h. Synthesis of Sodium 4-azido-2,3,5,6-tetrafluorobenzenesulfonate PFPA—SO$_3$N$_A$

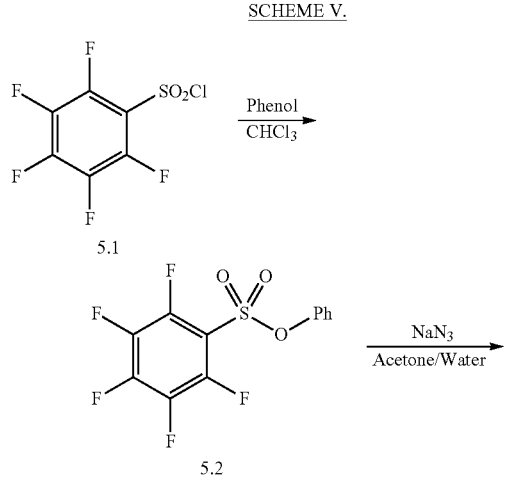

PFPA-SO$_3$Na

Because carboxylic acid functionalities are known to chelate ions in solution that can lead to scaling, the PFPA-sulfonate salt was synthesized. The sulfonyl chloride group must first be protected with phenol, prior to addition of the azide (step 2). Sulfonate esters protected with aliphatic alcohols are unstable toward nucleophilic attack, as in step 3 (Miller, S. C. (2010) J. Org. Chem. 75, 4632-4635). Finally, deprotection of the sulfonate afforded a solid which was isolated via filtration.

i. Synthesis of 4-azido-N—(2-(dimethylamino)ethyl)-2,3,5,6-tetrafluorobenzenesulfonamide PFPA-SDEA

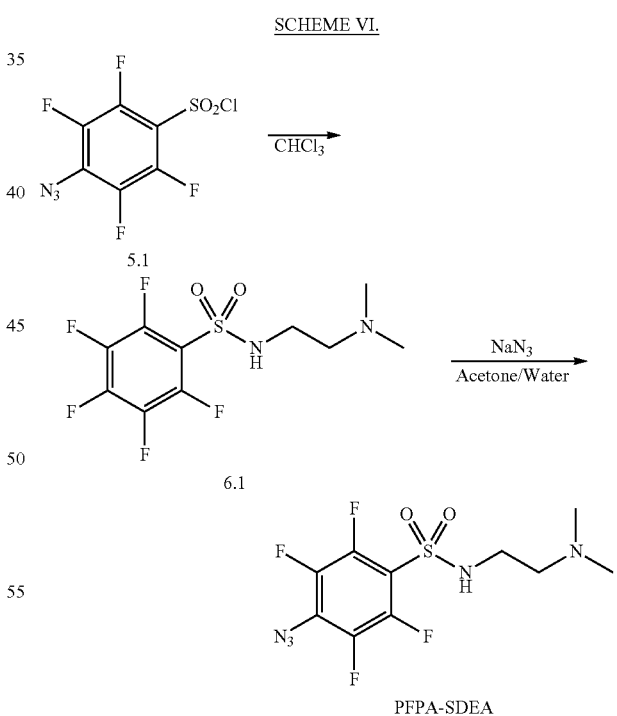

PFPA-SDEA

PFPA-SDEA was selected for its basic functionality and ease of synthesis. Additionally, the tertiary dimethyl amine tail has been reported to exhibit antimicrobial properties (Martin, T. P., et al. (2007) *Biomaterials* 28, 909-915). The PFPA-SDEA is organosoluble, but can also be converted to its salt form with addition of an acid. PFPA—COOH (or PFPA-SDEA) can be added together at equimolar ratios, dissolving in H₂O in the salt form (PFPA-SDEAH+ or PFPA—COO–, respectively).

j. Synthesis of 2-(((4-Azido-2,3,5,6-tetrafluorobenzoyl)oxy)amino)—N,N—dimethylethanamine PFPA-CDEA

SCHEME VII.

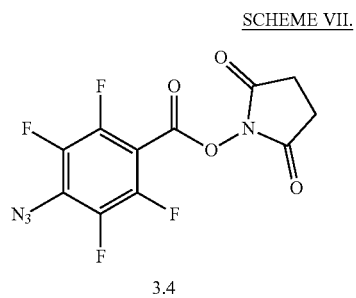

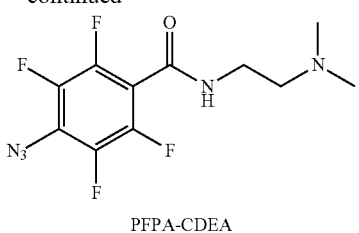

PFPA-CDEA was prepared from the PFPA ester prepared as disclosed herein above. Thus, reaction with N1,N1-dimethylethane-1,2-diamine in the presence of chloroform afforded the desired PFPA analog (FIG. 9).

k. Prophetic Synthesis of Zwitterionic PFPA Derivatives

SCHEME VIII.

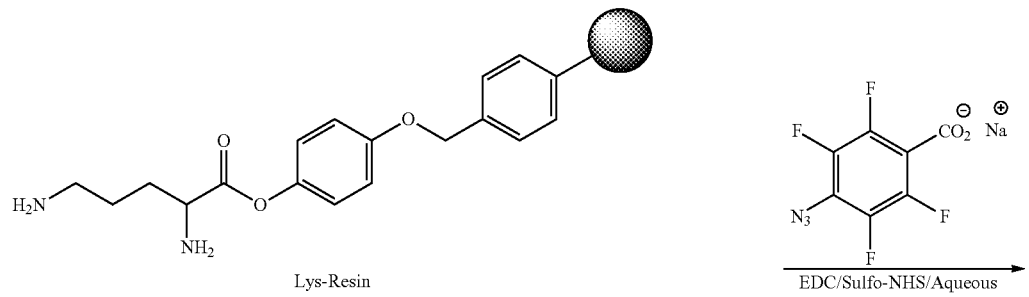

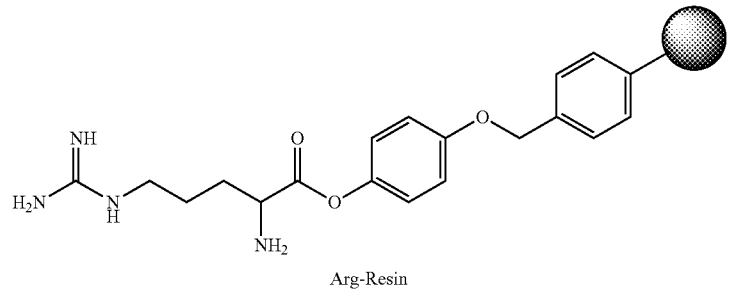

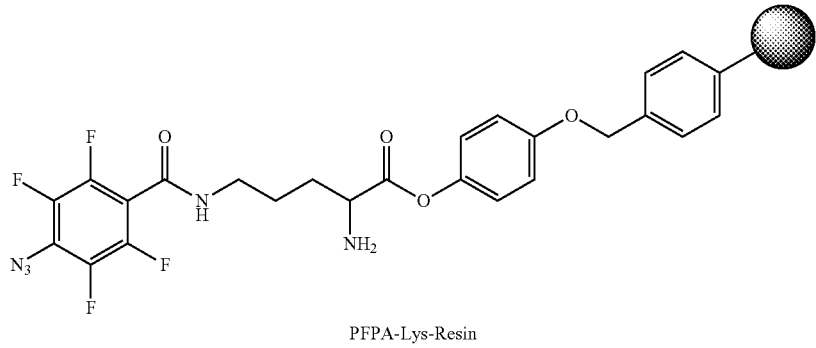

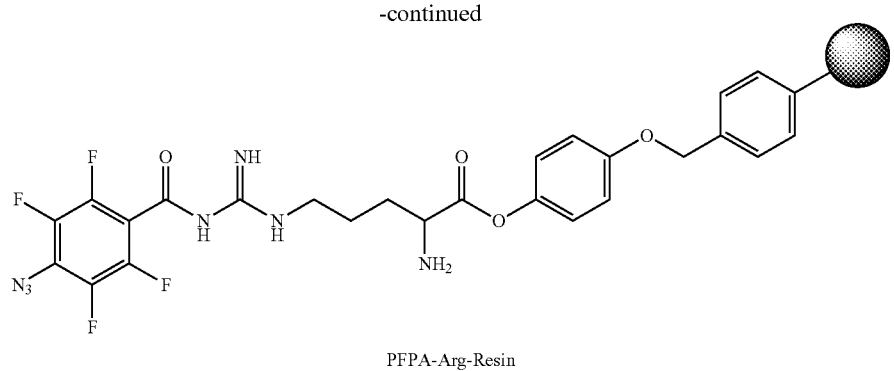

PFPA-Arg-Resin

TFA/H₂O

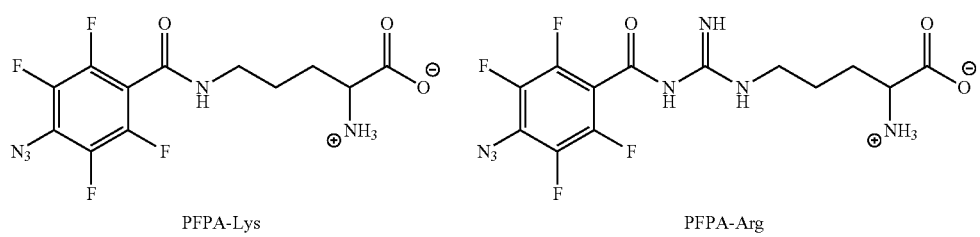

PFPA-Lys                    PFPA-Arg

The synthesis of zwitterionic PFPA derivatives poses synthetic challenges due to the limited solubility of zwitterions in organic solvents. For the cationic and anionic derivatives, the target compounds may be synthesized in an organic solvent system, using the activated PFPA-N—succinimidyl ester or sulfonyl chloride. Therefore, water soluble carbodiimide chemistry (i.e., 1-ethyl-3-(3-dimethylaminopropyl)carbodiimide) must be utilized to couple the zwitterionic compounds bearing a primary amine to the free carboxylic acid PFPA—COOH derivative (Nakajima, N., Ikada, Y. (1995) *Bioconjugate Chemistry* 6, 123-130). Thus, in one prophetic example, PFPA coupling can be performed using amino acid functionalized resins, analogous to solid phase peptide synthesis (SPPS) (Merrifield, R. N. (1963) *J. Am. Chem. Soc.* 65, 2149). SPPS enables robust reaction efficiency and facile work-up by covalently coupling the PFPA to the selected compound that is attached to an insoluble functionalized resin. The coupling reagents can be washed away after completion of the reaction and the pure product attained with selective cleaving agents. The amino acids lysine (Lys) and arginine (Arg) will be selected due to their free amino group on the side chain, which should enable these compounds to be coupled to PFPA—COOH efficiently.

4. Surface Modification Procedure

SCHEME IX.

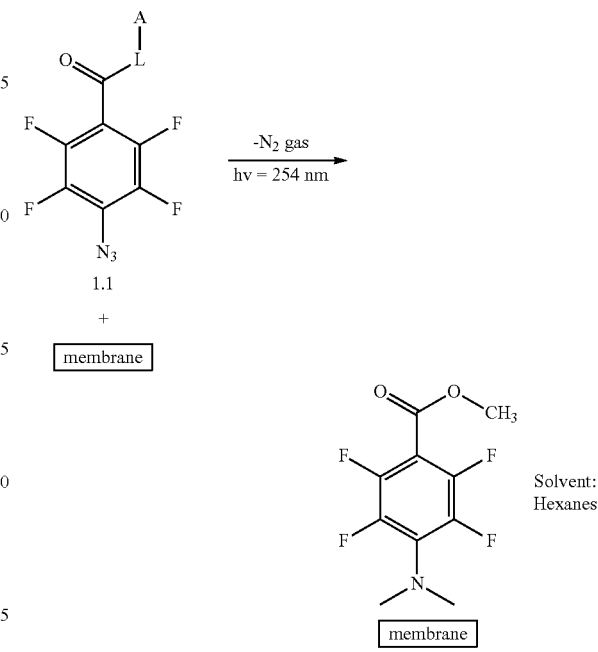

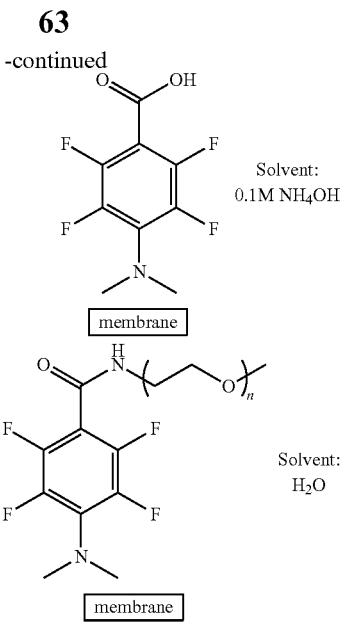

Figure 10:
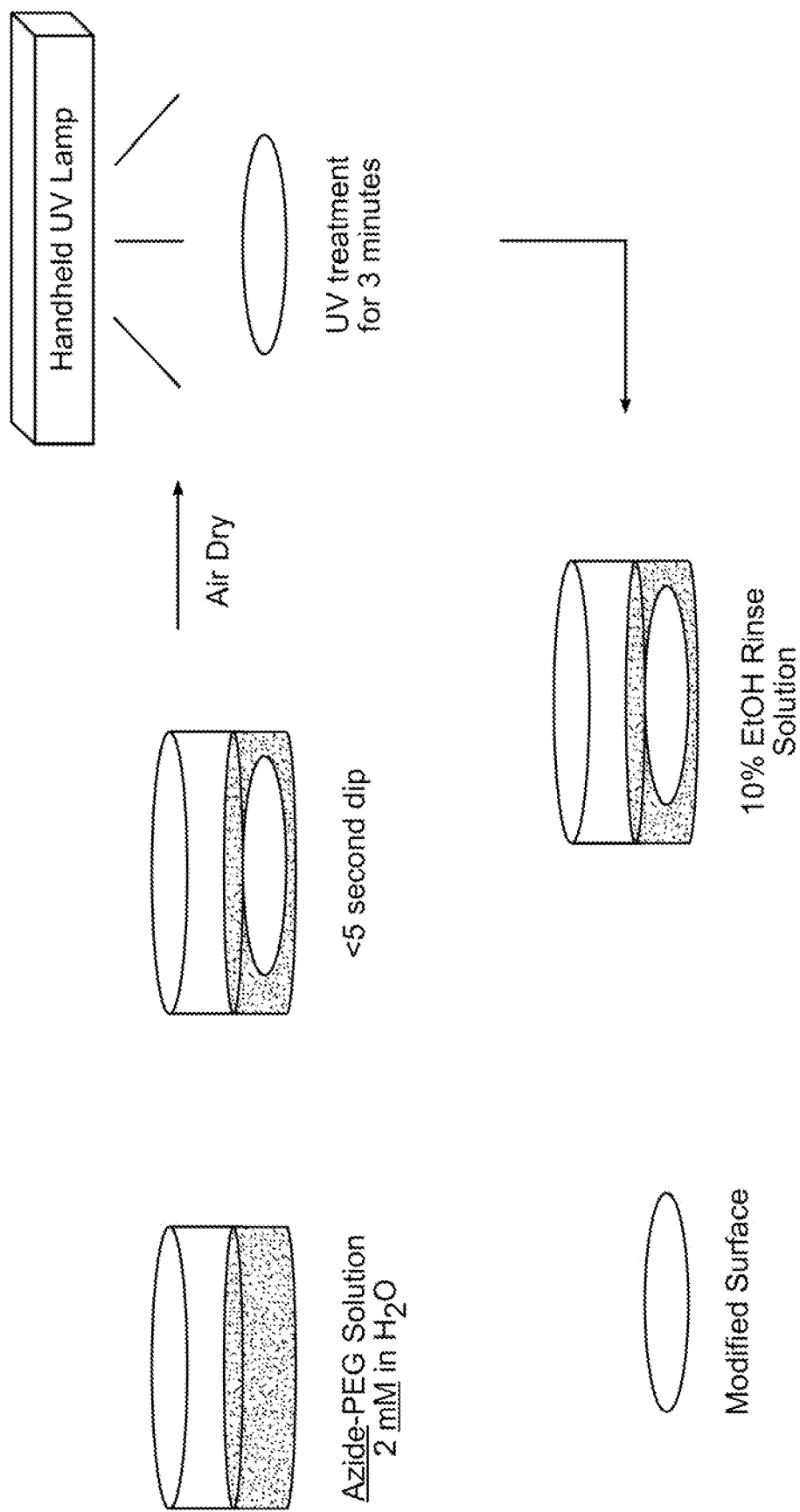
FIG. 10 shows representative data pertaining to the modification of commercial membrane coupons via dip-coating and treatment with UV light.

A diagram illustrating the procedure used to modify the membrane surface is shown in FIG. 10. A 2 mM PFPA-PEG$_n$ solution was prepared by dissolving PFPA-PEG$_n$, PFPA—COONa, or PFPA—SO$_3$Na in 18 MΩ water and shaking vigorously until the PFPA-PEG was fully dissolved. All dip-coating solutions were used the same day as prepared. The commercial reverse osmosis membrane coupons (2×2 cm$^2$) were dipped into the solutions for ~5 seconds and allowed to air dry on a flat surface overnight. Larger 110 cm$^2$ samples were used for performance testing. Once dried, the coupons were placed under a 6W Spectroline ENF-260C handheld UV lamp using a 254 nm wavelength for 3 minutes. The lamp was held 5 inches above the surface of the membrane using a ring stand. After UV exposure, the membrane cutouts were placed in a 10% ethanol/water bath stream to remove by-products and any unreacted azide. The ethanolic solution also helped to restore permeability to the membranes that was lost during the drying step. The membrane coupons were then placed in a DI water bath overnight. Membrane coupons used for ATR-IR and contact angle measurements were stored in a dessicator.

5. Membrane Characterization

3×1 cm membrane coupons used for FT-IR, contact angle measurements, and atomic force microscopy (AFM) were dried before use overnight in a dessicator. The modified and unmodified membranes were characterized with ATR-IR on a JASCO FT/IR-6300 spectrometer with an ATR accessory. XPS studies were carried out on a Kratos AXIS Ultra DLD with a monochromatic Al Kα X-ray source operating at 10 mA and 15 kV. Survey spectra and individual high-resolution spectra were collected using pass energies of 160 eV and 10 eV, respectively. Data processing was performed using CasaXPS 2.3 software, and spectra binding energies were calibrated by assigning the hydrocarbon peak in the C is high-resolution spectra to 284.6 eV. Sessile drop contact angle measurements were observed using a Kruss DSA 10 goniometer.

6. Water Permeability and Rejection

Performance testing on the RO membranes was conducted in a stainless-steel dead-end filtration stirred cell (Sterlitech Corp., Kent, Wash.) with an active membrane area of approximately 110 cm$^2$. The stirred cell was filled with Milli-Q water, and pressurized until water flow through the membrane was first observed. The water flow rate was then recorded using a digital flow meter (FlowCal 5000, Tovatech LLC, South Orange, N.J.). The system was continually pressurized at increments of 50 psi (689 kPa) up to 400 psi (2758 kPa) while measuring the water flow rate at each increment. The membrane was then allowed to compact at 400 psi until the flow rate stabilized, which took approximately 3 hours for each membrane. The salt rejection of each membrane was characterized by filling the stirred cell with a 2 g/L NaCl solution and pressurizing the cell to 225, 300 and 400 psi. Approximately 10 mL of the permeate solution was collected at each pressure and the conductivity was measured using a calibrated conductivity meter (Accumet XL30, Fisher Scientific). The salt rejection, R, was calculated by $R=1-c_p/c_b$, where $c_p$ is the permeate concentration and $c_b$ is the bulk feed solution concentration. The pure water permeability was determined from the slope of the linear regression line on the plot of membrane water flux (flow rate normalized by membrane area) against the pressure up to 400 psi after compaction.

7. Cell Adhesion Test

Adhesion tests were performed for the membranes following a modified procedure reported by Gleason and co-workers (Yang, R. et al. (2011) *Chem. Mater.* 23, 1263-1272). *Escherichia coli* was used as the model bacteria for this test. Pure bacterial cell cultures were suspended in Luria-Bertani (LB) broth and grown at 35° C. while being shaken at 150 rpm and incubated until a mid-exponential phase was reached, at which time the cells were harvested by centrifugation at 3800×g for 8 min. The cells were then re-suspended with fresh LB medium to a concentration of 4×10$^7$ cells/mL. Membrane coupons, of approximately 1 cm$^2$, were incubated in this bacterial suspension for 24 hr at 25 rpm and 35° C. The coupons were then removed from the suspension and gently rinsed with fresh LB broth using a Pasteur pipette. Once rinsed, the coupons were immersed in a dye solution (SYTO 9 live/dead Baclight Bacterial Viability Kit L13152, Molecular Probes) for 15 min. The SYTO 9 solution was prepared by dissolving the contents of component A of the kit in 30 mL of sterile distillated water. After the staining was complete, the coupons were gently rinsed with fresh LB broth and imaged using a microscope (Olympus BX51 microscope) equipped with a fluorescent lamp and green/red fluorescence filters and a 4× CCD camera attachment (FVIEW-II, Soft Imaging System, USA). Surface coverage estimates were calculated using ImageJ software (Abramoff, M. D., et al. (2004) Biophotonics Int. 11, 36-42).

8. Prophetic Synthesis of Polymeric PFPA Derivatives

SCHEME X.

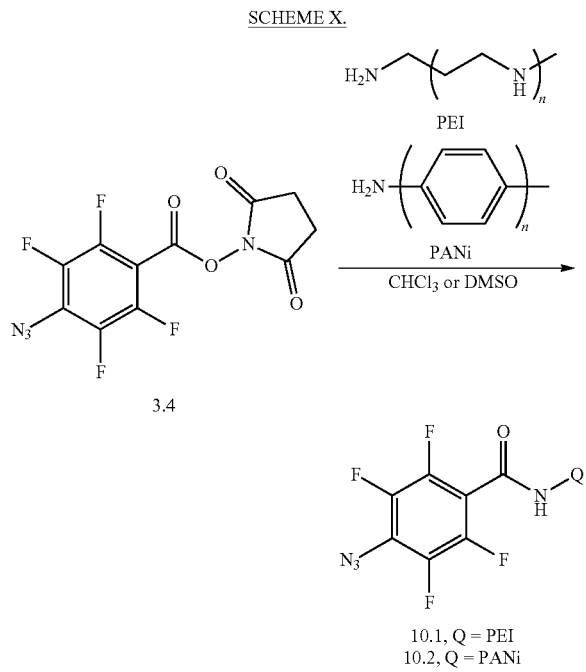

In various aspects, hydrophilic polymers with antimicrobial properties can be coupled to the PFPA anchor molecule from the N—succinimidyl ester derivative prepared as disclosed herein. For example, in one prophetic example the PFPA ester can be coupled with linear polyethyleneimine (PEI). Similar to PEG, PEI is cationic and a strong chelating agent, which allows PEI to chelate antimicrobial silver nanoparticles (Mauter, M. S., et al. (2011) *ACS Applied Materials and Interfaces* 3, 2861-2868; Madkour, T. M. (1999) *Polymer Data Handbook*, Oxford University Press, Inc.; Lee, H., et al. (2011) *Colloids and Surfaces B: Biointerfaces* 88, 505-511). Research on the attachment of PEI to PSf UF membranes by plasma grafting, followed by chelation of silver nanoparticles has demonstrated strong antimicrobial efficacy towards biological foulants (Mauter, M. S., et al. (2011) *ACS Applied Materials and Interfaces* 3, 2861-2868). In order to determine the effect on surface hydrophilicity, membrane performance, and anti-fouling properties, PEI derivatives with varying molecular weights may be used.

In another prophetic example, the PFPA ester can be coupled with polyaniline (PANi). PANi is a conjugated polymer known for its ease of synthesis (Cao, Y., et al. (1989) *Polymer* 30, 2305-2311), antimicrobial properties (Gizdavic-Nikolaidis, M. R., et al. (2011) *Acta Biomaterialia* 7, 4204-4209), and proficient acid/base doping properties (Chiang, J. C., MacDiarmid, A. G. (1986) *Synthetic Materials* 13, 193-205). Thus, PANi's hydropholicity can be tuned with changes in pH (Leng, W., et al. (2012) *J. Colloid Interf. Sci.* 369, 411-418), potentially useful as a foulant release mechanism. Due to its conjugated backbone, PANi's structures are semi-rigid (Andreatta, A., et al. (1988) *Synthetic Metals* 26, 383-389), unlike PEG and PEI, and may impart higher membrane permeability than its flexible hydrophilic counterparts. Unfortunately, the solubility of PANi is limited to polar organic solvent that will dissolve the PTF membranes during the dip-coating process. Therefore, organosoluble PANi oligomers can be coupled to the PFPA anchor that maintains PANi's unique properties without the limited solubility of the parent polymer.

G. Results and Discussion

The need for a scalable method to produce anti-fouling RO membranes led to the investigation of perfluorophenylazide as a chemical modifier (PFPA). PFPAs are known for their highly reactive azide group that allows PFPA derivatives (Levya, E., et al. (1986) *J. Am. Chem. Soc.* 108, 8307-8309; Liu, L. H., and Yan, M. (2010) *Accounts of Chemical Research* 43, 1434-1443) to make chemical bonds with rather unreactive targets, such as grapheme (Liu, L. H., and Yan, M. (2009) *Nano. Lett.* 9, 3375-3378; Liu, L. H., et al. (2010) *J. Mater. Chem.* 20, 5041-5046), carbon nanotubes (Pastine, S. J., et al. (2008), *J. Am. Chem. Soc.* 2008, 4238-4239), fullerenes (Yan, M., et al. (1994) *J. Org. Chem.* 59, 5951-5954), and organic polymers (Bartlett, M. A., and Yan, M. (2001) *Adv. Mater.* 13, 1449-1451). The azide functionality is activated by photoexcitation that expels nitrogen gas and affords a reactive singlet nitrene that inserts into —NH— and C=C bonds (Morawietz, J., and Sander, W. (1996) *J. Org. Chem.* 61, 4351-4354; Poe, R., et al. (1992) *J. Am. Chem. Soc.* 114, 5054-5067). The surface layer of RO membranes is comprised of cross-linked polyamide networks that contain these groups, thus providing a target for modification. A central goal was to develop a dip-coating technique using PFPA derivatives that confers anti-fouling properties to RO membranes and maintains the roll-to-roll manufacturing process.

Because PFPAs can be prepared with a functional ester group in the para position relative to the azide moiety, PFPAs can be readily coupled to molecules containing free amino or hydroxyl groups to make corresponding amide or ester linkages. Herein, the synthesis of three hydrophilic polyethylene glycol (PEG) brush polymers of different molecular weights (MW=550, 1000, 5000 Da) with a terminal PFPA group is described. PFPA-PEG$_{550}$, PFPA-PEG$_{1000}$, and PFPA-PEG$_{5000}$ are used to denote the respective PFPA terminated PEG derivatives according to their molecular weight. The water solubility of the PFPA-PEGs allows the product to be isolated in high purity from the starting material by using an aqueous phase extraction. More importantly, the water solubility enables RO membranes to be dipped in an aqueous solution containing the dissolved PFPA-PEG derivatives. This is attractive commercially, as many common organic solvents dissolve the underlying polysulfone layer supporting the thin-film composite membrane.

The coupling of PFPAs to several hydrophilic small molecules is also described. Small molecule modifications have many advantages over polymers. Because of their size, it is hypothesized that a higher density of small molecule PFPAs can be adsorbed to a surface, in turn causing a higher density of modification during the UV treatment step. Additionally, some hydrophilic polymers are known to hydrolyze over time and are prone to oxidation. Small molecules can be designed with hydrophilic groups that do not hydrolyze and that are stable to oxidation. Small molecules are easier to synthesize and characterize, and may allow facile screening of multiple compounds against model foulants in aquatic systems.

1. Covalent Modifications of RO Membranes Via PFPA Photochemical Reactions

Figure 11:
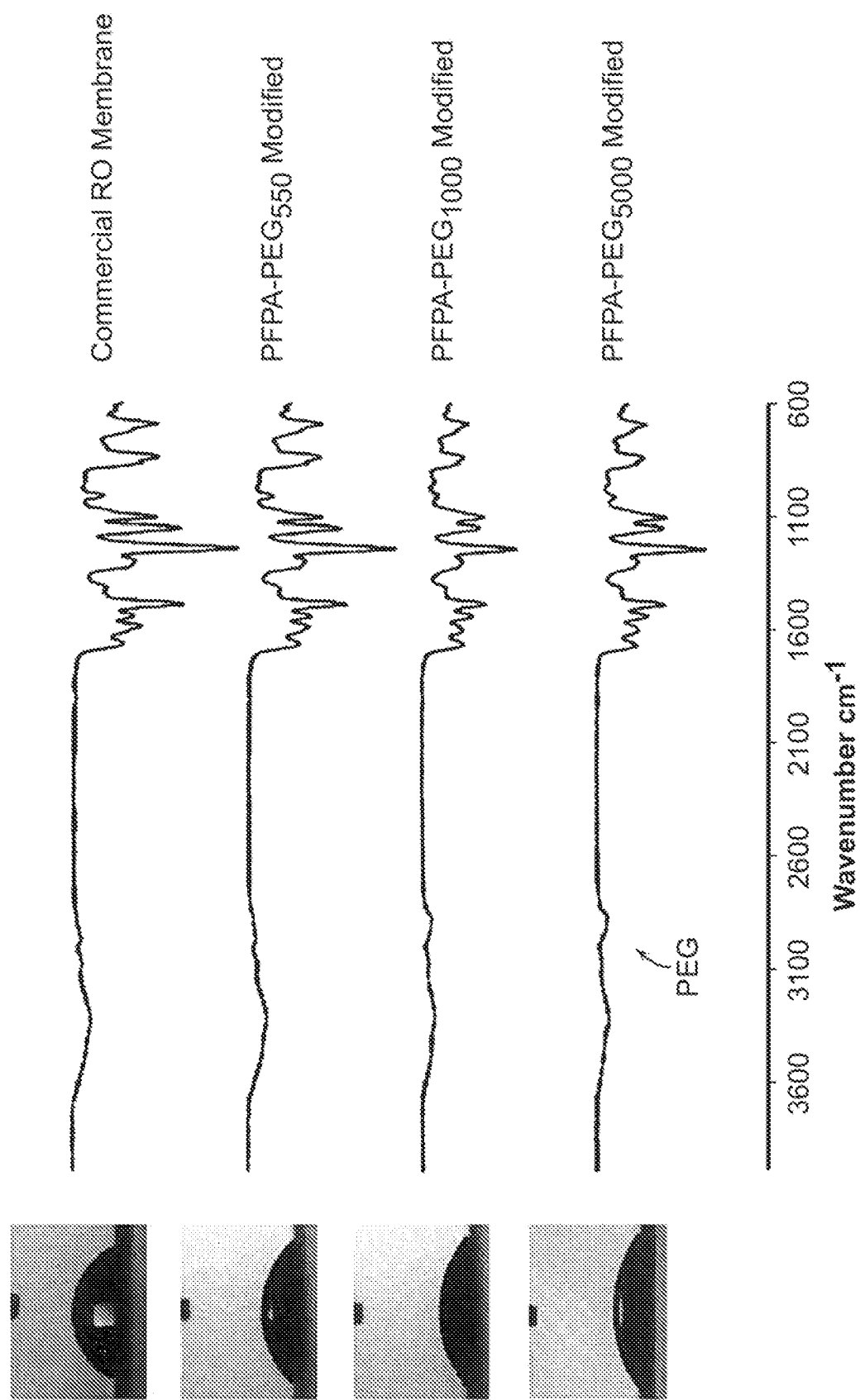
FIG. 11 shows representative data confirming that the RO membrane is either unmodified (top) or covalently bound to a PFPA-PEG$_{550}$, PFPA-PEG$_{1000}$, or PFPA-PEG$_{5000}$ moiety.

To test if PFPA photochemical reaction can covalently modify RO membranes, commercial PA membrane cutouts were dipped into aqueous solutions containing PFPA-PEG$_{550}$, PFPA-PEG$_{1000}$, and PFPA-PEG$_{5000}$ and allowed to air dry under ambient conditions. Once dried, the coupons were irradiated with low power UV light (254 nm) from a handheld UV lamp. The cutouts were rinsed in a water bath to remove any unreacted azide and dimerized byproducts from the surface and dried before surface analysis. The membranes were then characterized with ATR-IR spectroscopy. The presence of alkane groups within the PEG polymer brushed is discernible in the ATR-IR spectrum when compared to a bare PA membrane (FIG. 11). A broad C—H stretch is observed at 2860 cm$^{-1}$ and becomes stronger when PFPA-PEG of higher molecular weight is used for the modification.

Figure 12:
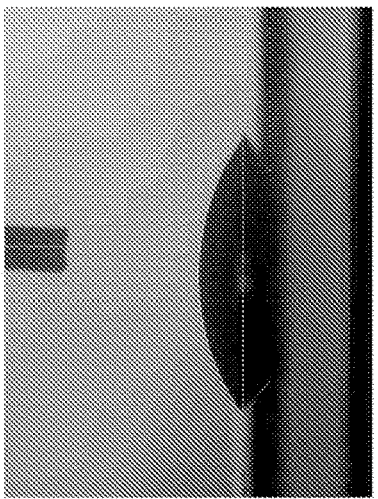
FIG. 12 shows representative data pertaining to the contact angles of RO membranes covalently bound to PFPA moieties.
Figure 12:
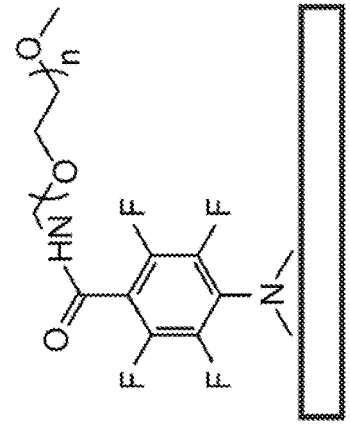
Figure 12:
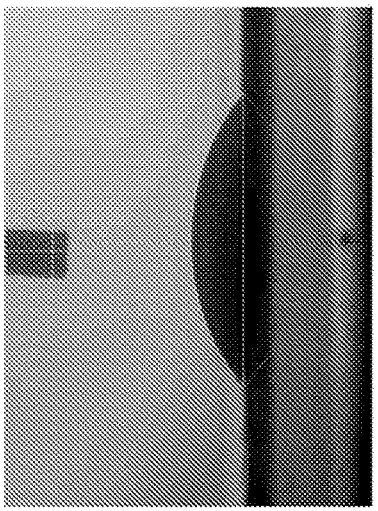
Figure 12:
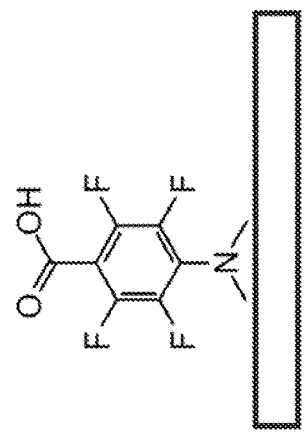
Figure 12:
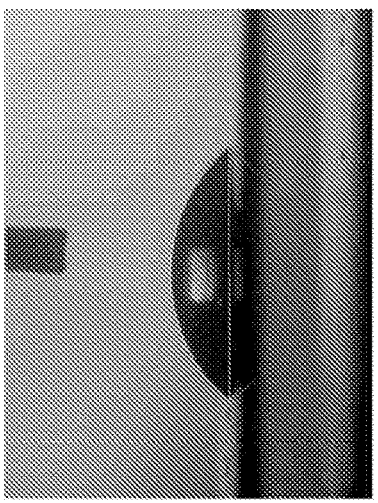
Figure 12:
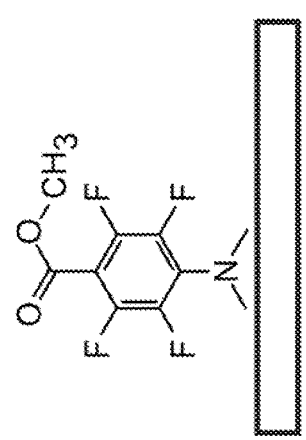
Figure 13:
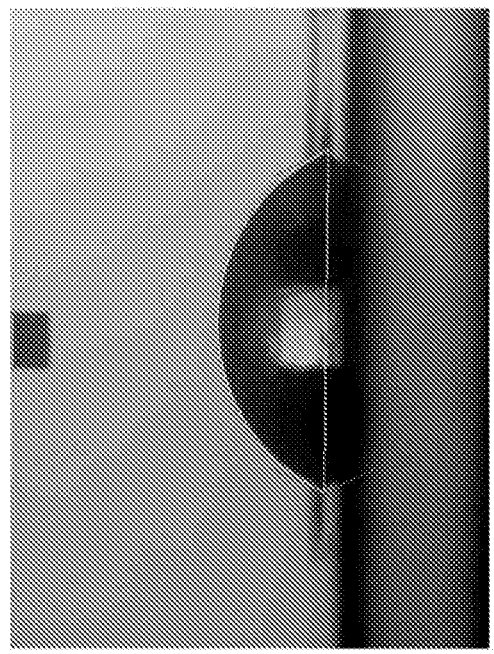
FIG. 13 shows representative data demonstrating the contact angles of an unmodified membrane before (left) and after (right) treatment with a UV light.
Figure 13:
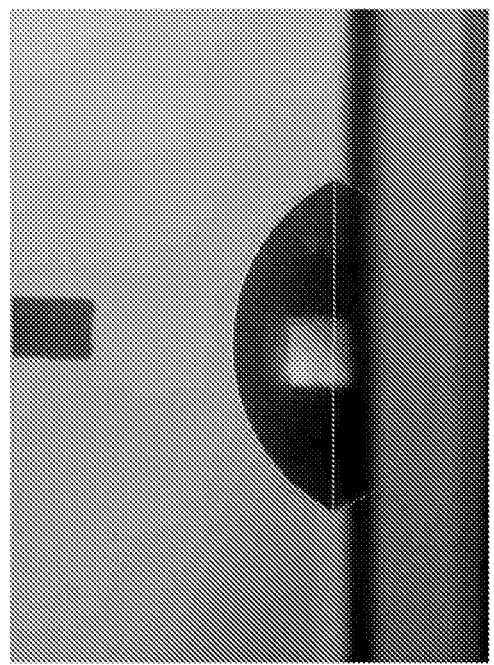
Figure 14:
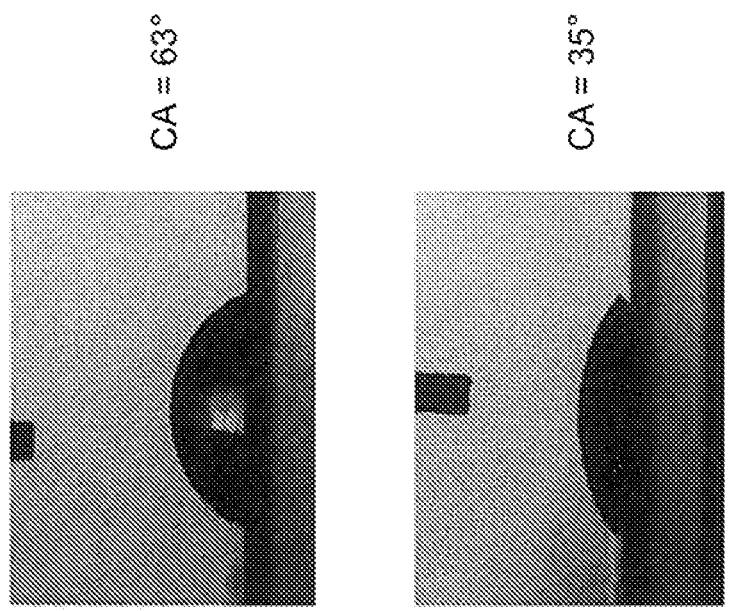
FIG. 14 shows representative data demonstrating the effect of UV exposure on a bare membrane (top) and PFPA-PEG$_{5000}$ coated membrane.
Figure 14:
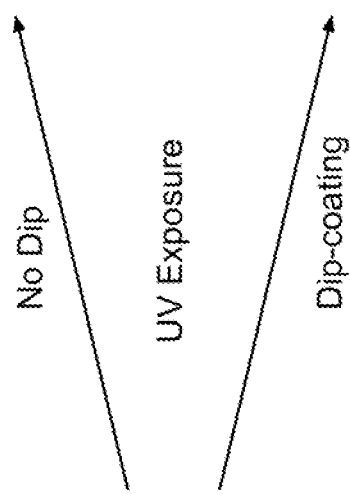
Figure 14:
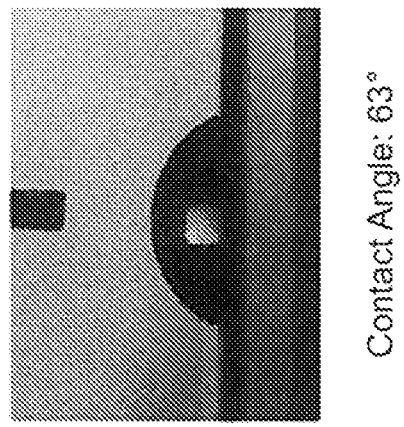

The modification is further manifested through contact angle measurements shown in the photos in FIGS. 11 and 12. The introduction of hydrophilic brush polymers to the surface of the membrane reduces the liquid/solid interfacial energy between a drop of water and top PA layer. The hydrophilic surface has a stronger interaction with water than the bare membrane, resulting in a decreased contact angle. A bare commercial membrane was also dried and exposed to UV light (no dip-coating) to confirm that the decreased contact angle was not caused by UV irradiation (FIGS. 13 and 14).

Figure 15A:
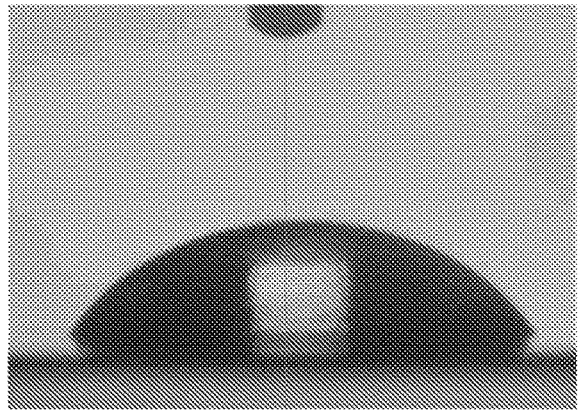
FIG. 15A shows representative data pertaining to the contact angles of an unmodified membrane.
Figure 15B:
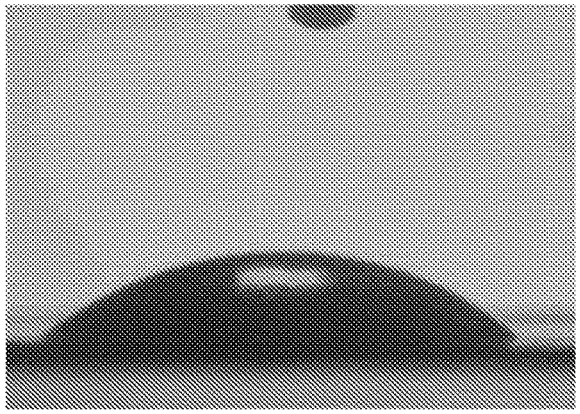
FIG. 15B shows representative data pertaining to the contact angles of a membrane modified with basic functional groups.
Figure 15C:
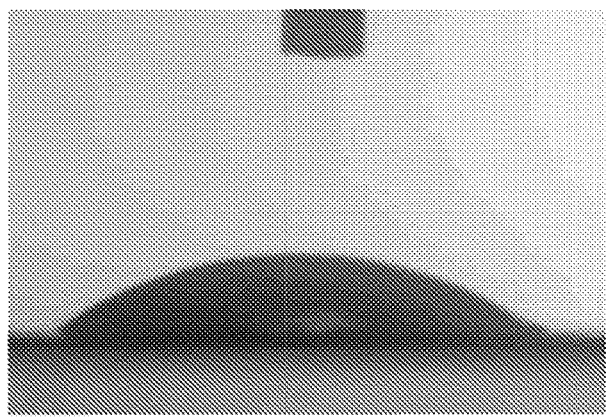
FIG. 15C shows representative data pertaining to the contact angles of a membrane modified with acidic functional groups.
Figure 15D:
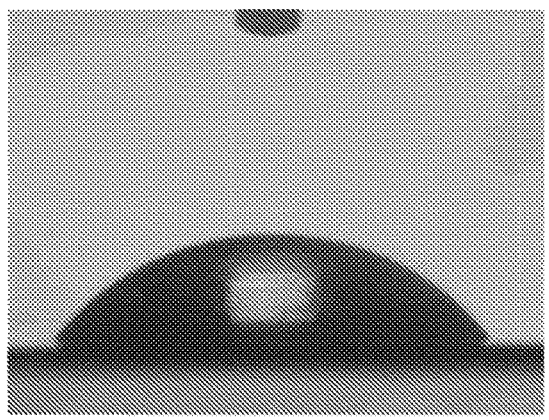
FIG. 15D shows representative data pertaining to the contact angles of a membrane modified with acidic functional groups.

A large drop in contact angle was observed for the membranes modified with basic functional groups (PFPA—COONa and PFPA—SO$_3$Na) compared with the unmodified membrane (FIG. 15A-C). In contrast, the PFPA-SDEA modified membrane maintained a similar contact angle when compared to the control membrane because the N,N—dimethylethylamine tail is hydrophobic (FIG. 15D).

Figure 16:
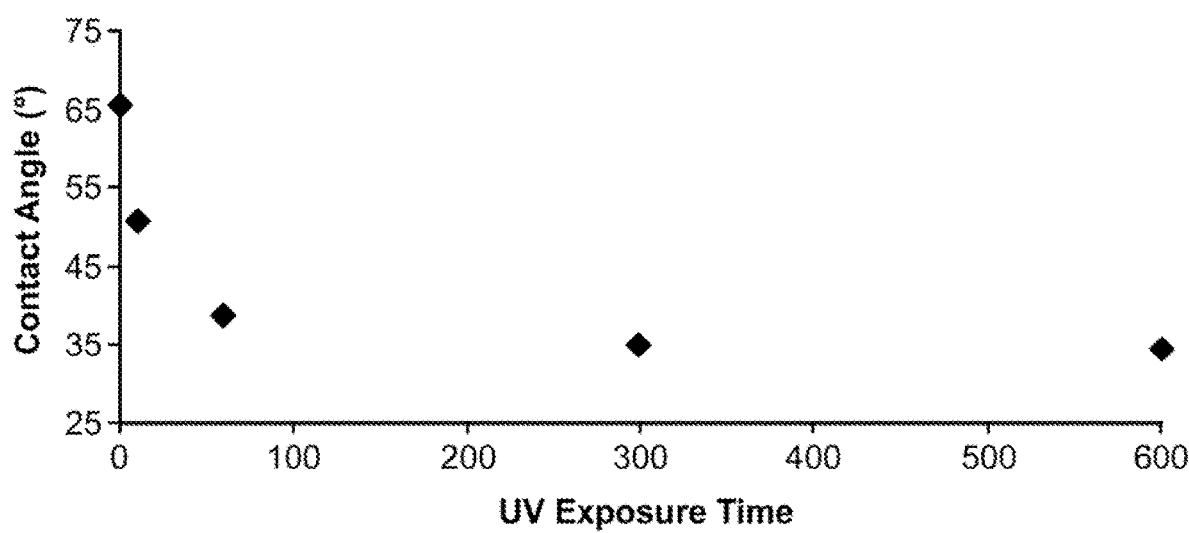
FIG. 16 shows representative data demonstrating the change in contact angle as a function of UV exposure time for a PFPA-PEG$_{5000}$ coated membrane.

2. UV Exposure Generates Covalent Bonding Between the Membrane Surface and the PFPA Moiety The contact angle was measured as a function of UV exposure time to investigate reaction completion (FIG. 16). Several 4 cm$^2$ membrane cutouts were dip-coated in PFPA-PEG$_{5000}$, exposed to UV light for different lengths of time, and rinsed. The results shown in FIG. 16 indicate that the reaction is complete after ~60 seconds of UV exposure time. It is also important to note that with zero UV exposure time, the contact angle of the bare commercial membrane is restored at 63°. This indicates that the wash step removes essentially all the physically adsorbed PFPA-PEG from the surface of the membrane. Thus, without wishing to be bound by theory, UV exposure generates covalent bonding between the RO membrane surface and the PFPA functionality.

3. X-Ray Photoelectron Spectroscopy

Figure 17A:
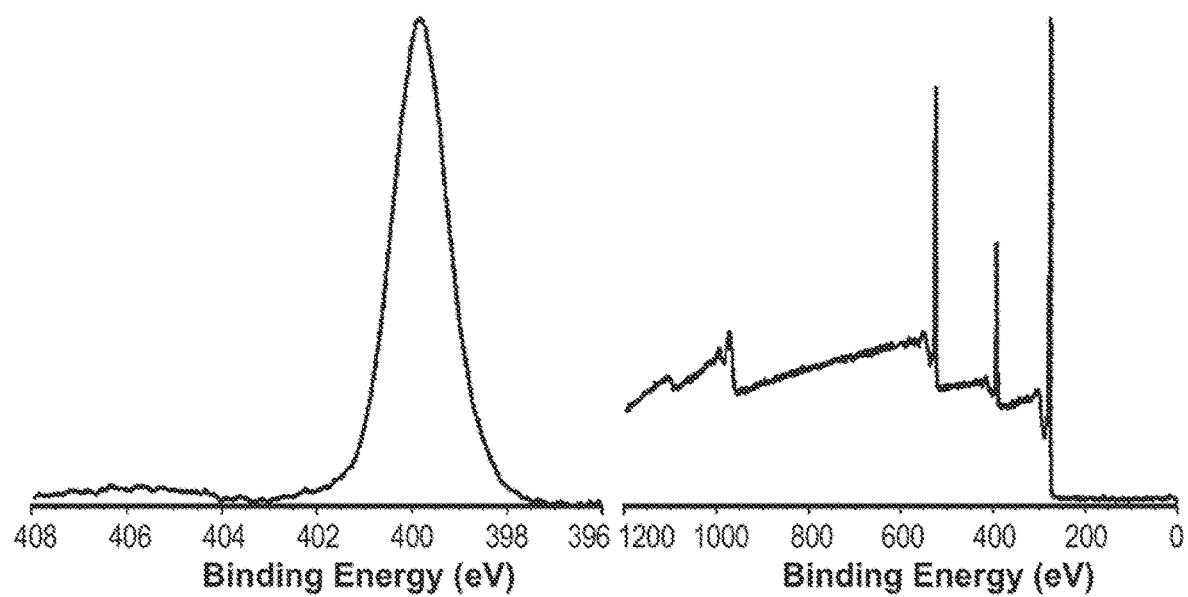
FIG. 17A shows representative data pertaining to the covalent attachment of PFPA to the surface of the membrane. Specifically, the XPS survey spectra and N is spectra of the unmodified RO membrane surface is shown.
Figure 17B:
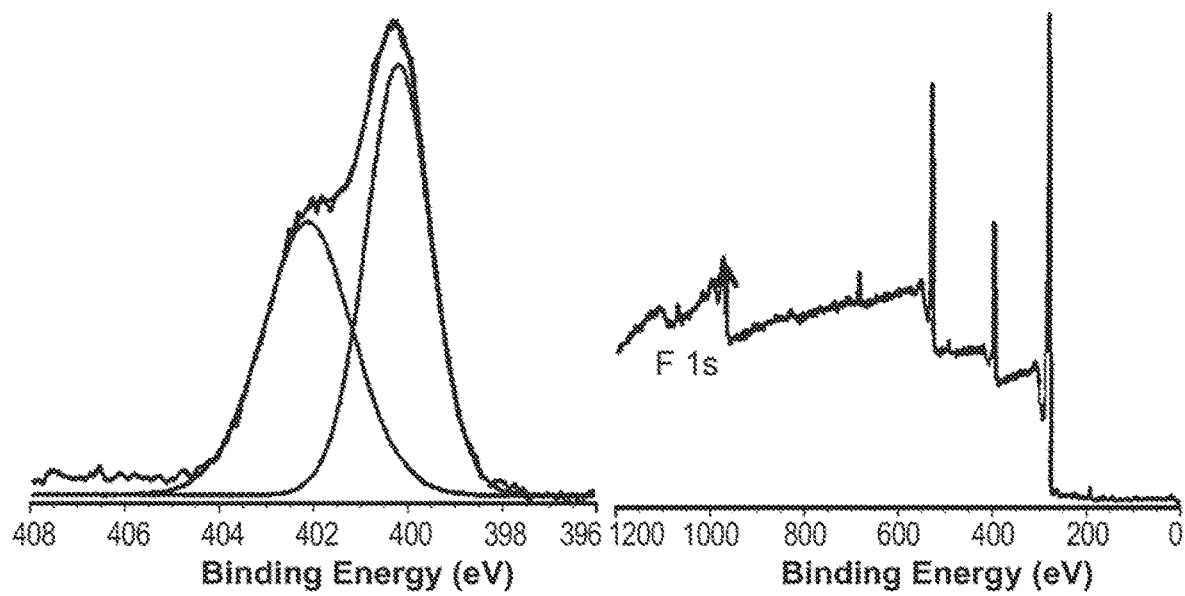
FIG. 17B shows representative data pertaining to the covalent attachment of PFPA to the surface of the membrane. Specifically, the XPS survey spectra and N is spectra of the RO membrane surface is shown.
Figure 19A:
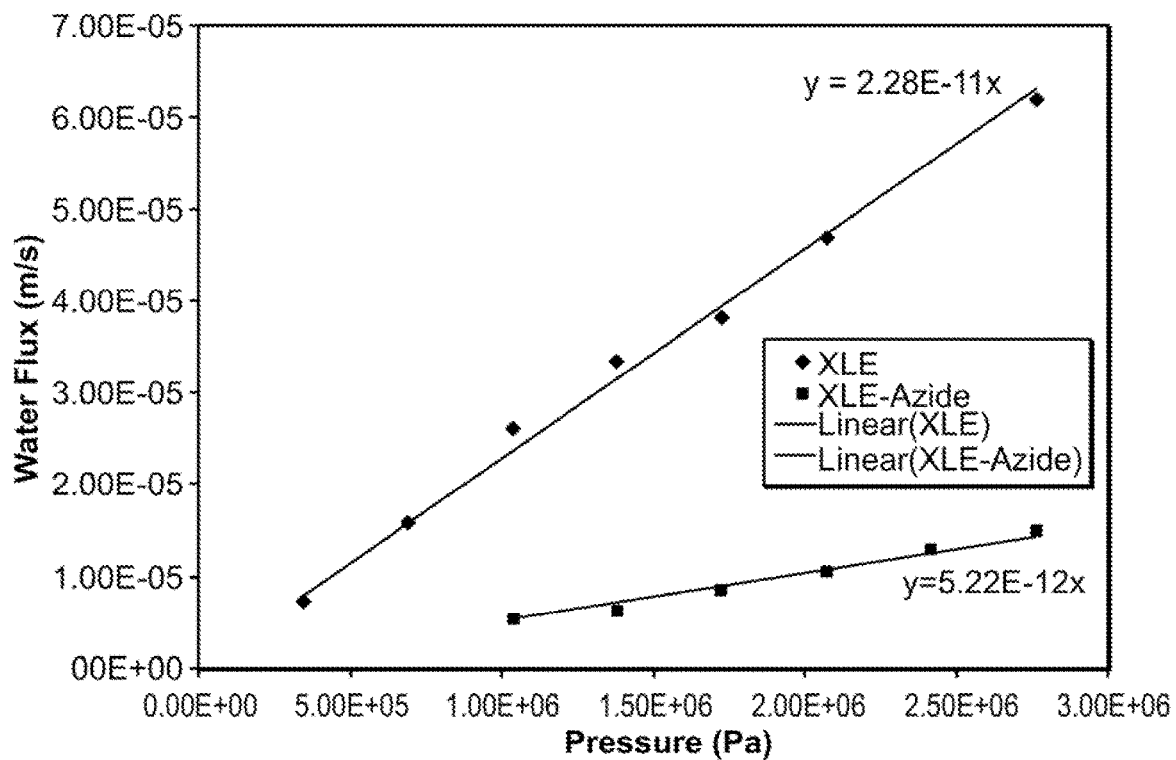
FIGS. 19A and 19B show representative data demonstrating the performance of commercial and PFPA-PEG$_n$ modified RO membranes.
Figure 19B:
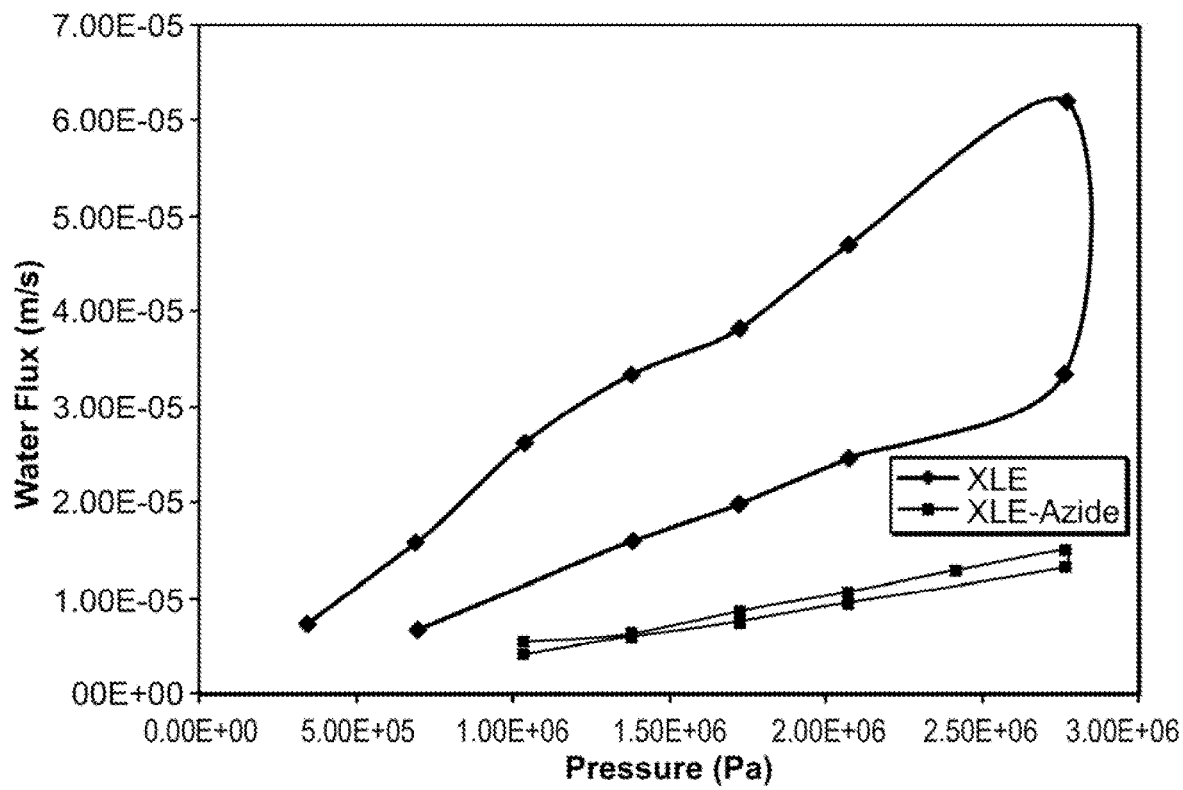

X-ray photoelectron spectroscopy (XPS) was employed to further elucidate the nature of the covalent attachment of PFPA to the surface of the PA membrane. Because the long PEG polymer chains dominate the XPS spectra, the small molecule 4-azidotetrafluorobenzoic acid (PFPA—COOH) was prepared and used to modify analytical samples for XPS measurements, shown in FIGS. 17A and 17B. When compared to the unmodified membrane, the N is spectrum for the modified membrane exhibits an additional peak at 402.2 eV, attributed to the newly formed aziridine linkage between the PFPA and the aromatic rings on the membrane surface (see U.S. Pat. No. 4,039,440). Furthermore, the absence of signal above 403 eV indicates that all Ar—N=N$^+$=N$^-$ expels N$_2$ during irradiation, as Ar—N=N$^+$=N$^-$ exhibits a distinct peak at 406.5 eV. Additionally, the modified membrane survey spectrum reveals the presence of the fluorine at 687.6 eV (FIG. 19B) and the C is spectrum displays a significant increase in the C—N bonding, further supporting the covalent attachment of PFPA derivatives.

4. Effect of PFPA Surface Modification on Membrane Performance

Figure 18:
FIG. 18 shows representative data pertaining to the pure water permeability and salt rejection of PFPA-PEG$_n$ modified RO membranes.

To determine the effect of the surface modification on the performance of commercial RO membranes, pure water permeability tests and NaCl rejection tests of the modified membranes were conducted (see Table I). As shown in FIG. 18, as well as in FIGS. 19A and 19B, the addition of hydrophilic polymers to the membrane surface reduces the pure water permeability and increases NaCl rejection due to steric hindrance (Cohen, Y., et al. (2013) *Membrane Surface Nanostructuring with Terminally Anchored Polymer Chains*. Functional Nanostructured Materials and Membranes for Water Treatment, Published Online 13 Feb. 2013). Moreover, systematically increasing the molecular weight of the brush polymer has a greater effect on the permeability and rejection, presumably caused by larger flexible polymers, the PFPA-PEG modified membranes exhibit higher fluxes than many commercially available RO membranes with comparable monovalent salt rejection (Jeong, B. H., et al. (2007) *J. Membr. Sci.* 294, 1-7).

TABLE I

| Pressure (psi) | Commercial RO membrane NaCl rejection | PFPA-NHPEG modified membrane NaCl rejection |
|---|---|---|
| 200 | 91.5 | 96.3 |
| 300 | 90.4 | 93.9 |
| 400 | 88.4 | 94.2 |

5. PFPA Modified Membranes Resist Cell Adhesion

Figure 20:
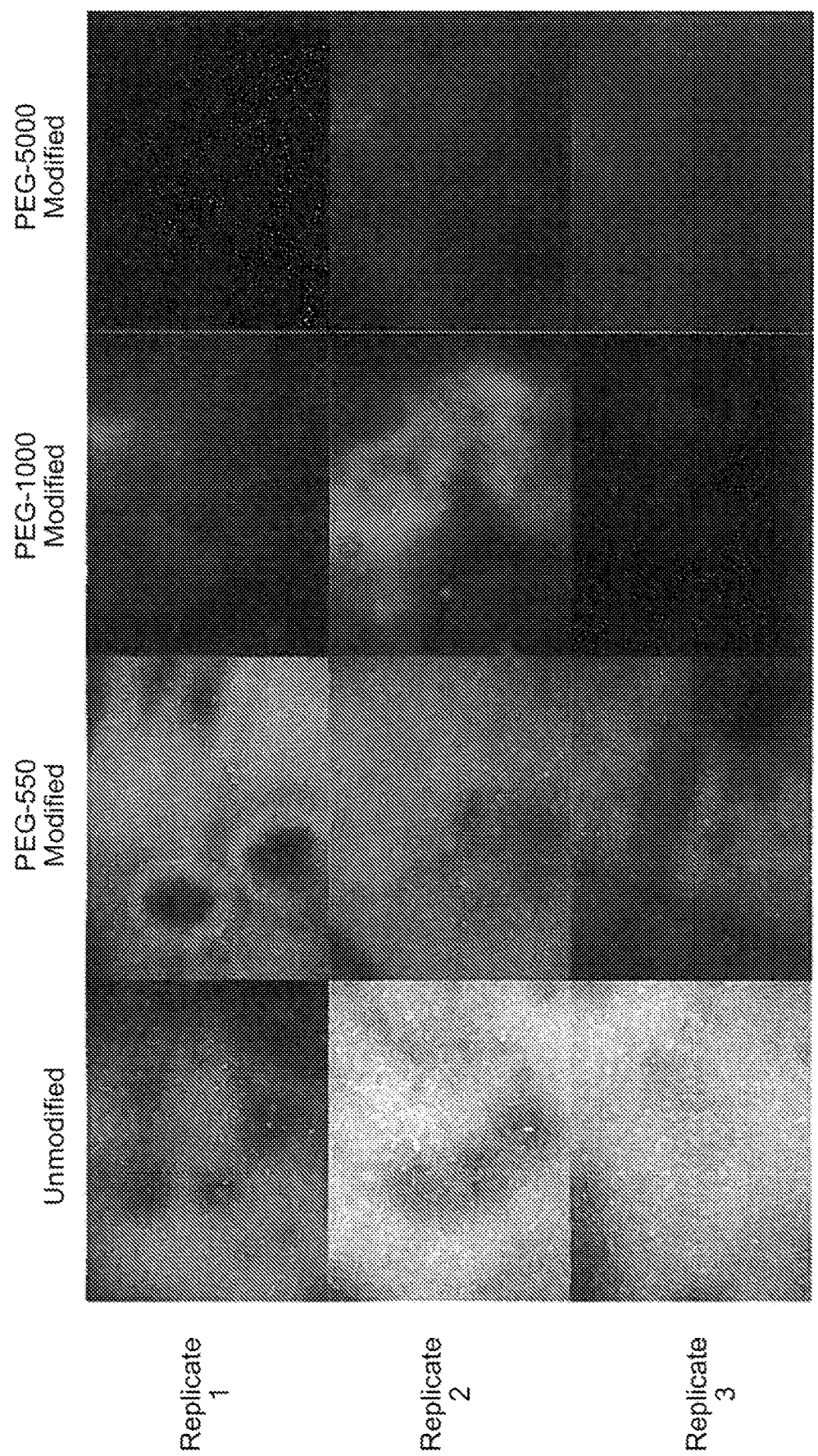
FIG. 20 shows representative data pertaining to the adhesion of *E. coli* on PFPA-PEG$_n$ modified membranes.
Figure 21:
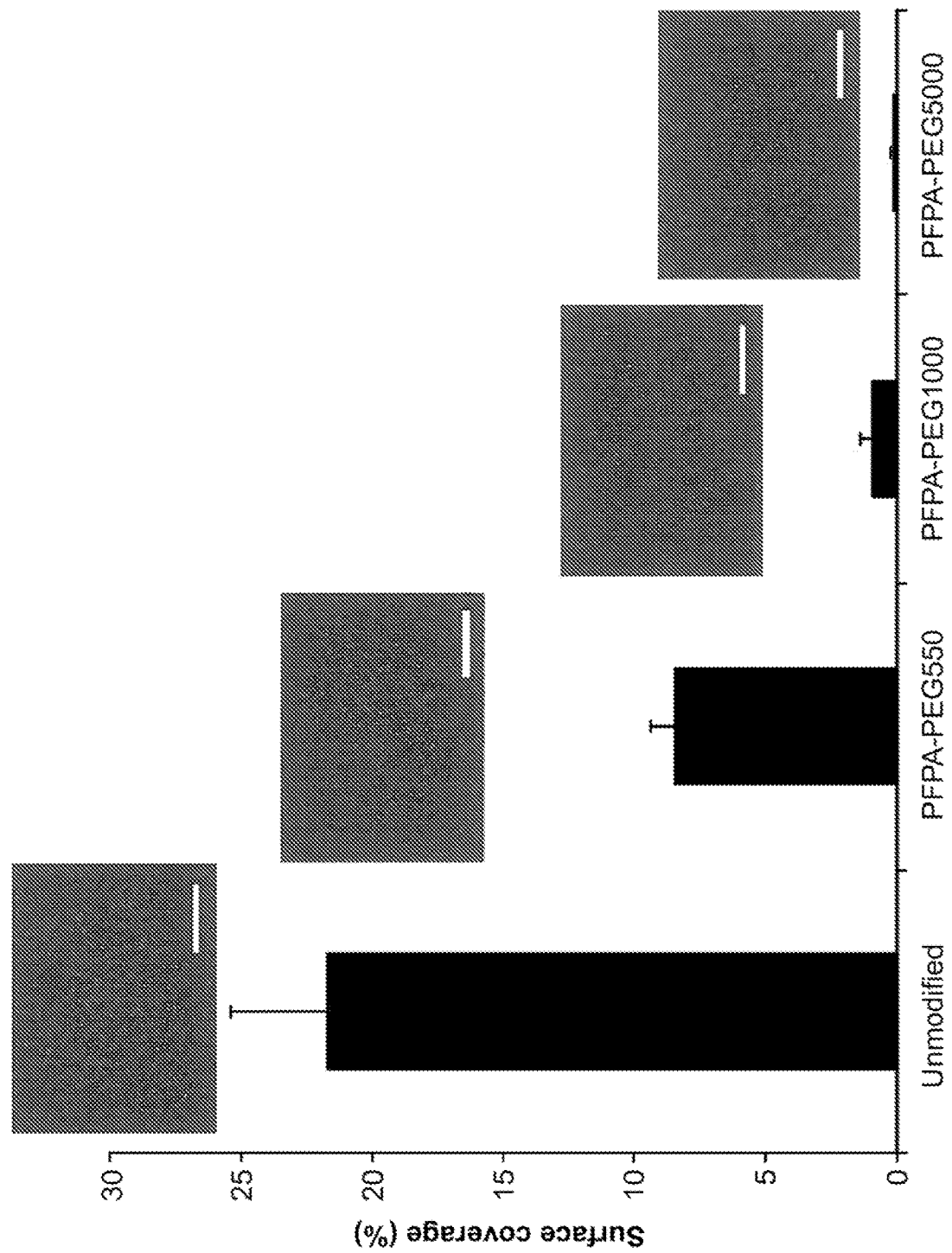
FIG. 21 shows representative data quantifying the adhesion of *E. coli* on PFPA-PEG$_n$ modified membranes.

The ability of the modified membrane to resist cell adhesion was challenged using *E. coli*, a gram-negative bacterium that is commonly used in anti-fouling experiments (Yang, R., et al. (2011) *Chem. Materials* 23, 1263-1272; Adout, A., et al. (2010) *Environ. Sci. Technol.* 44, 2406-2411; Tan, K., and Opendorf, S. K. J. (2007) *J. Membr. Sci.* 305, 287-298; Kim, S. H., et al. (2003) *J. Membr. Sci.* 211, 157-165). Because initial attachment of bacteria is crucial in biofilm formation, inhibiting bacterial adhesion prevents the growth and spreads of bacteria across a surface. In this study, *E. coli* adhesion on the modified and unmodified RO membranes was measured by fluorescent microscopy, following a modified procedure described by Rong and Gleason (Yang, R., et al. (2011) *Chem. Materials* 23, 1263-1272). Using ImageJ software (Abramoff, M. D., et al. (2004) *Biophotonics International* 11, 36-42), the surface coverage percentage of the adhered bacteria was measured and compared to the unmodified RO membrane. The fluorescent microscopy images are illustrated in FIG. 20 and the surface coverage analysis is depicted in FIG. 21. Regarding the unmodified RO membrane, ~22% of the membrane surface was covered with irreversibly attached *E. coli*. When modified with PFPA-PEG$_n$ derivatives, notably less attachment was observed for the membranes. The membranes modified with PFPA-PEG$_{550}$ and PFPG-PEG$_{1000}$ showed less adhered bacteria, and <1% of the surface was covered with *E. coli* on the membranes modified with PFPA-PEG$_{5000}$. Thus, without wishing to be bound by theory, increased PEG molecular weight (chain length) may be directly related to the anti-fouling ability of the modified membrane.

6. Zeta Potential

Figure 22:
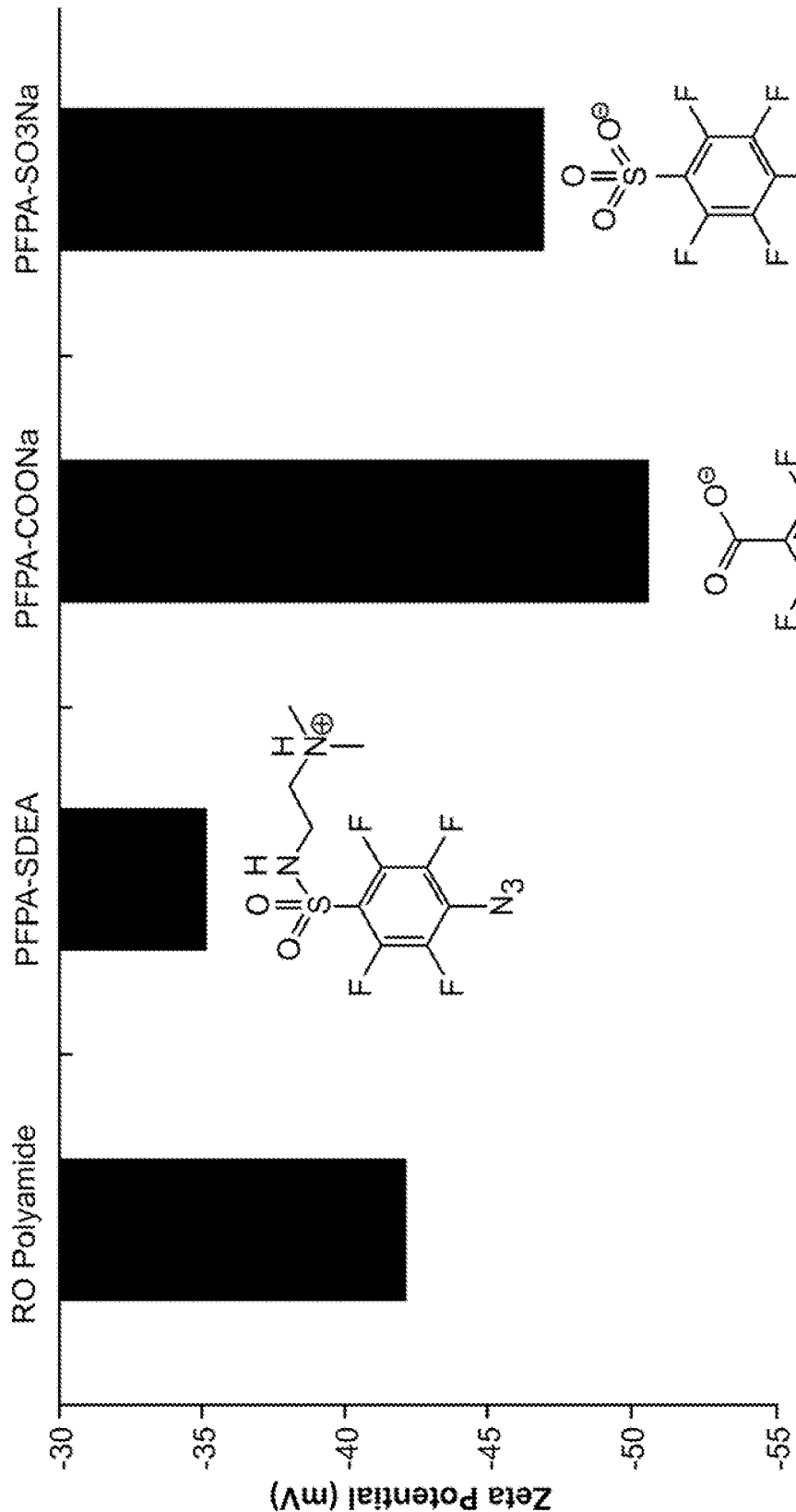
FIG. 22 shows representative data pertaining to the effect of PFPA modification on zeta potential.

To investigate changes in surface charge after modification, streaming potential measurements were performed on the control and modified membranes. The results, illustrated in FIG. 22, indicate a decrease in zeta potential for the membranes modified with acidic functional groups (PFPA—COONa and PFPA—SO$_3$Na) compared to the unmodified membrane. In contrast, the PFPA-SDEA modified membrane resulted in an increase in zeta potential compared to the control.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

H. References

Abramoff, M. D.; Magalhaes, P. J.; Ram, S. J. (2004) Image Processing with ImageJ. *Biophotonics International*, 11 (7), 36-42.

Adout, A.; Kang, S.; Asatekin, S.; Mayes, A. M.; Elimelech, M. (2010) Ultrafiltration Membranes Incorporating Amphiphilic Comb Copolymer Additives Prevent Irreversible Adhesion of Bacteria. *Environ. Sci. Technol.*, 44, 2406-2411.

Andreatta, A.; Cao, Y.; Chiang, J. C.; Heeger, A. J.; Smith, P. (1988) Electrically-conductive fibers of polyaniline spun from solutions in concentrated sulfuric acid. *Synthetic Metals*, 26 (4), 383-389.

Ang, W. S.; Lee, S. Y.; Elimelech, M. (2006) Chemical and physical aspects of cleaning of organic-fouled reverse osmosis membranes. *Journal of Membrane Science*, 272 (1-2), 198-210.

Bartlett, M. A.; Yan, M. (2001) Fabrication of Polymer Thin Films and Arrays with Spatial and Topographical Controls. *Adv. Mater.* 13(19), 1449-1451.

Baker, J. S.; Dudley, L. Y. (1998) Biofouling in membrane systems: A review. *Desalination*, 118 (1-3), 81-89.

Banerjee, I.; Pangule, R. C.; Kaner, R. S. (2011) Antifouling Coatings: Recent Developments in the Design of Surfaces That Prevent Fouling by Proteins, Bacteria, and Marine Organisms. *Advanced Materials*, 23, 690-718.

Belfer, S.; Purinson, Y.; Fainshtein, R.; Radchenko, Y.; Kedem, O. (1998) Surface modification of commercial composite polyamide reverse osmosis membranes. *Journal of Membrane Science*, 139 (2), 175-181.

Cadotte, J. E. (1977) Reverse Osmosis Membrane. U.S. Pat. No. 4,039,440.

Cao, Y.; Andreatta, A.; Heeger, A. J.; Smith, P. (1989) Influence of chemical polymerization conditions on the properties of polyaniline. *Polymer*, 30 (12), 2305-2311.

Chen, H.; Belfort, G. (1999) Surface modification of poly (ether sulfone) ultrafiltration membranes by low-temperature plasma-induced graft polymerization. *J. Appl. Polym. Sci.*, 72 (13), 1699-1711.

Chiang, J. C.; MacDiarmid, A. G. (1986) 'Polyaniline': Protonic acid doping of the emeraldine form to the metallic regime. *Synthetic Metals*, 13 (1-3), 193-205.

Choo, K. H.; Lee, C. H. (1996) Membrane fouling mechanisms in the membrane-coupled anaerobic bioreactor. *Water Res.*, 30 (8), 1771-1780.

Cho, J.; Amy, G.; Pellegrino, J. (2000) Membrane filtration of natural organic matter: factors and mechanisms affecting rejection and flux decline with charged ultrafiltration (UF) membrane. *Journal of Membrane Science*, 164 (1-2), 89-110.

Chung, H. Y.; Yang, J. M.; Tolbert, S. H.; Kaner, R. B. (2008) Anisotropic mechanical properties of ultra-incompressible osmium di-boride. *Journal of Materials Research*, 23, 1797-1801.

Chung, H. Y.; Weinberger, M. B.; Yang, J. M.; Tolbert, S. H.; Kaner, R. B. (2008) Correlation between hardness and elastic moduli of the ultra-incompressible transition metal di-borides RuB$_2$, OsB$_2$ and ReB$_2$. *Applied Physics Letters*, 92, 261904-261907.

Cohen, Y.; Lin, N.; Varin, K.; Chien, D.; Hicks, R. F. (2013) Membrane Surface Nanostructuring with Terminally Anchored Polymer Chains. In *Functional Nanostructured Materials and Membranes for Water Treatment* (eds M. Duke, D. Zhao and R. Semiat), Wiley-VCH Verlag GmbH & Co. KGaA, Weinheim, Germany.

Damoiseux, R.; George, S.; Li, M.; Pokhrel, S.; Ji, Z.; France, B.; Xia, T.; Suarez, E.; Rallo, R.; Madler, L.; Cohen, Y.; Hoek, E. M. Y.; Nel, A. E. (2011) No Time to Lose-High Throughput Screening to Assess Nanomaterial Safety. *Nanotechnology*, 3, 1345-1360.

Decarolis, J.; Hong, S.; Taylor, J. (2001) Fouling behavior of a pilot scale inside-out hollow fiber UF membrane during dead-end filtration of tertiary wastewater. *Journal of Membrane Science*, 191 (1-2), 165-178.

Drechsler, A.; Grundke, K. (2005) The influence of electrolyte ions on the interaction forces between polystyrene surfaces. *Colloid Surf A-Physicochem. Eng. Asp.*, 264 (1-3), 157-165.

Elimelech, M.; Phillip, W. (2011) The future of desalination: energy, technology, and the environment. *Science*, 333 (6043), 712-7177.

Glater, J.; Hong, S.; Elimelech, M. (1994) The search for a chlorine-resistant reverse osmosis membrane. *Desalination*, 95 (3), 325-345.

Gizdavic-Nikolaidis, M. R.; Bennett, J. R.; Swift, S.; Easteal, A. J.; Ambrose, M. (2011) Broad spectrum antimicrobial activity of functionalized polyanilines. *Acta Biomaterialia*, 7, 4204-4209.

Guillen, G. R.; Pan, Y.; Li, M.; Hoek, E. M. Y. (2011) Preparation and Characterization of Membranes Formed by Non-solvent Induced Phase Separation: A Review. *Industrial and Engineering Chemistry Research*, 50, 3798-3817.

Goosen, M. F. A.; Sablani, S. S.; Al-Hinai, H.; Al-Obeidani, S.; Al-Belushi, R.; Jackson, D. (2004) Fouling of Reverse Osmosis and Ultrafiltration Membrane: A Critical Review. *Sep. Sci. Technol.*, 39 (10), 2261-2297.

Herzberg, M.; Elimelech, M. (2007) Biofouling of reverse osmosis membranes: Role of biofilm-enhanced osmotic pressure. *Journal of Membrane Science*, 295 (1-2), 11-20.

Hoek, E. M. Y.; Kim, A. S.; Elimelech, M. (2002) Influence of cross-flow membrane filter geometry and shear rate on colloidal fouling in reverse osmosis and nanofiltration separations. *Environmental Engineering Sciences,* 19 (6), 357-372.

Hoek, E. M. V.; Bhattacharjee, S.; Elimelech, M. (2003) Effect of membrane surface roughness on colloid-membrane DLVO interactions. *Langmuir,* 19 (11), 4836-4847.

Hoek, E. M. V.; Agarwal, G. K. (2006) Extended DLVO interactions between spherical particles and rough surfaces. *J Colloid Interf Sci.,* 298 (1), 50-58.

Hong, S. K.; Elimelech, M. (1997) Chemical and physical aspects of cleaning of natural organic matter (NOM) fouling of nanofiltration membranes. *Journal of Membrane Science,* 132 (2), 159-181.

Howe, K. J.; Marwah, A.; Chiu, K. P.; Adham, S. S. (2006) Effect of Coagulation on the Size of MF and UF Membrane Foulants. *Environmental Science and Technology,* 40 (24), 7908-7913.

Isaias, N. P. (2001) Experience in reverse osmosis pretreatment. *Desalination,* 139 (1-3), 57-64.

Israelachvili, J. N., *Intermolecular and Surface Forces.* 2nd ed.; Academic Press: London, 1992.

Jeong, B. H.; Hoek, E. M. V; Yan, Y.; Subramani, A.; Huang, X.; Hurwitz, G.; Jawor, A. (2007) Interfacial polymerization of thin film nanocomposites: A new concept for reverse osmosis membranes. *Journal of Membrane Science,* 294 (1-2), 1-7.

Ji, Z.; Jin, X.; George, S.; Xia, T.; Meng, H.; Wang, X.; Suarez, E.; Zhang, H.; Hoek, E. M. Y.; Godwin, H.; Nel, A. E.; Zink, J. I. (2010) Dispersion and Stability Optimization of TiO$_2$ Nanoparticles in Cell Culture Media. *Environmental Science and Technology,* 44, 7309-7314.

Jiang, S.; Cao, A. (2010) Ultralow-Fouling, Functionalizable, and Hydrolyzable Zwitterionic Materials and Their Derivatives for Biological Applications. *Advanced Materials,* 22, 920-932.

Jin, X.; Li, M.; Wang, J.; Marambio-Jones, C.; Huang, X.; Damoiseux, R.; Hoek, E. M. V. (2010) High-throughput Screening of Silver Nanoparticle Stability and Bioavailability in Simulated Fresh Water: Influence of Specific Ions. *Environmental Science and Technology,* 44, 7321-7328.

Kaner, R. B.; Tolbert, S. H.; Kavner, A.; Yang, J. M.; Levine, J. B.; Cumberland, R. W.; Gilman, J. J.; Chung, H. Y.; Weinberger, M. (2008) Rhenium di-boride, an ultra-incompressible, super-hard material.

Kang, G.; Cao, Y. (2012) Development of anti-fouling reverse osmosis membranes for water treatment: A review. *Water research,* 46(3), 584-600.

Kang, G. D.; Gao, C. J.; Chen, W. D.; Jie, X. M.; Cao, Y. M.; Yuan, Q. (2007) Study on hypochlorite degradation of aromatic polyamide reverse osmosis membrane. *Journal of Membrane Science,* 300 (1-2), 165-171.

Kang, G.; Lui, M.; Cao, Y.; Yuan, Q. (2007) A novel method of surface modification on thin-film composite reverse osmosis membrane by grafting poly(ethylene glycol). *Polymer,* 48 (5), 1165-1170.

Kang, G.; Yu, H.; Liu, Z.; Cao, Y. (2011) Surface modification of a commercial thin film composite polyamide reverse osmosis membrane by carbodiimide-induced grafting with poly(ethylene glycol) derivatives. *Desalination,* 275 (1-3), 252-259.

Kawaguchi, T.; Tamura, H. (1984) Chlorine-resistant membrane for reverse osmosis. I. Correlation between chemical structures and chlorine resistance of polyamides. *Journal of Applied Polymer Science,* 29 (11), 3359-3367.

Keana, J. F. W.; Cai, S. X. (1990) New reagents for photoaffinity labeling: synthesis and photolysis of functionalized perfluorophenyl azides. *The Journal of Organic Chemistry,* 55 (11), 3640-3647.

Kim, K. S.; Lee, K. H.; Cho, K.; Park, C. E. (2002) Surface modification of polysulfone ultrafiltration membrane by oxygen plasma treatment. *Journal of Membrane Science* 199 (1-2), 135-145.

Kim, S. H.; Kwak, S. Y.; Sohn, B.; Park, T. H. (2003) Design of TiO$_2$ nanoparticle self-assembled aromatic polyamide thin-film-composite (TFC) membrane as an approach to solve biofouling problem. *J. Membr. Sci.,* 211, 157-165.

Lawrence, N. D.; Perera, J. M.; Iyer, M.; Hickey, M. W.; Stevens, G. W. (2006) Use of streaming potential measurements to study the fouling and cleaning of ultrafiltration membranes. *Sep. Purif Technol.,* 48, 106-112.

Lee, H.; Lee, S. G.; Oh, E. J.; Chung, H. Y.; Han, S. I.; Kim, E. J.; Seo, S. Y.; Ghim, H. D.; Yeum, J. H.; Choi, J. H. (2011) Antimicrobial polyethyleneimine-silver nanoparticles in a stable colloidal dispersion. *Colloids and Surfaces B: Biointerfaces,* 88 (1), 505-511.

Lee, K. P.; Arnot, T. C.; Mattia, D. (2011). A review of reverse osmosis membrane materials for desalination-Development to date and future potential. *Journal of Membrane Science,* 370 (1-2), 1-22.

Lee, N.; Amy, G.; Croue, J. P.; Buisson, H. (2004) Identification and understanding of fouling in low-pressure membrane (MF/UF) filtration by natural organic matter (NOM). *Water Res.,* 38 (20), 4511-4523.

Lee, S.; Elimelech, M. (2006) Relating organic fouling of reverse osmosis membranes to intermolecular adhesion forces. *Environ. Sci. Technol.,* 40 (3), 980-987.

Leng, W.; Zhou, S.; Gu, G.; Wu, L. (2012) Wettability switching of SDS-doped polyaniline from hydrophobic to hydrophilic induced by alkaline/reduction reactions. *J. Colloid Interf Sci.,* 369 (1), 411-418.

Levine, J. B.; Nguyen, S. L.; Rasool, H. 1.; Wright, J. A.; Brown, S. E.; Kaner, R. B. (2008) Preparation and properties of metallic, super-hard rhenium di-boride crystals. *Journal of the American Chemical Society,* 130, 16953-16958.

Levine, J. B.; Tolbert, S. H.; Kaner, R. B. (2009) Advancements in the search for super-hard ultra-incompressible metal borides. *Advanced Functional Materials,* 19, 3519-3533.

Levine, J. B.; Betts, J. B.; Garrett, J. D.; Guo, S. Q.; Eng, J. T.; Migliori, A.; Kaner, R. B. (2010) Full elastic tensor of a crystal of the super-hard compound ReB$_2$. *Acta Materialia,* 58, 1530-1535.

Leyva, E.; Young, M. J. T.; Platz, M. S. (1986). High yields of formal CH insertion products in the reactions of polyfluorinated aromatic nitrenes. *J. Am. Chem. Soc.,* 108, 8307-8309.

Li, M.; Jin, X.; Maedler, L.; Pokhrel, S.; Damoiseux, R.; Hoek, E. M. V. (2011) Stability, Bioavailability, and Bacterial Toxicity of ZnO and Iron-doped ZnO Nanoparticles in Aquatic Media. *Environmental Science and Technology,* 45, 755-761.

Li, M.; Noriega-Trevino, M. E.; Nino-Martinez, N.; Marambio-Jones, C.; Damoiseux, R. E.; Ruiz, F.; Hoek, E. M. Y. (2011) Synergistic Bactericidal Activity Ag—TiO$_2$ Nanoparticles in Both Light and Dark Conditions. *Environmental Science and Technology,* 45, 8989-8995.

Li, Q. L.; Elimelech, M. (2004) Organic fouling and chemical cleaning of nanofiltration membranes: Measurements and mechanisms. *Environ. Sci. Technol.*, 38 (17), 4683-4693.

Lin, N. H.; Kim, M.; Lewis, G. T.; Cohen, Y. (2010) Polymer surface nano-structuring of reverse osmosis membranes for fouling resistance and improved flux performance. *Journal of Materials Chemistry*, 20(22), 4642-4652.

Liu, L.; Engelhard, M. H.; Yan, M. (2006) Surface and Interface Control of Photochemically Initiated Immobilization. *Journal of the American Chemical Society*, 128, 14067-14072.

Liu, F.; Du, C. H.; Zhu, 8. K.; Xu, Y. Y. (2007) Surface immobilization of polymer brushes onto porous poly (vinylidene fluoride) membrane by electron beam to improve the hydropholicity and fouling resistance. *Polymer*, 48 (10), 2910-2918.

Liu, L. H.; Yan, M. (2010) Perfluorophenyl Azides: New Applications in Surface Functionalization and Nanomaterial Synthesis. *Accounts of Chemical Research*, 43 (11), 1434-1443.

Liu, L. H.; Yan, M. (2009) Simple Method for the Covalent Immobilization of Graphene. *Nano Letters*, 9 (9), 3375-3378.

Liu, L. H.; Zorn, G.; Castner, D. G.; Solanki, R.; Lerner, M. M.; Yan, M. (2010) A Simple and Scalable Route to Wafer-Size Patterned Graphene. *J. Mater. Chem.*, 20, 5041-5046.

Liu, L. H.; Yan, M. (2011) Functionalization of pristine graphene with perfluorophenyl azides. *Journals of Materials Chemistry*, 21, 3273-3276.

Ma, H.; Bowman, C. N.; Davis, R. H. (2000) Membrane fouling reduction by backpulsing and surface modification. *Journal of Membrane Science*, 173 (2), 191-200.

Madkour, T. M., *Polymer Data Handbook. Oxford University Press, Inc.*: 1999.

Maheshwari, R.; Sreeram, K. J.; Dhathathreyan, A. (2003) Surface energy of aqueous solutions of Hofmeister electrolytes at air/liquid and solid/liquid interface. *Chem. Phys. Lett.*, 375 (1-2), 157-161.

Marambio-Jones, C.; Hoek, E. M. Y. (2010) A Review of the Antibacterial Effects of Silver Nanomaterials and Potential Implications for Human Health and the Environment. *Journal of Nanoparticle Research*, 12, 1531-1551.

Martin, T. P.; Kooi, S. E.; Chang, S. H.; Sedransk, K. L.; Gleason, K. K. (2007). Initiated chemical vapor deposition of antimicrobial polymer coatings. *Biomaterials*, 28 (6), 909-915.

Mauter, M. S.; Wang, Y.; Okemgbo, K. C.; Osuji, C. O.; Giannelis, E. P.; Elimelech, M. (2011) Antifouling Ultrafiltration Membranes via Post-Fabrication Grafting of Biocidal Nanomaterials. *ACS Applied Materials and Interfaces*, 3 (8), 2861-2868.

Meng, F.; Zhang, H.; Yang, F.; Li, Y.; Xiao, J.; Zhang, X. (2006) Effect of filamentous bacteria on membrane fouling in submerged membrane bioreactor. *Journal of Membrane Science*, 27 (1-2), 161-168.

Merrifield, R. B. (1963) Solid Phase Peptide Synthesis. I. The Synthesis of a Tetrapeptide. *Journal of the American Chemical Society*, 65 (14), 2149-2154.

Miller, S. C. (2010). Profiling Sulfonate Ester Stability: Identification of Complementary Protecting Groups for Sulfonates. *The Journal of Organic Chemistry*, 75 (13), 4632-4635.

Montgomery, M. A.; Elimelech, M. (2007) Water and Sanitation in Developing Countries: Including Health in the Equation. *Environmental Science and Technology*, 41 (1), 17-24.

Morawietz, J.; Sander, W. (1996). Photochemistry of Fluorinated Phenyl Nitrenes: Matrix Isolation of Fluorinated Azirines. *The Journal of Organic Chemistry*, 61 (13), 4351-4354.

Nakajima, N.; Ikada, Y. (1995) Mechanism of Amide Formation by Carbodiimide for Bioconjugation in Aqueous Media. *Bioconjugate Chemistry*, 6 (1), 123-130.

Oss, C. J. v. (1993) Acid-base interfacial interactions in aqueous-media. *Colloid Surf A-Physicochem. Eng. Asp.*, 78, 1-49.

Pastine, S. J.; Okawa, D.; Kessler, B.; Rolandi, M.; Llorente, M.; Zettl, A.; Frechet, J. M. J. (2008) A Facile and Patternable Method for the Surface Modification of Carbon Nanotube Forests using Perfluoroarylazides. *J. Am. Chem. Soc.*, 130, 4238-4239.

Peng, F.; Hoek, E. M. Y.; Damoiseaux, R. (2010) High-content screen for biofilm assays. *Journal of Biomolecular Screening*, 17 (7), 748-754.

Poe, R.; Schnapp, K.; Young, M. J. T.; Grayzar, J.; Platz, M. S. (1992) Chemistry and kinetics of singlet pentafluorophenylnitrene. *Journal of the American Chemical Society*, 114 (13), 5054-5067.

Rana, D.; Matsuura, T. (2010) Surface modifications for antifouling membranes. *Chemical reviews*, 110 (4), 2448-2471.

Redondo, J. A, (2001) Brackish, sea and wastewater desalination, *Desalination*, 138, 28-31.

Reyes, Y. C.; Li, M.; Hoek, E. M. Y.; Mahendra, S.; Damoiseux, R. E. (2012) Time-Resolved Toxicity Assessment of Nanoparticles using a Genome-wide-Knockout Library of *Escherichia Coli*. *ACS Nano*, 6, 9402-9415.

Service, R. F. (2006) Desalination freshens up. *Science*, 313(5790), 1088-1090.

Shannon, M.; Bohn, P. W.; Elimelech, M.; Georgiadis, J. G.; Marifias, B. J.; Mayes, A. M. (2008) *Nature*, 452 (7185), 301-310.

Subramani, A.; Huang, X.; Hoek, E. M. V. (2006) Direct observation of microbial adhesion to reverse osmosis and nanofiltration membranes. *J Colloid Interface Sci.*, 336 (1), 13-20.

Suzuki, Y.; Levine, J. B.; Migliori, A.; Garrett, J. D.; Kaner, R. B.; Fanelli, Y. R.; Betts, J. B. (2010) Measurement of the five elastic moduli of rhenium di-boride from 308 K to 5 K. *The Journal of the Acoustical Society of America*, 127, 2797-2801.

Tan, K.; Obendorf, S. K. (2007) Development of an antimicrobial microporous polyurethane membrane. *J. Membr. Sci.*, 305, 287-298.

*The Nation's Report Card: Science* 2011; Institute of Education Sciences, U.S. Department of Education, Washington, D.C., 2012.

Tkachev, S. N.; Levine, J. B.; Kisliuk, A.; Sokolov, A. P.; Guo, S. Q.; Eng, J. T.; Kaner, R. B. (2009) Shear modulus of polycrystalline rhenium di-boride determined from surface Brillouin spectroscopy. *Advanced Materials*, 21, 4284-4286.

Van der Mei, H. C.; Bos, R.; Busscher, H. J. (1998) A reference guide to microbial cell surface hydrophobicity based on contact angles. *Colloid Surf B-Biointerfaces*, 11 (4), 213-221.

Van Oss, C. J., XXI: Adsorption and adhesion in aqueous media. In *Interfacial Forces in Aqueous Media*, Marcel Dekker, Inc.: New York, N.Y., 1994; pp 333-376.

Van Oss, C. J.; Giese, R. F.; Wu, W. (1997) On the predominant electron-donicity of polar solid surfaces. *J. Adhes.*, 63 (1-3), 71-88.

Van Oss, C. J.; Docoslis, A.; Wu, W.; Giese, R. F. (1999) Influence of macroscopic and microscopic interactions on kinetic rate constants—I. Role of the extended DLVO theory in determining the kinetic adsorption constant of proteins in aqueous media, using von Smoluchowski's approach. *Colloid Surf B-Biointerfaces*, 14 (1-4), 99-104.

Van Wagner, E. M.; Sagle, A. C.; Sharma, M. M.; La, Y. H.; Freeman, B. D. (2011) Surface modification of commercial polyamide desalination membranes using poly(ethylene glycol) diglycidyl ether to enhance membrane fouling resistance. *Journal of Membrane Science*, 367 (1-2), 273-287.

Vrijenhoek, E. M.; Hong, S.; Elimelech, M. (2001) Influence of membrane surface properties on initial rate of colloidal fouling of reverse osmosis and nanofiltration membranes. *Journal of Membrane Science*, 188, 115-128.

Wang, S.; Guillen, G.; Hoek, E. M. V. (2005) Direct observation of microbial adhesion to membranes. *Environ. Sci. Technol.*, 39 (17), 6461-6469.

Wavhal, D. S.; Fisher, E. R. (2003) Membrane Surface Modification by Plasma-Induced Polymerization of Acrylamide for Improved Surface Properties and Reduced Protein Fouling. *Langmuir*, 19 (1), 79-85.

Welzel, P. B.; Rauwolf, C.; Yudin, O.; Grundke, K. (2002) Influence of aqueous electrolytes on the wetting behavior of hydrophobic solid polymers—Low-rate dynamic liquid/fluid contact angle measurements using axisymmetric drop shape analysis. *J Colloid Interface Sci.*, 251 (1), 101-108.

Weinberger, M.; Levine, J. B.; Chung, H. Y.; Cumberland, R. W.; Rasool, H.; Yang, J. M.; Kaner, R. B.; Tolbert, S. H. (2009) Incompressibility and hardness of solid solution transition metal di-borides: Ru1-xOsxB2. *Chemistry of Materials*, 21, 1915-1921.

World Health Organization. (2013). *Progress on Sanitation and Drinking-Water* (pp. 1-40).

Yan, M.; Cai, S. X.; Wybourne, M. N.; Keana, J. F. W. (1993) Photochemical Functionalization of Polymer Surfaces and the Production of Biomolecule-Carrying Micrometer-Scale Structures by Deep-UY Lithography using 4-Substituted Perfluorophenyl Azides. *Journals of the American Chemical Society*, 115, 814-816.

Yan, M. (2000) Covalent functionalization of natural rubber latex. *Reactive and Functional Polymers*, 45 (2), 137-144.

Yan, M.; Cai, S. X.; Keana, J. F. W. (1994) Photochemical and Thermal-Reactions of C-60 with N—Succinimidyl 4-Azido-2,3,5,6-tetrafluorobenzoate—A New Method for Functionalization of C-60. *J. Org. Chem.*, 59, 5951-5954.

Yang, R.; Xu, J.; Ozaydin-Ince, G.; Wong, S. Y.; Gleason, K. K. (2011) Surface-Tethered Zwitterionic Ultrathin Antifouling Coatings on Reverse Osmosis Membranes by Initiated Chemical Vapor Deposition. *Chemistry of Materials*, 23 (5), 1263-1272.

Zhu, X.; Elimelech, M. (1997) Colloidal Fouling of Reverse Osmosis Membranes: Measurements and Fouling Mechanism. *Environmental Science and Technology*, 31, 3654-3662.

Zou, L.; Vidalis, I.; Steele, D.; Michelmore, A.; Low, S. P.; Verberk, J. Q. (2011) Surface hydrophilic modification of RO membranes by plasma polymerization for low organic fouling. *Journal of Membrane Science*, 369 (1-2), 420-428.

What is claimed is:

1. A compound having a structure represented by a formula:

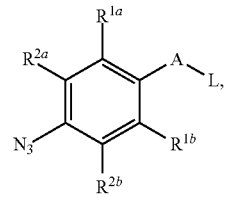

wherein A is —C(=O)— and L is —OQ;
wherein Q is a structure represented by a formula:

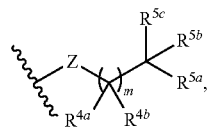

wherein Z is —CR$^{6a}$R$^{6b}$—, —C(=O)—, —C(=NH)—, or —C(=NH)NR$^7$—;
wherein each of R$^{1a}$ and R$^{1b}$ is independently hydrogen or halogen;
wherein each of R$^{2a}$ and R$^{2b}$ is halogen;
wherein each of R$^{4a}$ and R$^{4b}$, when present, is independently hydrogen, halogen, —CN, —OH, —NR$^{8a}$R$^{8b}$, —NR$^{8a}$R$^{8b}$ H$^+$, C1-C4 alkyl, C1-C4 monohaloalkyl, C1-C4 polyhaloalkyl, —SO$_3^-$, —SO$_3$R$^9$, —CO$_2^-$, or —CO$_2$R$^9$;
wherein R$^{5a}$ is —SO$_3^-$, —SO$_3$R$^9$, —CO$_2^-$, or —CO$_2$R$^9$;
wherein each of R$^{5b}$ and R$^{5c}$ is independently hydrogen, halogen, —CN, —OH, —NR$^{10a}$R$^{10b}$, —NR$^{10a}$R$^{10b}$H$^+$, C1-C4 alkyl, C1-C4 monohaloalkyl, C1-C4 polyhaloalkyl, —SO$_3^-$, —SO$_3$R$^{11}$, —CO$_2^-$, or —CO$_2$R$^{11}$;
wherein m is an integer selected from 0, 1, 2, 3, 4, 5, 6, 7, and 8;
wherein each of R$^{6a}$ and R$^{6b}$, when present, is independently hydrogen, halogen, —CN, —OH, —NR$^{12a}$R$^{12b}$, —NR$^{12a}$R$^{12b}$ H$^+$, C1-C4 alkyl, C1-C4 monohaloalkyl, C1-C4 polyhaloalkyl, —SO$_3^-$, —SO$_3$R$^{13}$, —CO$_2^-$, or —CO$_2$R$^{13}$;
wherein R$^7$, when present, is hydrogen or C1-C4 alkyl;
wherein each of R$^{8a}$ and R$^{8b}$, when present, is independently hydrogen or C1-C4 alkyl;
wherein R$^9$, when present, is hydrogen or C1-C4 alkyl;
wherein each of R$^{10a}$ and R$^{10b}$, when present, is independently hydrogen or C1-C4 alkyl;
wherein R$^{11}$, when present, is hydrogen or C1-C4 alkyl;
wherein each of R$^{12a}$ and R$^{12b}$, when present, is independently hydrogen or C1-C4 alkyl; and
wherein R$^{13}$, when present, is hydrogen or C1-C4 alkyl.

2. The compound of claim 1, wherein m is 0.

3. The compound of claim 1, wherein m is an integer selected from 0, 1, 2, 3, and 4.

4. The compound of claim 1, wherein Z is —CH$_2$—or —C(=NH)NH—.

5. The compound of claim 1, wherein the halogen is —F or —Cl.

6. The compound of claim 1, wherein the halogen is —F.

7. The compound of claim 1, wherein $R^{5a}$ is $CO_2^-$, $R^{5b}$ is —$NH_3^+$, and $R^{5c}$ is hydrogen.

8. The compound of claim 1, wherein $R^{5a}$ is —$CO_2^-$, and each of $R^{5b}$ and $R^{5c}$ is hydrogen.

9. The compound of claim 1, wherein the compound has a structure selected from:

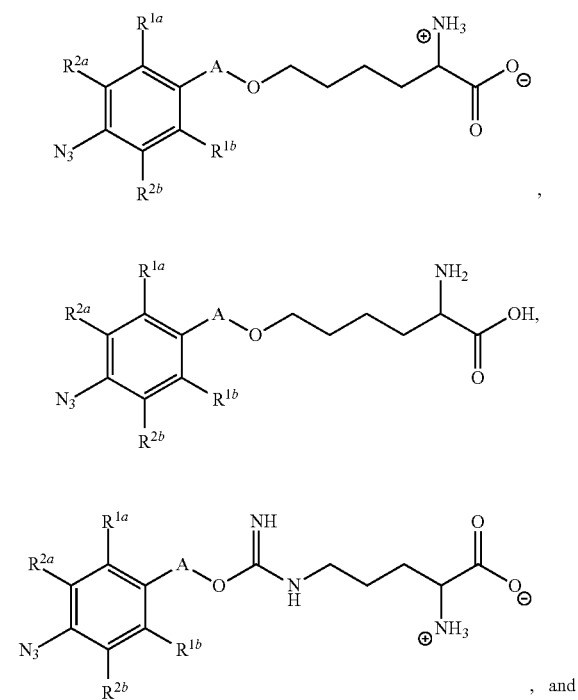

, and

10. The compound of claim 1, wherein the compound has a structure selected from:

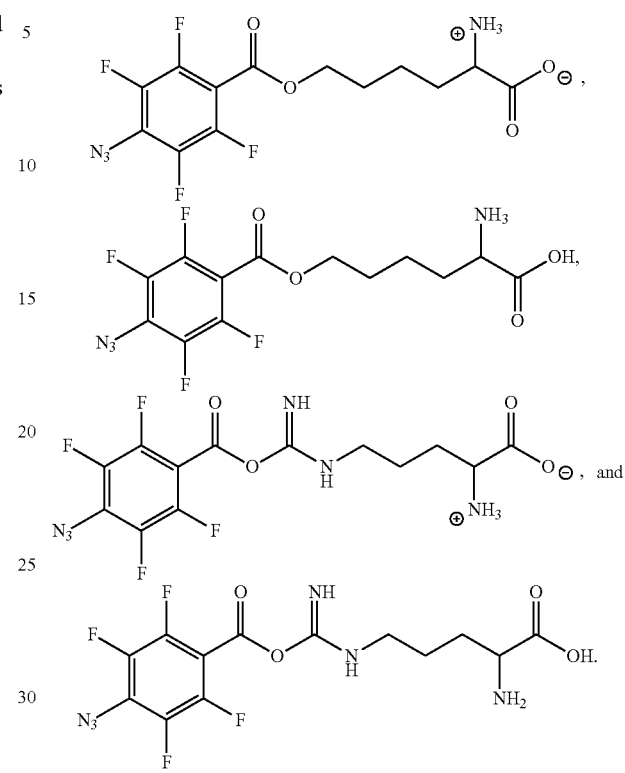

11. The compound of claim 1, wherein the compound has a structure of:

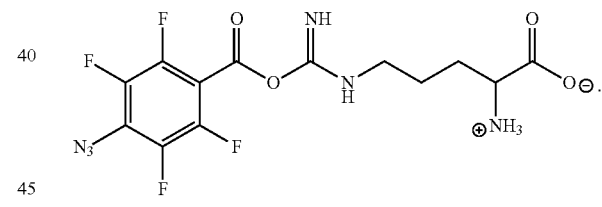

* * * * *